United States Patent
Walk et al.

(10) Patent No.: US 7,873,481 B2
(45) Date of Patent: Jan. 18, 2011

(54) SYSTEM AND METHOD FOR ANALYZING A SAMPLE USING CHROMATOGRAPHY COUPLED MASS SPECTROMETRY

(75) Inventors: Tilmann B. Walk, Kleinmachnow (DE); Ralf Looser, Berlin (DE); Bianca Bethan, Berlin (DE); Michael Manfred Herold, Berlin (DE); Beate Kamlage, Berlin (DE); Oliver Schmitz, Dallgow-Doeberitz (DE); Jan C. Wiemer, Berlin (DE); Alexandre Prokoudine, Berlin (DE); Bennard Van Ravenzwaay, Altrip (DE); Werner Mellert, Hassloch (DE); Georgia Coelho Palermo Cunha, Limburgerhof (DE); Thomas Ehrhardt, Speyer (DE); Gerhard Krennrich, Frankenthal (DE)

(73) Assignee: Metanomics GmbH, Berlin (DE)

( * ) Notice: Subject to any disclaimer, the term of this patent is extended or adjusted under 35 U.S.C. 154(b) by 540 days.

(21) Appl. No.: 11/996,777

(22) PCT Filed: Jul. 25, 2006

(86) PCT No.: PCT/EP2006/064628

§ 371 (c)(1),
(2), (4) Date: Jan. 25, 2008

(87) PCT Pub. No.: WO2007/012643

PCT Pub. Date: Feb. 1, 2007

(65) Prior Publication Data

US 2008/0234945 A1 Sep. 25, 2008

(30) Foreign Application Priority Data

Jul. 25, 2005 (EP) .................................. 05016068

(51) Int. Cl.
*G06F 19/00* (2006.01)

(52) U.S. Cl. ........................................ 702/19; 324/717
(58) Field of Classification Search .................. 702/19, 702/22, 2, 23, 24, 27, 28, 30, 32, 182–185; 250/339.07, 339.05, 339.06, 339.13, 341.8; 324/717, 310
See application file for complete search history.

(56) References Cited

U.S. PATENT DOCUMENTS 4,540,884 A 9/1985 Stafford et al.

(Continued)

FOREIGN PATENT DOCUMENTS

WO WO-03/041834 A1 5/2003

(Continued)

OTHER PUBLICATIONS

Jenkins, Helen, et al., "Toward Supportive Data Collection Tools for Plant Metabolomics", Plant Physiology, vol. 138 (2005), pp. 67-77.

(Continued)

*Primary Examiner*—Edward Raymond
(74) *Attorney, Agent, or Firm*—Connolly Bove Lodge & Hutz LLP

(57) ABSTRACT

A method for analyzing a test sample is disclosed, the test sample comprising at least one compound. A test sample comprising at least one compound is provided. Next, the at least one compound in the test sample is determined, thereby generating raw results. The generated raw results are analyzed, wherein the analysis of the test sample is accompanied by an analysis of at least one reference sample. The test sample and the reference sample are analyzed in an identical sequence in each step of the method. A system for carrying out the method is also disclosed.

107 Claims, 19 Drawing Sheets

U.S. PATENT DOCUMENTS

Figure 1:
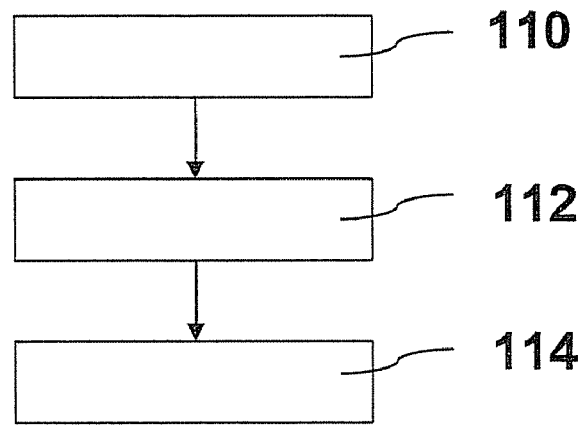
Figure 1:
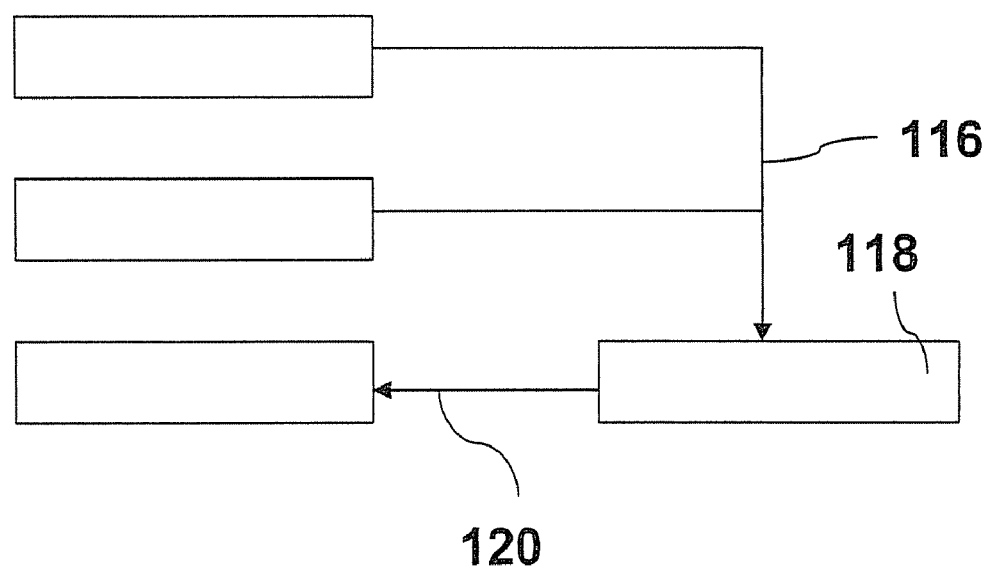

| | | | |
|---|---|---|---|
| 5,397,894 | A | 3/1995 | Wells et al. |
| 7,196,323 | B2 | 3/2007 | Walk et al. |
| 7,606,667 | B2 * | 10/2009 | Herold et al. ............... 702/22 |
| 7,645,984 | B2 * | 1/2010 | Gorenstein et al. ......... 250/281 |
| 2004/0260105 | A1 | 12/2004 | Herold et al. |
| 2005/0116159 | A1 | 6/2005 | Becker et al. |
| 2005/0127287 | A1 | 6/2005 | Plumb et al. |
| 2006/0255258 | A1 * | 11/2006 | Wang et al. ............... 250/282 |
| 2010/0187414 | A1 * | 7/2010 | Gorenstein et al. ......... 250/282 |

FOREIGN PATENT DOCUMENTS

| | | |
|---|---|---|
| WO | WO-03/046798 A1 | 6/2003 |
| WO | WO-03/073464 A1 | 9/2003 |
| WO | WO-03/092869 A1 | 11/2003 |
| WO | WO-03/102543 A1 | 12/2003 |
| WO | WO-2004/038602 A1 | 5/2004 |

OTHER PUBLICATIONS

O'Hagan, Steve, et al., "Closed-Loop, Multiobjecctive Optimization of Analytical Instrumentation: Gas Chromatography/Time-of-Flight Mass Spectrometry of the Metabolomes of Human Serum and of Yeast Fermentations", Analytical Chemistry, vol. 77, No. 1, (2005), pp. 290-303.

Stein, S.E., "An Integrated Method for Spectrum Extraction and Compound Identification from Gas Chromatography/Mass Spectrometry Data", Journal of the American Society for Mass Spectrometry, Elsevier Science Inc., vol. 10, (1999), pp. 770-781.

Colby, Bruce N., "Spectral Deconvolution for Overlapping GC/MS Components", Journal of the American Society for Mass Spectrometry, vol. 3, (1992), pp. 558-562.

Pool, Wim G., et al., "Automated Extraction of Pure Mass Spectra from Gas Chromatographic/Mass Spectrometric Data", Journal of Mass Spectrometry, vol. 32, (1997), pp. 438-443.

Dromey, R.G., et al., "Extraction of Mass Spectra Free of Background and Neighboring Component Contributions from Gas Chromatography/Mass Spectrometry Data", Analytical Chemistry, vol. 48, No. 9, (1976), pp. 1368-1375.

Jonsson, Paer, et al., "Extraction, Interpretation and Validation fo Information for Comparing Samples in Metabolic LC/MS Data Sets", The Royal Society of Chemistry, vol. 130, (2005), pp. 701-707.

Jonsson, Paer, et al., "A Strategy for Identifying Differences in Large Series of Metabolomic Samples Analyzed by GC/MS", Analytical Chemisty, vol. 76, No. 6, (2004), pp. 1738-1745.

Niessen, W.M.A., et al., "Liquid Chromatography-Mass Spectrometry General Principles and Instrumentation", Journal of Chromatography A, vol. 703, (199), pp. 37-57.

Hargrove, William F., et al, "Improvement of Algorithm for Peak Detection in Automatic Gas Chromatography-Mass Spectrometry Data Processing", vol. 53, (1981), pp. 538-539.

Herron, Nelson R., et al., "Software-Based Mass Spectral Enhancement to Remove Interferences from Spectra of Unknowns", American Society for Mass Spectrometry, vol. 7, pp. 598-604 (1996).

* cited by examiner

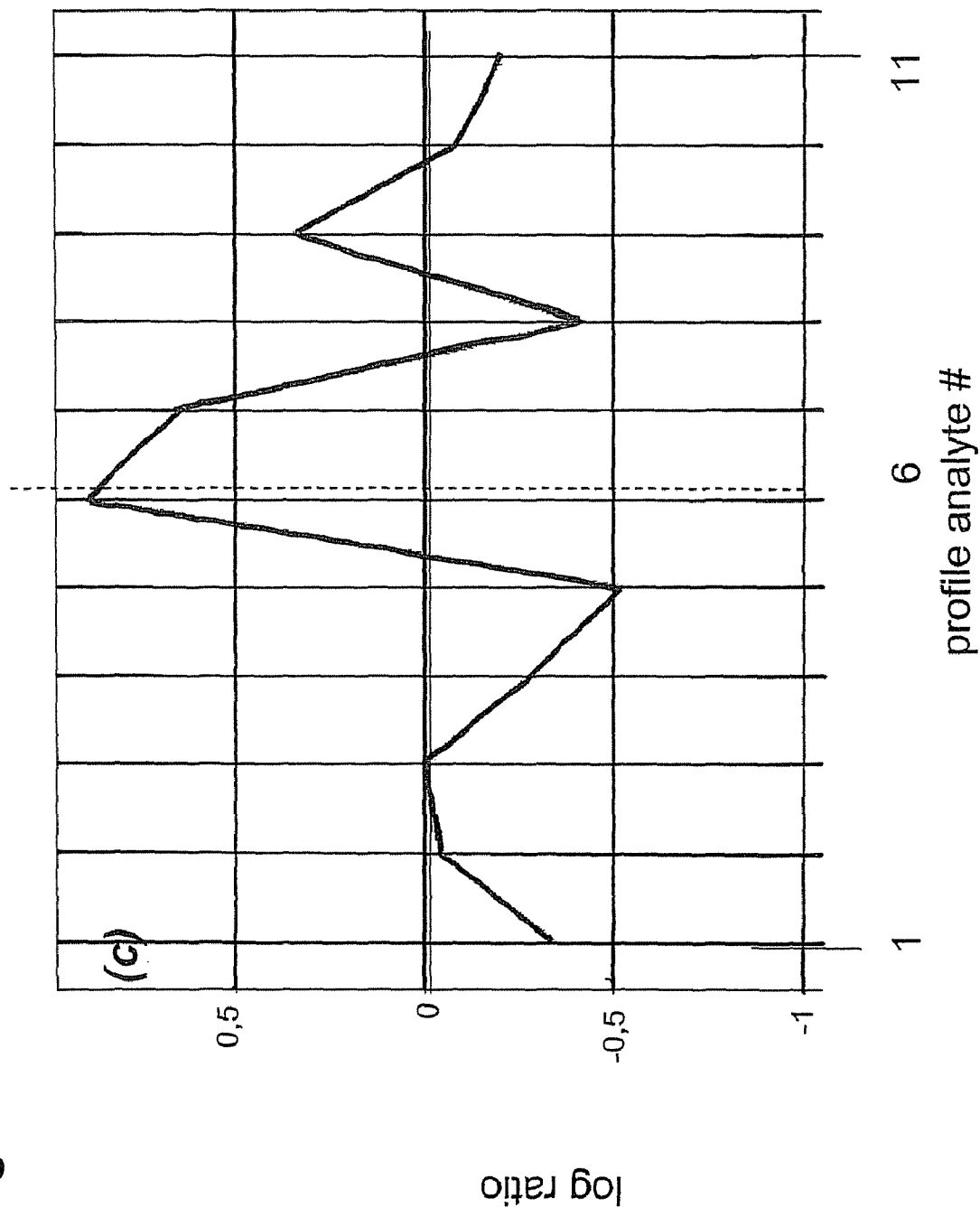

Fig. 6
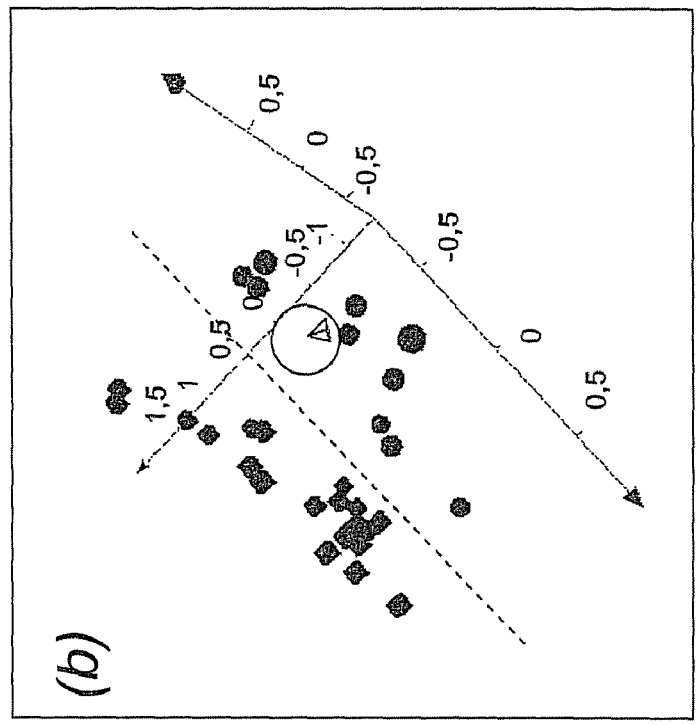
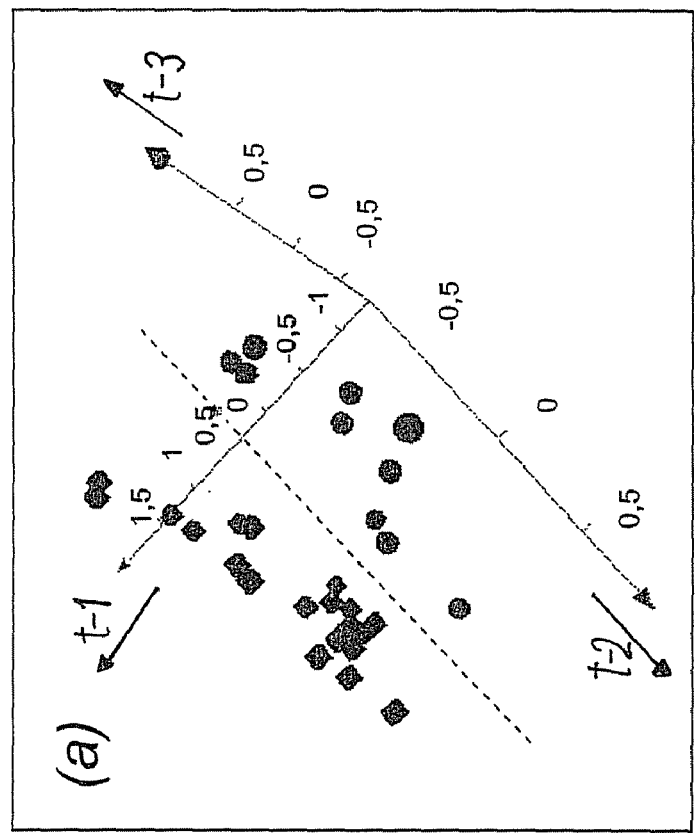

Fig. 8
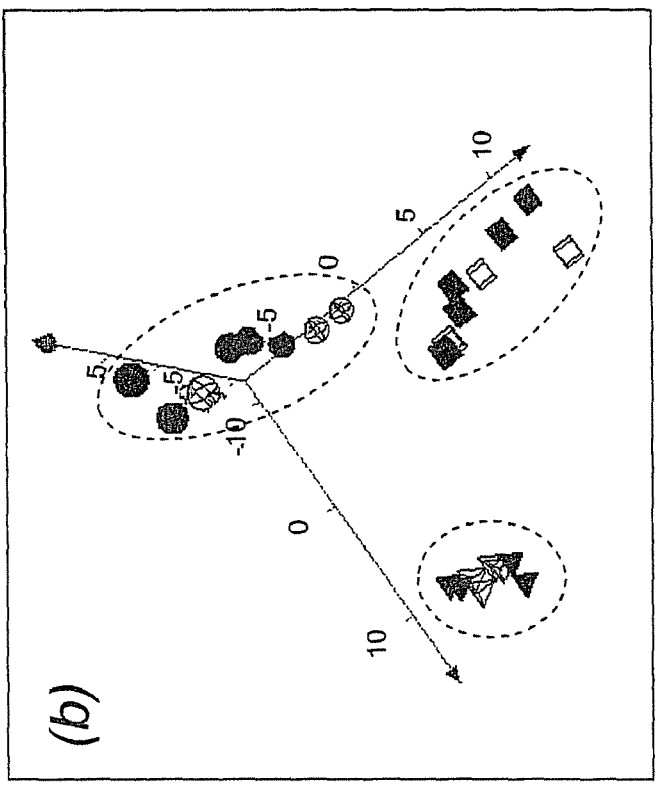
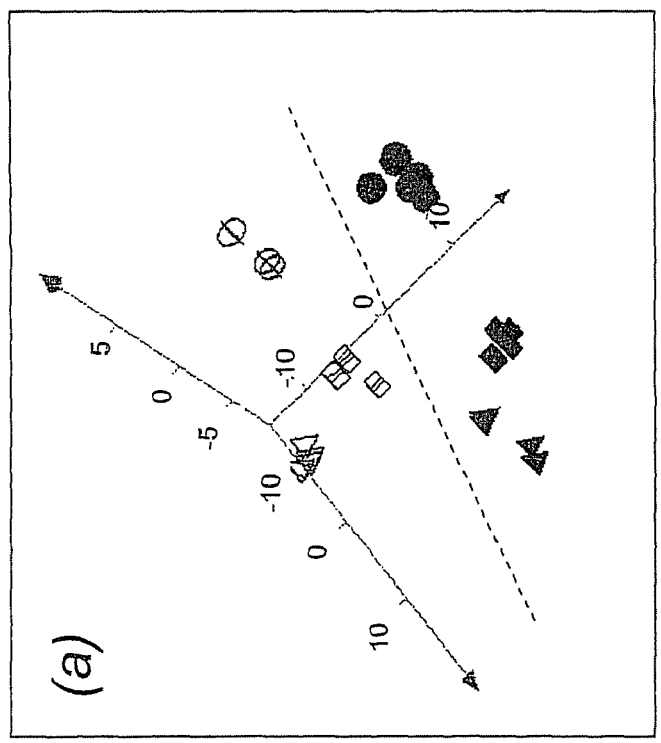

Fig. 10
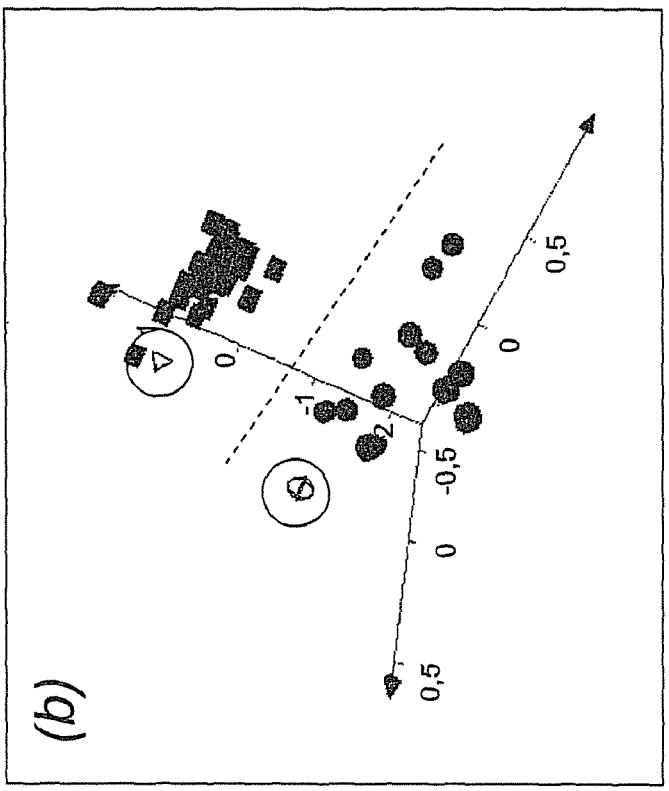
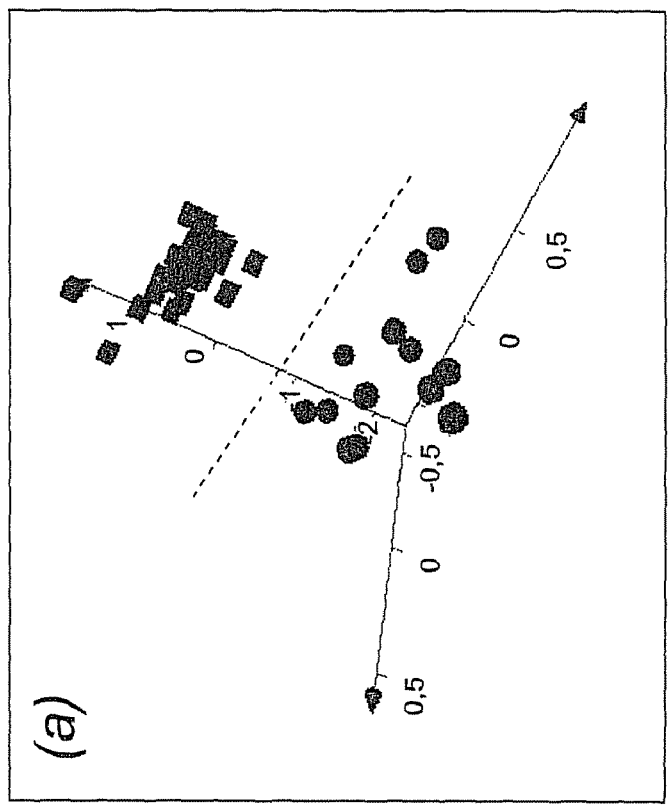

SYSTEM AND METHOD FOR ANALYZING A SAMPLE USING CHROMATOGRAPHY COUPLED MASS SPECTROMETRY

Priority is claimed as a national stage application under 35 U.S.C. §371 to PCT/EP2006/064628 filed Jun. 25, 2006, which claims benefit of European application 05016068.8, filed Jun. 25, 2005. The aforementioned priority documents are incorporated herein by reference as if set forth in full.

The present invention relates to a method for analyzing at least one test sample, wherein said test sample comprises at least one compound, said method comprising the steps of: a) providing at least one test sample comprising at least one compound; b) determining said at least one compound in said test sample whereby raw results are generated; and c) analyzing the raw results obtained in step b), wherein the analysis of said at least one test sample is accompanied by an analysis of at least one reference sample; and wherein the test sample and the reference sample are analyzed in an identical sequence in each step of the method. Moreover, the present invention further encompasses a system for carrying out said method comprising operatively linked to each other: (a) means for determining a compound; (b) means for monitoring process parameters, (c) means for analyzing raw results obtained from the means according to (a), wherein said means for analyzing raw results comprise: (i) a first database comprising raw results received from the means according to (a); (ii) a second database comprising monitored process parameters received from the means according to (b); (iii) a third database comprising rules for evaluating the raw results; and (iv) a fourth database comprising allocated results of identified compounds; wherein at least the second, third and fourth database are operatively linked to the first database.

State-of-the-art techniques of phenotype analysis of organisms comprise, inter alia, the analysis of the entire genome of an organism, called genomics, analysis of the entirety of the proteins, called proteomics, and the analysis of the entirety of RNA transcripts, called transcriptomics. More recently, these fundamental techniques of phenotypic analysis have been completed by the technique for analyzing the metabolome, the entirety of metabolites of an organism. This technique is called metabolomics or, sometimes, metabonomics. Metabolomics can be defined as the qualitative and quantitative determination of all low-molecular weight compounds (i.e. metabolites) in an organism or in an organ, tissue or cell thereof at a specific time and under specific environmental conditions. Accordingly, metabolomics can be also regarded as the study of the metabolic composition of biological material. Usually, samples of biological material are investigated, in particular urine, saliva or blood plasma. Metabolites are the products or intermediates of biochemical pathways and cellular mechanisms. The precise number of metabolites in many organisms is unknown. Estimates in, for example, humans range from about 2,000 to as many as 20,000 different metabolites. Of particular interest are the so-called small molecules, i.e. low-molecular weight compounds that serve as substrates, intermediates or products of the various metabolic biochemical pathways. Whereas genes and proteins mostly predetermine what happens in the cell, much of the actual biological activity happens at the metabolite level, including cell signalling, energy transfer, and cell to cell communication, all of which are also regulated by metabolites. Accordingly, although genes and proteins are closely linked to cellular mechanisms, metabolites even more closely reflect the actual cellular activities in response to endogenous factors, e.g., signalling between different cells, or exogenous factors, e.g., changes in environmental conditions. Thus, changes in the metabolome are the ultimate answer of an organism to genetic alterations, disease, or environmental influences. The metabolome is, therefore, most predictive for a phenotype. Consequently, the comprehensive and quantitative study of metabolites (i.e. metabolomics) is a desirable tool for studying various endogenous and exogenous effects on an organism's phenotype and, thus, complex biological issues relating to, e.g., disease development and progression or toxicity can be efficiently addressed. As mentioned before, an advantage of metabolomics is that the effects caused by exogenous factors can be immediately monitored by metabolic changes which usually appear much earlier than changes in the transcriptome, proteome or even the genome or epigenome of an organism, if any. Metabolomics allows the determination of effects of exogenous factors which do not influence the genome, transcriptome or proteome of an organism immediately. For instance, a toxic compound may be harmful for an organism but may not necessarily cause changes in the genome of said organism.

Various techniques have been described already for the analysis of complex mixtures of compounds such as the metabolome of an organism. These techniques include, for instance, mass spectroscopy, nuclear magnetic resonance (NMR), Fourier transform infrared (FT-IR) spectroscopy, and flame ionisation detection (FID), optionally coupled to chromatographic separation techniques such as liquid chromatography, gas chromatography or high performance liquid chromatography (HPLC).

However, metabolomics suffers from the high variability of the results generated by the methods. This variability is due to technical and biological variations. Technical variations are common to all analyzing devices. However, in the field of metabolomics this is a particular important issue since various analyzing devices, such as devices for extraction, chromatography and mass spectrometry are usually coupled with each other. Thereby, the variability caused by an individual device will be significantly enhanced for the overall method. Moreover, further technical variability will be caused by the analyzing tools which are applied to evaluate the data obtained by a metabolome analysis. These data are usually complex, high dimensional data sets which can be only evaluated after data processing, e.g., including dimensional reduction. Accordingly, due to the technical variability of the technique, many false positive or false negative results are produced. Further, the biological variability of the starting material used for metabolomics also influences the result. Specifically, in contrast to genomics or proteomics, the object to be investigated by metabolomics, i.e. the metabolome, is subject to rapid changes. These changes of the metabolome may even occur within a sample run of a metabolome analysis. For instance, degradation of less stable metabolites may occur. The resulting degradation products will, of course, influence the results. Moreover, if metabolomics is used for comparative phenotypic analysis, e.g. if a metabolome of a treated subject is to be compared with an untreated control, the starting material used for such an experiment will greatly predetermine the biological variability. The metabolome of different subjects, e.g., test animals, usually greatly differs within the physiological ranges. Thus, the animals appear to have a normal, comparable physiology although their individual metabolomes might differ. For comparative studies, the normally occurring metabolic differences, therefore, further contribute to the biological variability. Consequently, comparative metabolomics as used for toxicological assessments or drug efficacy studies is strongly influenced by variations originating from technical as well as biological sources. Accordingly, it is currently, in light of the many false positive and of false negative results, difficult to be sure that findings based on metabolomics are indeed valid. Nevertheless, it would be highly desirable to reliably apply metabolome analysis techniques for various emerging tasks including toxicological assessment, drug development, pharmacogenetics or diagnostics.

Moreover, besides metabolomics, there is a longstanding need for a reliable technique for analysis of complex mixtures of compounds, in general.

Accordingly, the technical problem underlying the present invention must be seen as the provision of means and methods for complying with the aforementioned needs, i.e. providing a reliable and efficient method for the analysis of a sample comprising at least one compound, preferably a plurality of compounds, such as metabolites in a biological sample. The technical problem is solved by the embodiments characterized in the claims and described herein below.

Accordingly, the present invention relates to a method for analyzing at least one test sample, wherein said test sample comprises at least one compound, said method comprising the steps of:
a) providing at least one test sample comprising at least one compound;
b) determining said at least one compound in said test sample whereby raw results are generated; and
c) analyzing the raw results obtained in step b), wherein the analysis of said at least one test sample is accompanied by an analysis of at least one reference sample; and wherein the test sample and the reference sample are analyzed in an identical sequence in each step of the method.

The expression "method for analyzing" means that the method of the present invention may be used for all analytical purposes. The method of the invention may essentially consist of the aforementioned steps or may include further steps. Moreover, it is further envisaged that the method of the present invention may be itself included into methods for different purposes such as screening methods, diagnostic methods or quality control methods. Preferred technical fields in which the method of the present invention can be applied are described in detail below.

The term "at least one compound" as used herein refers to a single compound or to a plurality of compounds, i.e. preferably at least 2, 3, 4, 5, 10, 50, 100, 500, 1,000, 2,000, 3,000, 5,000 or 10,000 compounds. It is to be understood that compound as used herein may be at least one molecule of said compound up to a plurality of molecules of the compound and that a plurality of compounds means a plurality of chemically different molecules wherein for each compound at least one molecule up to a plurality of molecules may be present. A compound in accordance with the present invention encompasses all classes of organic or inorganic chemical compounds including those being comprised by biological material such as organisms. Preferably, the compound in accordance with the present invention is a small molecule compound, more preferably a metabolite. More preferably, in case a plurality of compounds is envisaged, that the said plurality of compounds are metabolites being a metabolome.

The metabolites are small molecule compounds, such as substrates for enzymes of metabolic pathways, intermediates of such pathways or the products obtained by a metabolic pathway. Metabolic pathways are well known in the art and may vary between species. Preferably, said pathways include at least citric acid cycle, respiratory chain, photosynthesis, photorespiration, glycolysis, gluconeogenesis, hexose monophosphate pathway, oxidative pentose phosphate pathway, production and β-oxidation of fatty acids, urea cycle, amino acid biosynthesis pathways, protein degradation pathways such as proteasomal degradation, amino acid degrading pathways, biosynthesis or degradation of: lipids, polyketides (including e.g. flavonoids and isoflavonoids), isoprenoids (including eg. terpenes, sterols, steroids, carotenoids, xanthophylls), carbohydrates, phenylpropanoids and derivatives, alcaloids, benzenoids, indoles, indole-sulfur compounds, porphyrines, anthocyans, hormones, vitamins, cofactors such as prosthetic groups or electron carriers, lignin, glucosinolates, purines, pyrimidines, nucleosides, nucleotides and related molecules such as tRNAs, microRNAs (miRNA) or mRNAs. Accordingly, small molecule compound metabolites are preferably composed of the following classes of compounds: alcohols, alkanes, alkenes, alkines, aromatic compounds, ketones, aldehydes, carboxylic acids, esters, amines, imines, amides, cyanides, amino acids, peptides, thiols, thioesters, phosphate esters, sulfate esters, thioethers, sulfoxides, ethers, or combinations or derivatives of the aforementioned compounds. The small molecules among the metabolites may be primary metabolites which are required for normal all function, organ function or animal growth, development or health. Moreover, small molecule metabolites further comprise secondary metabolites having essential ecological function, e.g. metabolites which allow an organism to adapt to its environment. Furthermore, metabolites are not limited to said primary and secondary metabolites and further encompass artificial small molecule compounds. Said artificial small molecule compounds are derived from exogenously provided small molecules which are administered or taken up by an organism but are not primary or secondary metabolites as defined above. For instance, artificial small molecule compounds may be metabolic products obtained from drugs by metabolic pathways of the animal. Moreover, metabolites further include peptides, oligopeptides, polypeptides, oligonucleotides and polynucleotides, such as RNA or DNA. More preferably, a metabolite has a molecular weight of 50 Da (Dalton) to 30,000 Da, most preferably less than 30,000 Da, less than 20,000 Da, less than 15,000 Da, less than 10,000 Da, less than 8,000 Da, less than 7,000 Da, less than 6,000 Da, less than 5,000 Da, less than 4,000 Da, less than 3,000 Da, less than 2,000 Da, less than 1,000 Da, less than 500 Da, less than 300 Da, less than 200 Da, less than 100 Da. Preferably, a metabolite has, however, a molecular weight of at least 50 Da. Most preferably, a metabolite in accordance with the present invention has a molecular weight of 50 Da up to 1,500 Da.

The term "test sample" as used herein refers to samples to be analyzed by the method of the present invention. Said test sample shall be an artificial sample, a biological sample or an environmental sample. The test sample may be a liquid, solid, gaseous or supercritical sample.

An artificial sample is a sample which comprises or consists of at least one pre-selected compound (i.e. non-naturally occurring compound or naturally occurring compounds which have been separated from their natural environment and combined to an artificial sample). An artificial sample comprising a plurality of compounds may be obtained by simply mixing pre-selected compounds. Further, a sample may comprise compounds being obtained as the result of chemical reactions performed in vitro. Accordingly, the at least one compound in accordance with the present invention may be the product or a plurality of products obtained by a chemical reaction.

Moreover, samples comprising at least one compound may be obtained from biological or environmental sources. Usually, samples from biological sources (i.e. biological samples) comprise a plurality of compounds. They are, thus, complex samples which are difficult to analyze and to characterize. Biological samples are, preferably, derived from an organism. An organism as used herein encompasses animals (including humans), plants, bacteria, fungi and viruses. Samples of bacteria, viruses or fungi, preferably, are provided in form of cultures comprising them. How to provide and obtain such cultures is well known in the art. Samples may also include heterogeneous mixtures of organism like for example the microbiome, encompassing gut microbes, or the population of microorganisms living a certain environment, for example the saragossa sea. Samples from plants are, preferably, obtained from parts of the plants, such as their leaves, stems, roots or flowers, or from their seeds. However, the entire plants may be used as well. Samples from an animal include samples of body fluids, preferably, blood, plasma, serum, lymph, sudor, saliva, tears, sperm, vaginal fluid, feces, urine or cerebrospinal fluid, or samples derived, e.g., by biopsy, from cells, tissues or organs. This also encompasses samples comprising subcellular compartments or organelles, such as the Golgi apparatus or chloroplasts for plant cells. Moreover, biological samples also encompass gaseous samples, such as volatiles of an organism.

Moreover, a sample in accordance with the present invention further includes environmental samples. Environmental samples are obtained from any suitable place of nature or environment. They comprise, preferably, at least one compound present at said place of nature or environment. More preferably, environmental samples comprise a plurality of compounds found at said place, such as organic and inorganic compounds or organisms. Environmental samples, preferably, include geological samples, paleontological samples, water or wastewater samples or gaseous samples, such as air samples.

Most preferably, a sample in accordance with the present invention is a biological sample as defined above.

The aforementioned samples are, preferably, pre-treated before they are characterized by the method of the present invention. As described in more detail below, said pre-treatment may include treatments required to release or separate the compounds or to remove excessive material or waste. Suitable techniques comprise extraction, fractioning, purification and/or enrichment of compounds. Moreover, other pre-treatments are carried out in order to provide the compounds in a form or concentration suitable for compound analysis. For example, if gas-chromatography coupled mass spectrometry is used in the method of the present invention, it will be required to derivatize the compounds prior to (the) said gas chromatography. Suitable and necessary pre-treatments depend on the means used for carrying out the method of the invention and are well known to the person skilled in the art. Pre-treated samples as described before are also comprised by the term "sample" as used in accordance with the present invention.

The term "providing" as used herein means that the at least one test sample is provided in a manner suitable for determining the at least one compound comprised by said test sample. Accordingly, providing as used herein also refers to carrying out suitable pre-treatments comprising those specifically mentioned in this specification, i.e. most preferably concentration or fractioning of the sample and/or extraction of the sample. Depending on the technique which is used to determine the at least one compound in the test sample, additional pre-treatments may be required. Such pre-treatments encompass hydrolysis of proteins or derivatization of the at least one compound present in the sample prior to gas chromatography as mentioned before already and described in detail below.

The term "determining said at least one compound" as used herein refers to determining at least one characteristic feature of the at least one compound comprised by the sample referred to herein. Characteristic features in accordance with the present invention are features which characterize the physical and/or chemical properties including biochemical properties of a compound. Such properties include, e.g., molecular weight, viscosity, density, electrical charge, spin, optical activity, colour, fluorescence, chemoluminescence, elementary composition, chemical structure, capability to react with other compounds, capability to elicit a response in a biological read out system (e.g., induction of a reporter gene) and the like. Values for said properties may serve as characteristic features and can be determined by techniques well known in the art. Moreover, the characteristic feature may be any feature which is derived from the values of the physical and/or chemical properties of a compound by standard operations, e.g. mathematical calculations such as multiplication, division or logarithmic calculus. Preferably, ratios may be calculated. Most preferably, a characteristic feature to be determined in accordance with the present invention is the molecular weight and/or charge of a compound. A most preferred characteristic feature which is derived there from is the mass to charge ratio (m/z). It is to be understood that determining at least one compound also encompasses determining of all compounds present in a sample as referred to in accordance with the present invention.

The at least one compound comprised by a test sample may be determined in accordance with the present invention quantitatively or qualitatively. For qualitative determination, the presence or absence of the compound will be determined by a suitable technique. Moreover, qualitative determination may, preferably, include determination of the chemical structure or composition of the compound. For quantitative determination, either the precise amount of the at least one compound present in the sample will be determined or the relative amount of the at least one compound will be determined. The relative amount may be determined in a case were the precise amount of a compound can or shall not be determined. In said case, it can be determined whether the amount in which the compound is present is enlarged or diminished with respect to a second sample comprising said compound in a second amount. Quantitatively analysing a compound, thus, also includes what is sometimes referred to as semi-quantitative analysis of a compound.

Moreover, determining as used in the method according to the present invention, preferably, includes using a compound separation step prior to the compound analysis step referred to before. Preferably, said compound separation step yields a time resolved separation of compounds. Suitable techniques for separation to be used preferably in accordance with the present invention, therefore, include all chromatographic separation techniques such as liquid chromatography (LC), high performance liquid chromatography (HPLC), gas chromatography (GC), thin layer chromatography, size exclusion or affinity chromatography. These techniques are well known in the art and can be applied by the person skilled in the art without further ado. Most preferably, LC and/or GC are chromatographic techniques to be envisaged by the method of the present invention.

Suitable devices for such determination of compounds are well known in the art. Preferably, mass spectrometry is used in particular gas chromatography mass spectrometry (GC-MS), liquid chromatography mass spectrometry (LC-MS), direct infusion mass spectrometry or Fourier transform ion-cyclotrone-resonance mass spectrometry (FT-ICR-MS), capillary electrophoresis mass spectrometry (CE-MS), high-performance liquid chromatography coupled mass spectrometry (HPLC-MS), quadrupole mass spectrometry, any sequentially coupled mass spectrometry, such as MS-MS or MS-MS-MS, inductively coupled plasma mass spectrometry (ICP-MS), pyrolysis mass spectrometry (Py-MS), ion mobility mass spectrometry or time of flight mass spectrometry (TOF). Most preferably, LC-MS and/or GC-MS are used as described in detail below. Said techniques are disclosed in, e.g., Nissen, Journal of Chromatography A, 703, 1995: 37-57, U.S. Pat. No. 4,540,884 or U.S. Pat. No. 5,397,894, the disclosure content of which is hereby incorporated by reference. As an alternative or in addition to mass spectrometry techniques the following techniques may be used for compound determination: nuclear magnetic resonance (NMR), magnetic resonance imaging (MRI), Fourier transform infrared analysis (FT-IR), ultra violet (UV) spectroscopy, refraction index (RI), fluorescent detection, radiochemical detection, electrochemical detection, light scattering (LS), dispersive Raman spectroscopy or flame ionisation detection (FID). These techniques are well known to the person skilled in the art and can be applied without further ado.

It is envisaged that the characteristic feature(s) for a compound determined in accordance with the present invention can be represented by at least two different variables, whereby at least one of said variables is an intensity variable. An intensity variable may be any variable which reflects a measured signal intensity. The signal intensity, preferably, directly or indirectly correlates with the abundance of a compound. The other variable(s) are variable(s) which depend on a characteristic feature of a compound, in a preferred embodiment, a time variable and a mass variable. In a preferred embodiment of the method of the present invention, a time resolved separation technique will be coupled to a mass resolved separation technique, such as GC-MS and/or LC-MS. The time resolved separation technique generates a signal intensity as a function of time. In case a chromatography is used, as preferably envisaged in accordance with the present invention, the time variable is preferably the retention time. Nevertheless, the expression "time variable" may be generalized to basically any variable indicating a progress of the experiment or the measurement. Thus, e.g., the expression "time variable" may as well include a position variable, which may be transformed into a process time by using a characteristic velocity. Thus, e.g., when using a chromatographic column, the position of a certain compound (indicated, e.g., by a specific coloration within the column) may be transformed into a time, such as by comparing the position of the compound to the position of a solvent within the column, which is dependent on the velocity of the solvent within the column. Other types of "time variables" indicating a progress of the experiment or the measurement are feasible and shall be included, such as a number of cycles of a process of known periodicity. Similarly to the expression "time variable", the expression "mass variable" shall not be restricted to a mass, and, may comprise, e.g., a mass-to-charge-ratio m/z and/or other variables being derived from a mass.

Determining as used herein further comprises processing of the primary raw data into raw results. If for instance mass spectrometry is used as method for determination, primary raw data are generated by, for instance, secondary electron multipliers which measure ion impacts. The subsequently generated voltage signal will then be transformed into raw results based on the intensity value of said signal and a mass-related value, such as position of impact (channel position), mass filter settings or time until impact. Said processing of the primary raw data can be done by techniques well known in the art. In case of NMR, IR, UV or other spectroscopy techniques, adsorption of electromagnetic radiation will be measured. Depending on the method, scintillation devices, semiconductors, photo cells, thermo-sensors or photomultipliers will be used to determine the adsorption. Again, a voltage based secondary signal is produced as primary raw data. As described before, said primary raw data can be processed into raw results by techniques well known in the art.

The term "raw results" refers to processed primary raw data as described above. Raw results preferably comprise at least one data point characterized by at least two variables as referred to above. Preferably, if mass spectrometry is used, the data point is characterized by a mass variable and an intensity variable. It is to be understood further that a compound may produce more than one data point in the raw results. If mass spectrometry is used, data points may result in peaks in the raw results. Accordingly, if in a preferred embodiment of the present invention LC-MS and/or GC-MS is used for compound determination, the primary raw data are processed into a three dimensional format. Said format has a time variable range, a mass variable range and an intensity variable range. The format contains data points corresponding to the measured primary raw data. The entirety of the data points of the primary raw data will build up a three dimensional landscape comprising maxima (i.e. peaks) and minima (i.e. zero level data points for the intensity variable). It is to be understood that the raw results may be also presented by other suitable formats such as data sheets.

Means and methods for processing of the primary raw data are well known in the art. For example, in case of chromatography coupled to mass spectrometry, computer programs for processing are commercially available, such as ChemStation (Agilent Technologies, USA), Analyst (MDS SCIEX, Canada) or AMDIS (NIST, USA). Moreover, processing of the primary raw data may further require creating coherent data by converting the primary raw data in a numeric format, converting the data into a common unit format and/or dimensionally reducing the data. Suitable means and methods for creating such coherent data are disclosed in WO 03/046798, the disclosure of which is hereby incorporated by reference.

The term "reference sample" refers to a sample comprising at least one reference compound. Said reference compound is in one aspect of the present invention a pre-selected compound in a pre-selected amount or a mixture of such pre-selected compounds. In another, preferred, aspect, the reference sample is a mixture of various compounds. If a sample comprising biological material is to be investigated as described herein before, it is envisaged that a sample of biological material will also serve as a reference sample. The reference sample is suitable for normalizing the raw results generated by the method of the present invention with respect to technical variability and/or biological variability. This can be achieved by comparing different analyses performed for the same reference sample (i.e. analyses which theoretically should yield the same results) as described in detail below.

To this end, it has been found in accordance with the present invention that it is advantageous to use a reference sample having an essentially identical composition for at least a series of analyses (i.e. analyses of at least two test samples) carried out with the method of the present invention. A series of analyses may be carried out, for example, for a comparative study. In such a study, preferably, at least one first test sample is analyzed and the results obtained by said analysis will be compared to the results of an analysis of at least one second test sample. The reference sample in that case may be distributed to various aliquots. An aliquot of the reference sample, thus, may serve as reference sample for each analysis of the series. It is to be understood that the aliquots are stored under conditions which do not permit changes to the composition of the aliquots. For example, aliquots of biological samples as reference samples may be stored, preferably, in an inert atmosphere in, e.g., liquid nitrogen or at least at a temperature of −80° C. In case a single analysis of a test sample is to be carried out, it is envisaged that a reference sample is used which has been analyzed already before, i.e. whose raw results from the previous analysis are available. More than one reference sample may be used in the method of the present invention. Moreover, the same reference sample (e.g. different aliquots of one reference sample) is, preferably, included more than once, more preferably, three to ten times, in a sequence as described below. Preferably, at least three different reference samples are to be used. Preferred reference samples are described in detail below. Moreover, further reference samples may be included for specific steps of the method of the present invention in addition to the aforementioned reference samples to be used for the entire steps.

The term "sequence" as used in accordance with the present invention refers to a collection of samples to be analyzed together. Preferably, the test samples and the reference sample are subjected to the method of the present invention consecutively, i.e. using the same devices in separate sample runs within the same analysis. More preferably, a sequence comprises at least one test sample and at least one reference sample, most preferably, at least one test sample and at least two reference samples. The sequence order may be randomized or pre-selected. The same randomized or pre-selected sequence order may be obeyed for all steps, or a new sequence order may be determined for each step of the method.

The term "analyzing" as used herein refers to validation and/or evaluation of the raw results generated by the method of the present invention. Depending on the specific purpose of the method, the term may include further steps. Preferred embodiments of the method of the present invention which include said further steps are specified elsewhere in this specification.

Validation as used herein encompasses confirming or invalidating raw results in light of process parameters which have been monitored during analysis, i.e. during the sample run. For example, if the monitored process parameters indicate technical inconsistencies (e.g., voltage or current variations in electrical apparatuses or altered flow rates or altered recovery rates for standards during chromatography) of a certain analytical device which is used to carry out the method of the present invention, the raw results obtained for said sample run shall be invalidated and, thus, not considered further for the evaluation. Moreover, validation encompasses subjecting each peak or signal of the raw results to a validation algorithm. Such an algorithm, for instance, may compare the characteristics of a peak or signal with corresponding characteristics of a reference peak or signal or a hypothetical optimized peak or signal. When the characteristics of a peak or signal comprised by the raw results significantly differ from the corresponding characteristics of the reference, the said peak or signal will be invalidated for evaluation, too. Suitable algorithms take into account, e.g., the relative retention time indices, the peak geometry, fortification results obtained with standard matrices, fortification results for pre-selected compounds and/or calibration with respect to external standards as will be described in detail below.

Analyzing as used herein also, preferably, encompasses the evaluation of the raw results which have been validated. Evaluation encompasses normalization of the validated results with respect to validated results (i.e. the results of the actual analysis and the results of a previous analysis for the same reference sample) obtained from the reference samples as will be described in detail below. The normalization step and the validation may be carried out in vice versa order and/or done repetitively. Preferably, validation is carried out prior to the normalization.

Moreover, evaluation includes all techniques which allow drawing conclusions based on the validated results with respect to the presence or absence of at least one specific compound or its chemical nature (qualitative analysis) or the precise or relative amount of the at least one compound (quantitative analysis). Moreover, the conclusion, preferably, encompasses a conclusion as to the degree of identity of the compounds or amounts thereof in different samples. In a preferred aspect, evaluation, thus, also encompasses comparing validated results of different samples. Most preferably, said comparing comprises assessing whether the samples are different or identical to each other (i.e. the degree of similarity is determined). In principle, any statistical test which allows determining whether compounds or characteristic features thereof or amounts thereof will vary significantly between different samples is suitable for carrying out the aforementioned comparison. More preferably, suitable techniques include a pattern recognition algorithm and/or a statistical test algorithm and/or a multivariate algorithm eg. Principal Component Analysis (PCA), Simple Component Analysis (SCA), Independent Component Analysis (ICA), Principal Component Regression (PCR), Partial Least Squares (PLS), PLS Discriminant Analysis (PLS-DA), Support Vector Machines (SVM), Neural Networks, Bayesian Networks, Bayesian Learning Networks, Mutual Information, Backpropagation Networks, symmetrical Feed-Forward Networks, Self-Organizing Maps (SOMs), Genetic Algorithms, Hierarchical or K-Mean Clustering, Anova, Student's t-Test, Kruskal-Wallis Test, Mann-Whitney Test, Tukey-Kramer Test or Hsu's Best Test. Preferably, the comparison of samples as described above can be applied to determine differences or similarities between samples with respect to their qualitative or quantitative composition. Determining of similarities may, preferably, also encompass determining of mean or median values for the abundance of compounds. Comparison as used herein will, in the latter case, preferably also comprise comparing the means or medians of two pluralities of samples suspected to differ in their compositions. Evaluation as used in accordance with the present invention is preferably assisted by automation, e.g. by a suitable computer program for at least one of the aforementioned algorithms on a computer.

The following particularly preferred algorithms for evaluation are, preferably, in whole or partially, carried out by a computer program containing instructions which allow for evaluation when implemented and carried out by a computer and/or a computer network or a similar data processing device.

Preferably, comparing as carried out in the context of the evaluation of the validated results comprises classifying the said validated results in terms of similarity/dissimilarity to the reference set. Thus, preferably, an algorithm is used, which may be named "the MisMatch Match (MMM) approach". In this method, the step of analyzing comprises a step of correlating at least two vectors, wherein at least one of the at least two vectors is subjected to a shrinkage process for the components of the vector, taking into account the reliability of the component.

In the preferred embodiment of "the MMM method", this algorithm includes the following steps:

Each group of samples (e.g., test samples which have been treated with a certain compound suspected to elicit a metabolic change relative to untreated control samples) is characterized by a vector of contrasts $X=X_1, X_2, X_3 \ldots X_i$, where i indexes individual metabolites and $X_i$ corresponds to the validated results for the individual metabolites in each sample group. Typically, X represents a median or mean contrast calculated from the median or mean of the test group (T) and the median or mean of the control group (C), that is $X_i=\text{Median}(T_i)-\text{Median}(C_i)$ or $X_i=\text{Mean}(T_i)-\text{Mean}(C_i)$. Thus, e.g., a positive value of $X_i$ may indicate an increase in metabolite concentration, whereas a negative value of $X_i$ indicates a decrease.

The aim of the method may be, e.g., to identify a reference profile, characterized by a vector of contrasts $Y=Y_1, Y_2, Y_3, \ldots Y_i$, matching the test profile, or, alternatively or additionally, to identify differences between the said profiles. Conventional methods known to the person skilled in the art, are based on correlation methods, such as the Pearson correlation method, the Spearman correlation or the Kendall correlation method. Thus, e.g. a comparison of profiles according to the Pearson correlation may use the following algorithm in order to identify a reference profile Y matching the test profile X:

$$\max_y (\text{corr}(X, Y)) = \max_y \Sigma_i [(X_i - <X>)(Y_i - <Y>)/$$
$$(sd(X)sd(Y))]$$
$$\approx \max_y \Sigma_i [X_i Y_i / (|X||Y|)]$$
$$= \max_y (\Sigma_i [X_i Y_i / (|X||Y|)] - +$$
$$\Sigma_i [X_i Y_i / (|X||Y|)] +),$$

with standard deviations "sd", [x]− equals x if x<0 and zero otherwise, [x]+ equals x if x>0 and zero otherwise, and assuming $<X>\approx 0$, $<Y>\approx 0$ for log ratios.

In the latter term, the first sum indicates the (negative) score of "mismatches", i.e. the sum of negative products of the individual components of the profiles X and Y, and, thus, a quantification of the differences in the metabolic profiles:

Mismatch=$-\Sigma[X_i Y_i/(|X||Y|)]->0$.

The second sum indicates the score of "matches", i.e. the sum of positive products of the individual components of the profiles X and Y and, thus, represents a quantification of the similarities in the metabolic profiles:

Match=$\Sigma_i [X_i Y_i/(|X||Y|)]+>0$.

These known correlation methods, however, by indifferently summing over Matches and Mismatches, disregard the information separately provided by the score of matches and the score of mismatches.

According to "the MMM method" to be carried out in accordance with the present invention, this additional information is taken into account. It can be shown mathematically that a separate evaluation of the Matches and Mismatches contributes to a higher degree of reliability of the predictions, since, e.g., in many cases the information provided by the score of mismatches is larger for the determination of differences or similarities than the information provided by the score of matches.

According to the MMM method, the content of information within the score of matches and the score of mismatches is further emphasized by a step called "shrinkage". Therefore, in addition to the contrast vector X, a second vector of probabilities P of the same dimension as the contrast vector X is calculated, that is $P=P_1, P_2, P_3 \ldots P_i$. P is a vector of sufficient statistics derived from testing the test group or treatment population $(T_i)$ against the control population $(C_i)$ by an appropriate statistical two sample test such as t-, Welch- and Wilcoxon-test etc. Informally, $P_i$ measures the likelihood that the corresponding contrast $X_i$ is a chance find, and, thus, the reliability (experimental and/or statistical) of the contrast $X_i$.

Next, the two vectors X and P are aligned and P is compared element-wise with a predefined probability value, $\alpha$. If the probability $P_k$ is found to be larger than $\alpha$ then the corresponding contrast $X_k$ is set to zero (i.e. "shrunken", hence the name of the method). It is to be understood that prior to shrinkage the probability level $\alpha$ has to be defined. Preferably, values $\alpha=0.05$, $\alpha=0.10$, or $\alpha=0.01$ (5%, 10%, and 1% test level respectively) are recommended but larger or smaller values might be reasonable, too, depending on the problem at hand. Alternatively, individual probabilities $\alpha_k$ may be used for each vector component. This procedure (the so-called "shrinkage") ensures that small and insignificant changes do not contribute to the mismatch-match statistics (see below). Statistically, shrinkage greatly reduces variance/bias of the mismatch-match scores. Thus, carrying out the aforementioned shrinkage step on data obtained from biological samples will e.g. reduce the negative influence from biological variability between the subjects to be investigated. All remaining significant values X with |X|>0 are either left unchanged or discretized. Discretization can be, preferably, carried out by ternary coding, i.e. by setting all positive values to one and all negative values to minus one. Discretization may also include more than the three levels −minus one, zero, and one, e.g. additional levels minus two and two for highly significant X values.

In a further step, a mismatch-match scoring, similar to the "conventional" correlation methods as outlined above, is carried out, in order to assess the similarity/dissimilarity of two shrunken profiles, say X' and Y', wherein X' is the shrunken test profile and Y' is the shrunken profile of the reference profile Y mentioned above. The two vectors X', Y' are aligned, multiplied component-wise and normalized to unit length, that is $$Z'=(X'_1*Y'_1, X'_2*Y'_2, X'_3*Y'_3 \ldots X'_i*Y'_i)/(|X'|*|Y'|)$$

with |X'|, |Y'| being Euclidian norms respectively, $$|X'|=\text{sqrt}(X'_1*X'_1+X'_2*X'_2+X'_3*X'_3+\ldots X'_i*X'_i)$$
$$|Y'|=\text{sqrt}(Y'_1*Y'_1+Y'_2*Y'_2+Y'_3*Y'_3+\ldots Y'_i*Y'_i)$$

with "sqrt" denoting square root and "*" denoting multiplication.

Alternatively, a non-normalized Z' may be used, i.e. $Z'=(X'_1*Y'_1, X'_2*Y'_2, X'_3*Y'_3 \ldots X'_i*Y'_i)$. The formula for non-normalized Z' can be derived analogously to the formula for normalized Z' starting with maximum covariance instead of maximum correlation.

Next, the positive and negative components of Z' are summarized separately, thereby defining the two scores, i.e. the score of matches and the score of mismatches:

Match=$\Sigma_k [Z'_k]+$

Mismatch=$-\Sigma_k [Z'_k]-$

It can be shown that under shrinkage the mismatch scores are much more informative than the match scores. In this way a prescription is provided for judging the two scores. According to that prescription, similar profiles are minimizing Mismatch and maximizing Match. Thus, by taking into account the separate information provided by the scores "Match" and "Mismatch", the MMM method allows for reliable and efficient evaluation and/or classification of metabolic profiles.

In a more preferred embodiment of the method of the present invention, the MMM method may be used in order to compare a profile to a reference set encompassing many profiles by using the algorithm specified herein above. To this end, the following steps are carried out:

First, the steps described above are applied to the desired number of reference profiles (N=number of reference profiles) yielding N pairs of scores.

Then, these scoring data can be processed by one or more of the following steps:

1.) The N pairs of scores are sorted first in increasing order by score "Mismatch" and then in decreasing order by score "match". This sorting will put candidates with minimal mismatch scores and maximal match scores on top of the list. This approach is especially suitable for discretized profiles. Candidates from the reference set similar to the target can be found on top of this sorted list;

2.) In addition to sorting the scores it is recommended that the mismatch-match scores are plotted as this will provide valuable information about degenerated pairs, alternative candidates etc. This can be easily achieved by plotting the mismatch scores versus the match scores using appropriate plot labels for uniquely identifying the reference profiles (e.g. using numbers, colour coding or 'drill down' functionalities). If detection of similarities is the aim then promising candidates can be found at the lower and upper margins of the bivariate Mismatch, Match-distribution; or 3.) In addition to sorting scores hierarchically as described in 1.) above, the scores of mismatches and matches may be combined by a weighted sum incorporating the different information content of mismatches and matches or other methods of scoring data well known to the person skilled in the art.

It has been found in accordance with the present invention that the aforementioned computer-implemented algorithm is, advantageously, able to tolerate a moderate number of missing values and, thus, specifically useful for comparison of biological data in automated high-throughput screening assays. Also, exceptionally high numbers of missing values can be handled by additional normalization to the number of non-missing values. Another strength of the MMM approach lies in the discovery of new classes not yet included in the reference: such scenarios reveal characteristic mismatch to match distributions. Finally, a particular strength of the MMM approach lies in its capacity to reduce difficult multi-class classification tasks to simpler classification tasks with considerably less classes. Here, the combination of the MMM approach with other classification methods, especially with the SICI approach described below, is especially fruitful.

Preferably, evaluation may alternatively or in addition include the "Select, Iteratively Classify and Integrate Approach (SICI Approach)". Preferably, this algorithm is capable of carrying out the following steps:

1. Split Dataset:

A dataset may comprise data from different origins, experiments etc. Those data (i.e. validated results) may also differ from each other. In order to improve the evaluation, an inhomogeneous dataset consisting of results from strikingly different groups of samples or subjects, is, preferably, split into two or more homogenous groups, e.g. a male or a female group or groups of different populations of laboratory animals. It is to be understood that splitting is only required if the validated results of strikingly different groups of samples or subjects are stored in a common database. The need of splitting is, preferably, detected by unsupervised analysis methods. Unsupervised methods may be principal component analysis (PCA), nonlinear PCA, Independent Component Analysis (ICA), Self-organized Maps (SOM), metric and/or non-metric forms of multi-dimensional scaling, Sammon's Mapping.

2. Select Analytes

After the optional step of splitting of the dataset, a step of selecting analytes (e.g. metabolites) is performed. To this end, each sub-dataset is restricted to "significant analytes" (i.e. significant validated results) only. In order to define the significant analytes, all analytes are compared between samples suspected to differ from each other by applying statistical tests, e.g. student's t-test, Welch test, Wilcoxon test (each test either paired or unpaired). Samples suspected to differ from each other are, preferably, test samples such as treatment groups and control samples, e.g. of the same clinical study, of the same center and clinical study, of the same animal study, of the same center and animal study, of the same measurement series, etc., or other groups to be compared as set forth in this specification. To each analyte, a characteristic p-value (probability value) of all the p-values obtained for that analyte in any conducted group comparison test is assigned (usually several group comparisons are conducted), e.g. its minimum, median, or mean p-value. Significant analytes are defined as analytes having a p-value below a given threshold alpha (wherein alpha is a value between zero and one, wherein alpha=one corresponds to the selection of all analytes). Thus, alpha may correspond to the so-called "false discovery rate" (FDR), e.g. alpha equal to 0.10 corresponding to a FDR of ten percent, alpha equal to 0.05 corresponding to a FDR of five percent, and alpha equal to 0.01 corresponding to a FDR of one percent.

3. Classify Individual Samples or a Group of Related Samples Thereof.

After the selection of significant analytes, a step of classifying the individual samples or the individual groups of related samples comprising the said significant analytes is performed. To this end, the selected significant analytes are compared to a reference on the basis of a classification model generated on the set of references with known class membership constituting the training data. Depending on the degree of similarity, a test sample is allocated to a class defined by the reference with a certain probability (i.e. the class probability). Classifying can be implemented by well-established classification model algorithms, e.g. Prediction Analysis of Microarrays (PAM, see e.g. Tibshirani, Hastie, Narasimhan and Chu (2002): "Diagnosis of multiple cancer types by shrunken centroids of gene expression", Proc. Natl. Acad. Sci. 2002 99:6567-6572), Linear Discriminant Analysis (LDA), diagonal LDA, Support Vector Machines (SVM), decision trees. References may be in this context panels or profiles consisting of significant analytes comprised by samples for which the allocation to a certain class is known. Depending on the type of classification, the person skilled in the art is well aware of how to obtain a suitable assignment of test samples to the reference. Moreover, it is to be understood that besides single test samples, groups of test samples may be classified together if they belong to the same biological entity. A biological entity may be a subject. In such a case, samples taken from said subject at different time points may be classified, nevertheless, together as a group of test samples. A "group of related samples" as used herein may be represented by a single set of validated results obtained from different samples of the same subject, e.g., in the context of time course experiments, or may be represented by individual sets of validated results corresponding to individual samples. The classification of the aforementioned single samples or a group of samples are referred herein below as "single case classification".

Die Zeilen 19-28 geben 2 Textversionen wieder, wahrscheinlich sollten wir uns für eine entscheiden?

4. Integrate Single Case Classification Results to Group Results

The single case classification may be ambiguous on group level. In order to create an unambiguous classification result for the entire group of test samples (i.e. also for the unrelated test samples), e.g. experimental (treatment) repetitions, the single case classification results shall be integrated. This is, preferably, done by applying specific integration rules to the single case classifications. Specific integration rules may classify the entire group of test samples based on the class of the majority of single case classifications (majority voting) or may classify the entire group of test samples according to a maximum likelihood or trimmed maximum likelihood if outlier cases are to some degree expected.

5. Integrate Sub-Dataset Results

In a further preferred step, the classification results for different homogenous groups may be integrated further in order to obtain a common result for the inhomogeneous parent group, if any. For example, results for the homogeneous group of males and the homogeneous group of females may be integrated to obtain results for the parent, inhomogenous group of all subjects of an analyzed population. This can be done either on the level of biological/biochemical interpretation, e.g. applying systems biology techniques, or alternatively, by mathematics by summing votings or likelihoods, possibly incorporating weights characterizing the degree of reliability or relevance of sub-dataset results.

6. Generate Classification Profiles

Further, preferably, an optional step of generating classification profiles is performed. Preferably, the step shall be applied where a limited number of group test samples is available for classification and where the number of classes to which the single cases can be allocated is high, at least 3 classes, preferably, exceeding 10 classes, more preferably, exceeding 100. Classification profiles are, preferably, obtained by the following procedure of iterative reclassification:

First, a classifier is generated using the entire reference (e.g. training data) and applied for a first class prediction of a specific (treatment) group.

Then, all cases of the predicted class are eliminated from the said reference, another classifier is generated on the remaining reference and applied for a second class prediction.

Then, all cases of the second predicted class are additionally eliminated from the said reference, another classifier is generated for a further class prediction, etc.

The procedure is continued until all classes are removed from reference or until a classification profile possesses sufficient length.

All class predictions of a specific (treatment) group form a "classification profile": a list of ordered class predictions with corresponding stepwise class probability, e.g. maximum log likelihood, and class assignment distinctiveness, e.g. distance of maximum log likelihood to second maximum log likelihood. Preferably, the length of a classification profile equals the number of classes for references, but shorter profiles may also suffice depending on the field of application or the structure of the generated profile.

It is to be understood that although developed for metabolomic profiling the aforementioned techniques for evaluation are equally applicable to the profiling of other multi-dimensional data which may be obtained from microarrays, mass spectrometry or NMR analyses carried out for, e.g., transcriptional or proteomic profiling.

Furthermore, analyzing also, preferably, includes generating a specific profile (i.e. a fingerprint) for a certain sample based on the raw results or the validated raw results. Such a specific profile is based on raw results derived from at least one characteristic feature of the sample in its entirety. Where a sample comprises a plurality of different compounds, the profile will not necessarily include raw results from all characteristic features for all compounds. Preferably, it is envisaged to include the most informative raw results into the specific profile. Moreover, the raw results may be processed and informative processed raw results will be included into the profile. Preferred techniques for generating a specific profile in accordance with the present invention are disclosed in detail below.

The method of the present invention is, in principle, suitable for the analysis of various types of test samples, including biological, artificial and environmental samples.

As discussed above, the method of the present invention is, more preferably, applied for analysing the metabolome of an organism based on a biological sample derived there from. Accordingly, the method of the present invention includes in a preferred embodiment a method for analyzing the metabolome of an organism based on a sample obtained there from using the steps, in principle, described before and described in more detail below.

In a first step, a sample derived from biological material such as blood plasma or urine will be provided. The sample will be accompanied during all steps of the method by at least one reference sample. In the case of blood plasma, a reference sample may be an aliquot of previously analyzed sample, i.e. it is important that raw results of the said sample already exist in order to evaluate the technical variability. Alternatively, at least two aliquots of the same reference sample may be analyzed together with the test sample. In said case, the technical variability can be assessed based on the at least two analyses of the at least two aliquots of the same reference sample. The samples are, preferably, subjected to pre-treatments including extraction and/or fractioning into polar and non-polar fractions comprising polar and non-polar metabolites. Preferably, the samples are prosecuted in the same sequence order in all steps.

In a second step, the metabolites present in the fractions will be determined. Said determining comprises qualitatively and quantitatively determining the composition of the metabolome. In light of the complexity of the metabolome (i.e. the number of metabolites), metabolites will be chromatographically separated first, preferably by LC and/or GC. Optionally, it may be required to derivatize the metabolites prior to LC and/or GC. Determining further comprises mass spectrometry. These techniques will yield processed raw data (i.e. raw results) for each sample, i.e. a three dimensional mass spectrum comprising various peaks.

In the analyzing step of the method, the peaks are validated based on monitored process parameters and by suitable peak validation algorithms which, e.g., investigate the geometry of a peak. In a subsequent step, the validated peaks are evaluated including normalization with respect to the actual and/or previous reference sample raw results. In accordance with the method of the present invention, it is not required to determine and analyze each metabolite of the metabolome. Rather, analysis of the metabolome may be carried out by determining the presence or absence or the amount of a portion of the metabolites found to be characteristic, a pre-selected set of metabolites or a specific metabolic profile for the metabolome. Characteristic or pre-selected metabolites comprise known metabolites as well as so called known unknowns. The latter ones are metabolites which are merely known from their signal in the results, e.g., peaks at a given retention time with a given mass spectra. The chemical nature (i.e. elementary composition and structure) of said known unknowns, however, is not precisely known. A metabolic profile as used herein relates to a specific profile as described above, wherein the underlying compounds are the metabolites of the metabolome. Analyzing the metabolome as used herein, preferably, includes a comparison of the metabolites, amounts of metabolites or the metabolic profile of different samples from e.g., organisms which have been subjected to different treatments. For example one sample or a group of samples may be derived from an organism or group of organisms to which a compound has been administered. The compound is suspected to affect the metabolome. Such compounds may be toxic compounds or potential drugs. A second sample or group of samples will be derived from an organism or group thereof serving as a control, e.g., will be left untreated or treated with a placebo. The comparison of the validated results obtained from the analysis of the samples will be carried out as described above. For example, PCA may be used to evaluate the samples. Thereby, a degree of similarity between the samples and, thus, the metabolomes of the organisms can be determined.

The method of the present invention is, preferably, assisted by automation. For example sample processing during, e.g., extraction, fractioning, chromatography and/or determination can be automated by robotics. Analysis of the raw results including validation and evaluation is, preferably, assisted by suitable computer programs and databases. A preferred system for carrying out the method of the present invention is described in detail below. Automation as described herein before allows using the method of the present invention in high-throughput approaches.

Advantageously, it has been found in accordance with the present invention that including reference samples as described above in the analysis will significantly improve the quality of the results obtained by the method. The use of the reference samples as described herein allows for sequence internal normalization and validation. Thereby, the influence of technical and/or biological variability is significantly reduced. Accordingly, thanks to the present invention analysis of chemical sample and, in particular, analysis of the complex biological samples becomes more reliable. Therefore, metabolomics can be reliably applied in fields which require high quality analysis such as toxicology, pharmacology and environmental control. Nevertheless, also classical chemical analysis (including exploratory compound analysis and quality control, e.g., in compound synthesis) will greatly benefit from the advantages of the method of the present invention.

Specifically, the present invention also pertains to a method for analyzing at least one test sample, wherein said test sample comprises at least one compound, said method comprising the steps of:
 a) providing at least one test sample comprising at least one compound;
 b) determining said at least one compound in said test sample using chromatography coupled mass spectrometry, whereby primary raw data are generated;
 c) generating raw results from the primary raw data obtained in step b) by the following procedures: (i) deconvolution of the primary raw data and allocation of the deconvoluted primary raw data to compounds using a reference spectrum and a reference retention index and (ii) allocating intensities and retention times to compounds using predetermined ion masses and time windows, and
 d) analyzing the raw results obtained in step c), wherein said analyzing comprises validation of the said raw results using a validation tool being capable of confirming or invalidating raw results based on rules whereby a set of validated results is generated,
 wherein the analysis of said at least one test sample is accompanied by an analysis of at least one reference sample;
 wherein the test sample and the reference sample are analyzed in an identical sequence in each step of the method; and
 wherein the method is assisted by automation.

The term "chromatography coupled mass spectrometry" as used herein relates to mass spectrometry which is coupled to a prior chromatographic separation of the compound(s) comprised by the samples to be investigated. As discussed elsewhere in this specification, chromatography may be, preferably, liquid and/or gas chromatography.

The term "generating raw results" relates to processing of the primary raw data into raw results. Processing of the primary raw data can be carried out by deconvolution techniques and allocation techniques as recited above. How to carry out such techniques and how to obtain suitable reference spectra is well known in the art. A mass spectrum will, thus, yield raw results which can be characterized by values for at least three dimensions, i.e. a retention time dimension as a result of chromatographic separation, an mass related dimension (e.g., m/z) depending on the compound(s) comprised by the sample, and an intensity related dimension depending on the presence or absence or the quantity of the compound(s).

The term "validation tool" relates to means which are capable of confirming or invalidating raw results obtained from a sample. The invalidated raw results shall not be considered further for the analysis, i.e. the subsequent evaluation steps. To this end, these raw results may be deleted or stored in a separate database. Raw results being confirmed by the validation tool will be kept for further evaluation and constitute a set of validated results being representative for the compounds in a sample which can reliably be analyzed. The validation tool shall comprise an algorithm which invalidates or confirms the raw results (peaks) generated from the mass spectra by conventional algorithms, e.g., AMDIS (http://chemdata.nist.gov/mass-spc/amdis/) or GC/MS Chem Station (Agilent Technologies). The validation tool investigates each raw result using a set of rules. The rules are functionally implemented into the validation tool. Thus, the validation tool, preferably, comprises a computer implemented algorithm and a rule data base comprising the aforementioned rules functionally linked to each other. The rules to be applied in accordance with the present invention shall validate or invalidate a raw result based on the following parameters: Proper retention time; proper retention index; validated raw results available for all standards, including those for determining the retention indices and those for normalization in subsequent steps. In addition to the aforementioned parameters, more preferably, the following parameters may be considered: Proper retention time values for all conventional algorithms which are used (e.g., proper retention time values for AMDIS and ChemStation generated raw results); Proper retention index values and calculations for all conventional algorithms which are used (e.g., proper calculated (i.e.

extrapolated) retention index based on retention index reference standards comprised by the sample obtained from AMDIS and ChemStation raw results); proper allocation of compounds to raw results; proper order of compound elution reflected by the generated raw results. Moreover, the validation tool may, preferably, consider further parameters including proper instrument and sample parameters or parameters indicating proper function of the entire process as described in detail elsewhere in this specification.

It is to be understood that the step of analyzing may, of course, also encompass the evaluation of the validated results, preferably, by the algorithms specified above and, in particular, by applying the "MMM"- or the "SICI"-Approach.

Preferably, the rules implemented by the validation tool comprise the following rules:

(a) determining for each raw result obtained by procedure (i) and (ii) in step c) whether the retention time (RT) provided for a raw result of a compound is within predetermined limits, if the retention time is outside the limits, the raw result is to be invalidated;

(b) determining for each raw result obtained by procedure (i) and (ii) in step c) whether the mass spectral match quality of said raw result of a compound in comparison to a predetermined reference result is above a predetermined limit, if the match quality is below the limit, the raw result is to be invalidated;

(c) determining for each raw result obtained by procedure (i) and (ii) in step c) whether the retention index (RI) provided for a raw result of a compound is within predetermined limits, if the retention index is outside the limits, the raw result is to be invalidated; and (d) determining for each raw result obtained by procedure (i) and (ii) in step c) whether a raw result for a compound is allocated to a validated raw result of a compound to be used for normalisation, if the raw result for the compound to be used for normalization is invalid, the raw results allocated thereto are invalidated, too;

The term "mass spectral match quality" as used in rule (b), above, means the degree of similarity between the mass spectrum to be analyzed and the reference spectrum. Said degree of similarity must be above a predetermined threshold otherwise the result is to be invalidated. Preferably, the degree of identity shall be at least 30%, at least 40%, at least 50%, at least 60%, at least 70%, at least 80%, or least 90%.

More preferably, the rules further comprise at least one rule—and most preferably, all rules—selected from the group consisting of:

(a) determining whether the retention time provided for a raw result of a compound obtained by procedure (i) (RT1) and the retention time provided for the same raw result by procedure (ii) (RT2) are within predetermined limits, if one of the retention time is outside the limits, the raw result is to be invalidated;

(b) determining whether the retention index (RI1) provided for a raw result of a compound obtained by procedure (i) and the retention index (RI2) provided for the same raw result by procedure (ii) are within predetermined limits, if one of the retention index is outside the limits, the raw result is to be invalidated;

(c) using the raw result having the largest value for the area under a curve generated by the data points in case a compound has been allocated in step c) to more than one raw result after applying the other rules comprised by the rule database;

(d) determining for each raw result obtained by procedure (i) and (ii) in step c) whether a retention index of a raw result is within predetermined limits based on a retention index standard for linear modelling, if the extrapolated retention index is outside the limits, the raw result is to be invalidated;

(e) determining for each raw result obtained by procedure (i) and (ii) in step c) whether a raw result for a compound has a predetermined valid neighbour raw result within a predetermined retention time or retention index range and a predetermined elution order, if no such valid neighbour raw result exists, the raw result is to be invalidated;

(f) determining for the each raw result obtained by procedure (ii) in step c) whether the area under a curve generated by the data points of the raw result does not have a negative value, whereby a raw result having a negative value is to be invalidated.

The term "linear modelling" as used in rule (d) means that based on the retention index standards, a predefined, preferably, linear function of the retention indices is to be calculated. This function shall be the basis for the setting of the limits for the extrapolated retention index of a raw result to be analyzed.

In rule (f), it is to be understood that negative values of raw results are caused by improper integration.

Advantageously, the aforementioned method of the present invention allows an efficient and reliable analysis of mass spectrometry data and is even very well suited for high throughput screenings. Specifically, due to the use of the validation tool, a maximum on information (i.e. raw results) of a sample can be used for further evaluation purposes. The conventional techniques for validation, usually, aim to invalid an entire set of raw results obtained from a sample. Consequently, the entire information from a sample—including information which, in principle, may be useful—is usually lost. Other techniques aim to identify ambiguous raw results which subsequently need to be investigated manually by a researcher. It is to be understood that these techniques are not very well suited for automation and, thus, for high throughput screenings. Thanks to the aforementioned method of the present invention, mass spectra can be reliably investigated whereby due to the validation tool the ambiguous raw results are invalidated in an automated manner while the informative raw results are confirmed and maintained for subsequent evaluations.

In a preferred embodiment of the aforementioned method, said analyzing further comprises generating a specific profile for the test sample based on the validated results.

Moreover, the present invention also pertains to a method having the features of the above method except that analyzing in step d) comprises generating a specific profile based on the raw results rather than on the validated results. It is to be understood, that for such a method, a validation tool as described above, may not be required.

Such a method, advantageously, allows for a rapid although less precise comparison of two samples. Such a comparison, pivotally, aims to detected whether two samples differ from each other rather than to identify the individual differences.

Further preferred embodiments of all of the aforementioned methods of the present invention are described as follows.

In a preferred embodiment of the method of the present invention said at least one reference sample is selected from the group consisting of:
(a) a reference sample comprising a portion of at least one test sample;
(b) a reference sample comprising a plurality of defined reference standards;

(c) a reference sample comprising a portion of the reference sample (a) and a portion of the reference sample (b);

As described above, a reference sample to be used in accordance with the method of the present invention comprises at least one compound and, preferably, a plurality of different compounds. Therefore, in a preferred embodiment of the method of the present invention a portion of the test sample may be used as a reference sample as described above. Preferably, such a reference sample will be a reference for technical or technical and biological variabilities and, more preferably, at least or technical variabilities. More preferably, the latter one of the aforementioned reference sample comprises a portion of each test sample to be analyzed in a series of analyses, i.e. being a pool of at least one of the test samples to be analyzed.

Moreover, the reference sample may comprise a plurality of defined reference standards. Such a reference sample may either essentially consist of said defined reference standards or may contain in addition to said reference standards further compounds. A reference sample as mentioned before which comprises further compounds may be, preferably, a reference sample comprising a portion of at least one test sample or a reference sample being a pool of test samples of a series of analyses as described before to which the plurality of defined reference standards have been admixed. Defined reference standards are compounds of known chemical nature for which a recovery rate is known for each step or the entireties of steps of the method of the present invention. Moreover, reference standards may comprise compounds for which a derivatisation efficacy is known or for which efficacy rates for other pre-treatments are known. Such reference standards are required for calculating recovery rates during the method of the present invention or efficacy rates (e.g., for derivatisation) during the method of the present invention. In addition, reference standards or reference samples can be used for the determination of the system suitability and sensitivity within a sequence. Preferably, reference standards comprising at least one characteristic compound of the different chemical classes of the metabolites mentioned earlier is used. They may comprise compounds which are usually present in test samples or usually not present, but may be present in test samples after a treatment. Reference standards are used also to allocate the identical compound in a reference sample, with or without this compound, or a test sample or to proof the absence of this compound in a test sample. Alternatively, isotopically labelled derivatives of said metabolites can be used. The application of isotopically labelled reference standards is well known to a person skilled in the art. Therefore, it is preferably envisaged to include at least one reference sample comprising a plurality of defined reference standards and/or at least a reference sample comprising a portion of a reference sample comprising a portion of at least one test sample and a portion of a reference sample comprising a plurality of defined reference standards into the method of the present invention.

Most preferably, the following standards which can be used for the calculation of the recovery rates are for the polar phase selected from the group consisting of: Arginine, Alanine, Leucine, Glycine, Serine, Proline, Glutamine, Cysteine, Tryptophan, Malic acid, Citric acid, Pyruvic acid, Homogentisic acid, Erythritol, Glyceraldehyde, Erythrose, Ribose, Xylose, Arabinose, Fructose, Mannose, Glucose, Galactose, Maltose, iso-Maltose, Saccharose, Maltotriose, Glucose-6-Phoshate, Fructose-6-Phoshate, Glucose-1-Phoshate, Glycerin-3-Phoshate, Putrescine, and Spermidine. For the non-polar phase most preferred standards are selected from the group consisting of: Stearic acid methyl ester, Linoleic acid methyl ester, trans-10, cis-12-Octadecadienoic acid, Linolenic acid methyl ester, Ricinolenic acid methyl ester, cis-5, 8,11,14,17-Eicosapentaenoic acid methyl ester, cis-4,7,10, 13,16,19-Docosahexaenoic acid methyl ester, Cerotic acid methyl ester, Montanic acid methyl ester, Melissic acid methyl ester, Palmitic acid, Triolein, Octadecanol, alpha-Tocopherol, Phytol, beta-Sitosterol, Cholesterol, Lipoic acid, trans-9-Hexadecenoicacid methyl ester, 2-Hydroxy-Hexadecanoate, and 3-Hydroxy-Hexadecanoate.

Moreover, in a preferred embodiment of the method of the present invention further reference samples may be included such as blanks for each step of the method of the present invention or the method in its entirety. Suitable blanks may be included for proving the purity of solvents and other agents used in the method of the present invention. Furthermore, retention time locking (RTL) standards may be included, if determining involves chromatography. RTL is a procedure that allows the chromatographer to reproduce analyte retention times independent of GC system, column length, or detector as long as columns with the same stationary phase, nominal phase ratio, and diameter are used. RTL is accomplished by adjusting the GC column head pressure until a given analyte, so called RTL-standard, which can also be an internal standard, has the desired retention time. When this is done, all other analytes in the chromatogram will have most precise retention times as well. For retention time locking, a reference sample comprising polar or non-polar standards will be applied to chromatography. Preferably, the reference samples and, more preferably, each sample contains the respective RTL-standard and RTL is performed after each injection of a RTL-standard containing sample. Suitable standards are well known in the art. Most preferably, methylnonadecanoate and ribitol-5-TMS are used as RT locking standards for the non-polar and polar fractions, respectively.

Moreover, in a preferred embodiment of the method of the present invention internal standards are added to each sample. The usage of internal standards is well known in the art, especially they are used to compensate (calculate) sample loss during the processing or varying efficacy of extraction and derivatisation and varying sensitivity of the used instruments. The internal standard should be chemically as similar as possible to the respective analyte (i.e. at least one of the compound(s) present in the sample), preferably the isotopically labelled analyte itself is used, and is contained in the sample in a similar amount as the analyte. The more analytes (i.e. compounds) are determined and the more chemically different they are, the more appropriate internal standards should be used.

Moreover, in a preferred embodiment of the method of the present invention retention index standards (RI-standards) are added to each sample. The usage of RI-standards is well known in the art, especially described as Kovats-RI-standards and their use for Kovats-RI-calculation. These standards consist of a homologuous series of compounds with different number of carbon atoms, such as the n-alkanes or straight chain fatty acids, preferably those with odd carbon numbers, or derivatives thereof, which are not of interest as metabolites, most preferred the trimethysilylesters of straight-chain fatty acids with odd carbon numbers between 7 and 31. By linear interpolation of the analyte retention times within the RI-standard retention times, using known methods from the literature, retention indices (RI) are obtained, which are more precise and representative for an analyte than the retention time itself, independent of GC system, column length, or detector as long as columns with the same stationary phase, nominal phase ratio, and diameter are used.

In a further preferred embodiment of the method of the present invention said test sample and said reference sample are analyzed in identical sequence order. Most preferably, the sequence order is established prior to analysis of the samples by random positioning of the at least one test sample and the at least one reference sample within said sequence order.

As described above, it has been found in accordance with the present invention that the test samples and reference samples to be analyzed by the method of the present invention must be analyzed in an identical sequence. Moreover, in a preferred embodiment, the test and reference samples shall be processed in each step of the method of the present invention in an identical sequence order which, most preferably, has been determined by random positioning. Nevertheless, it should be emphasized that the sequence order may also be a preselected sequence order. Accordingly, a sequence order, e.g., T1-R2-T2-R1, for two test samples (T1 and T2) and two reference samples (R1 and R2) may be obtained by random positioning or preselected positioning. The samples will be processed in each of the steps of the method of the present invention in said sequence order. In other words, providing of the samples including any kind of pretreatment will be done in the order T1-R2-T2-R1, determining of the at least one compound will be done for the samples in the order T1-R2-T2-R1. It has been found in accordance with the present invention that having an identical sequence order during the aforementioned steps of the method of the present invention will further improve the quality of the results which are generated. Specifically, the technical variability will be further diminished by said measure.

In another preferred embodiment of the method of the present invention, said analyzing in step c) comprises normalization of the raw results of the at least one test sample with respect to the raw results obtained for the reference sample.

Normalization as referred to above means that the validated results of the at least one test sample are normalized with respect to the validated results obtained for the at least one reference sample by the actual analysis. Moreover, normalisation serves to minimize influences by technical variability of the devices used to carry out the method of the present invention. Accordingly, the results obtained for the reference samples shall be regarded with respect to previously obtained results for the same reference samples. The actual and previous results obtained for the reference samples are, preferably, compared to each other, in order to assess the technical variability. Normalization of the raw results obtained for the at least one test sample will then be made based on said assessment. For example, based on the said assessment, a standard deviation may be calculated for a series of analyses for a plurality of test samples. Further, the raw results obtained for the at least one test sample will then, preferably, be normalized using either all or a subset of the reference samples. Preferably normalisation of raw results is done sequence- and compound-wise to adjust for technical variability. For a plurality of test samples from a plurality of sequences and for a plurality of compounds, raw results are normalised sequence- and compound-wise to all corresponding reference samples (or a subset thereof). This normalisation is done by relating the raw result of a sample to a statistical parameter (e.g. standard deviation, mean, median or a percentile) describing the corresponding reference population (or a subset there from). Thereby, the influence of the technical variability on the results obtained by the analysis will be significantly minimized.

In a further preferred embodiment of the method of the present invention said method further comprises monitoring of process parameters for said method.

The process parameters to be monitored in accordance with the method of the present invention are parameters which indicate technical inconsistencies or obstacles. For example, efficacy rates for pre-treatments or recovery rates for chromatography may be monitored. Moreover, it is envisaged to monitor technical operation parameters (e.g. current variations etc.) of the devices used for carrying out the method of the present invention. For instance, the function of all electronic devices can be monitored by techniques well known in the art. Electronic devices include computers, chromatographic devices, robots, and devices for compound analysis such as mass spectrometry devices.

Preferably, the following process parameters are monitored prior to the measurements: Time scheduled control of maintenance and cleaning procedures like mass calibration, exchange/control of spray needle, total number of injections made on the system, exchange of inline filters, control and/or exchange of pump oil, exchange of the analytical separation column, exchange of pre-columns, cleaning of the internal surfaces of the mass spectrometer, vacuum tests, pressure tests, and performance test with control solutions. During and/or after the analysis of a sequence the following process parameters are, preferably, monitored: Identifier of instrument used, timestamps (waiting time within the process) of instrument actions, any sample-instrument and sample-to-sample relations, (sequence) process observations (bumping or other normally not occurring observations), mass spectrometer tune values before and after the measurement of one sequence, column performance, (bad performance is recognized by regular check of certain analyte retention time shifts for lipid or polar analysis exceeding the limit or from peak form parameters), completeness of sequence measurement and data flow (processing, archiving, data availability in the data base, tracking in LIMS), visual inspection of the raw data checking for column bleed, contaminations, matrix loss, derivatisation problems. Preferably, said parameters and descriptions are collected in a database like a laboratory information management system (LIMS) as described elsewhere in this specification.

Preferably, the monitored process parameters will be stored in a database. It is envisaged that the monitored process parameters are available for validation of the raw results during the analysis step of the method of the present invention. Therefore, the database comprising the monitored process parameters is preferably operatively linked to the analyzing device to be used for carrying out the method of the present invention.

In a more preferred embodiment of the method of the present invention said analyzing in step c) comprises confirming or invalidating raw results based on the monitored process parameters.

Invalidating raw results encompasses invalidation of the entire raw results obtained from a test sample or invalidation of specific data points of the raw results. For example, if mass spectrometry is used for analyzing in step c), an entire mass spectrum may be invalidated or specific peaks may be invalidated. The latter case may happen if inconsistencies occurred during chromatography. In such a case, peaks of the three-dimensional mass spectrum within a certain range of retention time corresponding to the time range when the technical inconsistency occurred may be invalidated. Moreover, raw results of an entire sample shall be invalidated under the following specific conditions: (i) retention time standards can not be determined or are invalid; (ii) monitored process parameters are inconsistent; or (iii) sample (e.g., original weight, source, etc.) related information, preferably original weight, is not available. The invalidated raw results may be deleted or may be stored, preferably, in a separate database.

In another preferred embodiment of the method of the present invention said analyzing in step c) comprises peak analysis of the raw results. Most preferably, said peak analysis is carried out by a computer.

As described before already, in a preferred embodiment of the method of the present invention raw results are data points which can be arranged in a three-dimensional format resulting in maxima and minima. The maxima (also referred to as peaks) can be investigated by peak analysis tools which compare the peaks of the raw results with a hypothetical optimized peak geometry or with the geometry of a peak of a reference standard compound. A hypothetical optimized peak, for example, may have the geometry of a Gaussian distribution. If the raw results are generated by mass spectrometry as described before, the resulting peaks will be, preferably, investigated as follows: Peak based parameters which are checked by peak analysis are elution order of peaks, peak shape parameters like signal-to-noise ratio, peak symmetry, peak shoulders, slope of the integration baseline, baseline peak width, peak width at half height, separation from neighboring peaks (e.g. baseline separation), absolute peak intensities, relative intensities to an internal standard, absolute retention time, relative retention time to an internal standard or another substance, coefficients of variation and possible trends of retention time, relative retention time, peak heights and/or peak areas. Furthermore it is checked that all internal standards and RI-standards are found by the software. Special peaks, indicative for known possible process problems (thawing, cross contamination, derivatisation efficiency), are also checked. Reagent blank samples are checked for assessment of contaminations during the process. Furthermore, it is checked whether RI-standards, internal standards and known and known unknown analytes fulfill individual RT- and/or MS-match quality criteria. Furthermore, it is cross checked that the same analyte is found with peak finding and deconvolution software at same RI and RT with good match. For certain compounds (analytes) only a subset of the above mentioned criteria can be checked. Controls and records are done partial manually or automatically, for some usual parameters there are clear levels where exceeding results in invalidation, others are assessed manually and followed if clear differences to usual values are seen. Depending on the severity of the deviation from the normal, consequences may be rejection of the sequence, the sample, or the peak, placing instrument out of operation (repair or change components, depending on tune, column performance etc.) or only a remark for further notice. If necessary (analyte or sample is conspicuous in evaluation) manual recheck of peak annotation and sample quality can be done repeatedly.

Peak analysis can be carried out by algorithms which are comprised by the peak analysis tool well known in the art. Suitable peak analysis tools are, for example, ChemStation (Agilent Technologies, USA), Analyst (MDS SCIEX, Canada) or AMDIS (NIST, USA). A suitable algorithm to be used for peak analysis, preferably, encompasses a noise analysis, a component perception, a spectral deconvolution and a peak identification step. Besides ChemStation, Analyst and AMDIS suitable algorithms are, inter alia, described in Biller, 1974, Reconstructed mass spectra, A novel approach for the utilization of gas chromatograph-mass spectrometer data, Anal. Lett. 7: 515-528, Colbi, 1992, Spectral deconvolution for overlapping GC/MS components, J. Amer. Soc. Mass Spectrom. 3: 558-562, Herron, 1996, Software-based mass spectral enhancement to remove interfaces from spectra of unknowns 7: 598-604, Pool, 1997, Automated extraction of biomass spectra from gas-chromatographic/mass spectrometric data, 32: 438-443, Tromey, 1976, Extraction of mass spectra free of background and neighbouring component contributions from gas chromatography/mass spectrometry data, Anal. Chem. 48: 1368-1375, Rosenthal, 1981, Improvement of algorithm for peak detection in automatic gas chromatography-mass spectrometry data processing, Anal. Chem. 53: 538-539. In an even more preferred embodiment of the method of the present invention said peak analysis further comprises confirming or invalidating raw results based on the results obtained by the peak analysis.

As described for the monitored process data, raw results or parts thereof can be invalidated also based on the result of the peak analysis. The explanations made above apply mutatis mutandis. The invalidated raw results may be deleted or stored, preferably, in a separate database.

In a preferred embodiment of the method of the present invention said analyzing in step c) comprises generating a specific profile based on the raw results.

A specific profile is generated based on raw results or validated results of a certain test sample. Preferably, it is envisaged that the specific profile, like a fingerprint, specifically identifies said sample. As described above, specific profiles may comprise raw results, validated results or results derived there from.

Specific profiles may be generated by techniques known in the art and described, e.g. in Per Johnson, 2005, Extraction interpretation invalidation of information for comparing samples in metabolic LC/MS data sets, Analyst 130: 701-707. Here a method is described which allows for creating robust and interpretable multi-variant models for the comparison of many samples. The method described involves the construction of a representative data set, including automatic peak detection, alignment, setting of retention time windows, summing in the chromatographic dimensions and data compression by means of alternating regression. The method, thus, allows for the comparison of large numbers of samples based on their LC-MS metabolic profiles. Another suitable method for generating a specific profile may be found in Per Johnson 2004, A synergy for identifying differences in large theories of metabolomic samples analyzed by GC/MS, Analytical Chemistry 76: 1737-1745. Here a method for identifying and quantifying metabolites in a biological system is described. The method includes baseline correction, alignment, time window determination, alternating regression, PLS-DA, and identification of retention time windows in the chromatograms that explain the differences between the samples. Similarly operating techniques are disclosed, e.g., in WO 2003/102543 or US 2005 0127287, the disclosure content of which is hereby incorporated by reference.

A preferred method for generating a specific profile based on raw results includes generating a three-dimensional set of raw results, wherein the first dimension is the signal intensity and the two other dimensions relate to characteristic features, preferably to a mass variable and/or a time variable. In a second step, the second dimension, preferably the mass variable dimension, is divided into at least two mass variable intervals and an extracted signal for each mass interval is selected, wherein the extracted signal is a function of the time. Finally, the third dimension, preferably, the dimension of the time variable, is divided into at least one time variable interval and a characteristic value is selected for each time variable interval and for each extracted signal. Thereby, a specific sample profile is generated comprising the selected characteristic values as a function of the respective time variable interval and the respective mass variable interval. Extraction of the signals is preferably carried out by integration, summing, averaging, selecting at a boundary or selecting based on maxima or minima. Most preferably, the characteristic value for each time variable interval is selected by integrating the extracted signal over each time variable interval. Furthermore, the method may include the use of peak analysis algorithms as described above to detect peaks in the extracted signal within each time variable interval, in case the specific profile is based on raw results. A particular preferred method for generating a specific profile is described in Examples 1 to 3, below. Most preferably, the specific profile to be generated in accordance with the method of the present invention is a metabolic profile being specific for a metabolome.

Further preferred is an embodiment of the method of the present invention, wherein said determining in step b) comprises mass spectrometry.

Mass spectrometry as used herein encompasses all techniques which allow for the determination of the molecular weight (i.e. the mass) or a mass variable corresponding to a compound to be determined in accordance with the present invention. Preferably, mass spectrometry as used herein relates to GC-MS, LC-MS, direct infusion mass spectrometry, FT-ICR-MS, CE-MS, HPLC-MS, quadrupole mass spectrometry, any sequentially coupled mass spectrometry such as MS-MS or MS-MS-MS, ICP-MS, Py-MS, TOF or any combined approaches using the aforementioned techniques. How to apply these techniques is well known to the person skilled in the art. Moreover, suitable devices are commercially available. More preferably, mass spectrometry as used herein relates to LC-MS and/or GC-MS. More preferably, mass spectrometry as used herein encompasses quadrupole MS. Most preferably, said quadrupole MS is carried out as follows: a) selection of a mass/charge quotient (m/z) of an ion created by ionisation in a first analytical quadrupole of the mass spectrometer, b) fragmentation of the ion selected in step a) by applying an acceleration voltage in an additional subsequent quadrupole which is filled with a collision gas and acts as a collision chamber, selection of a mass/charge quotient of an ion created by the fragmentation process in step b) in an additional subsequent quadrupole, whereby steps a) to c) of the method are carried out at least once and analysis of the mass/charge quotient of all the ions present in the mixture of substances as a result of the ionisation process, whereby the quadrupole is filled with collision gas but no acceleration voltage is applied during the analysis. Details on said most preferred mass spectrometry to be used in accordance with the present invention can be found in WO 03/073464.

As referred to above, more preferably, said determining in step b) also comprises liquid chromatography prior to mass spectrometry.

Liquid chromatography as used herein refers to all techniques which allow for separation of compounds in liquid or supercritical phase. Liquid chromatography is characterized in that compounds in a mobile phase such as the at least one compound in the sample according to the method of the present invention are passed through the stationary phase. When compounds pass through the stationary phase at different rates they become separated in time since each individual compound has its specific retention time (i.e. the time which is required by the compound to pass through the system). Liquid chromatography as used herein also includes HPLC. Devices for liquid chromatography are commercially available, e.g. from Agilent Technologies, USA. Preferred examples for carrying out liquid chromatography are described in Examples 1 and 2, below.

Furthermore preferably, said determining in step b) comprises gas chromatography prior to mass spectrometry.

Gas chromatography as applied in accordance with the present invention in principle operates comparable to liquid chromatography. However, rather than having the compounds in a liquid mobile phase which is passed through the stationary phase, the compounds will be present in a gaseous volume. The compounds pass the column which may contain solid support materials as stationary phase or the walls of which may serve as or are coated with the stationary phase. Again, each compound has a specific time which is required for passing through the column. Moreover, in the case of gas chromatography it is preferably envisaged that the compounds are derivatised prior to gas chromatography. Suitable techniques for derivatisation are well known in the art. Preferably, derivatisation in accordance with the present invention relates to methoxymation and trimethylsilylation of, preferably, polar compounds and transmethylation, methoxymation and trimethylsilylation of, preferably, non-polar (i.e. lipophilic) compounds. Details for derivatisation are described in the Examples below.

In another preferred embodiment, the method comprises prior to step b) the further step of fractioning said at least one test sample into at least one first fraction comprising polar compounds and at least one second fraction comprising non-polar compounds.

The term "fractioning" as used herein refers to techniques for separation of compounds and/or enrichment of compounds. Suitable techniques for fractioning are well known in the art.

A fraction comprising polar components as referred to above, is preferably obtained by contacting the sample with a solvent for polar compounds and allowing the compounds to diffuse into said polar solvent (i.e. extraction of the polar compounds) resulting in an enriched fraction of polar compounds in said polar solvent. The polar solvent comprising the polar compounds will be separated from the remaining sample residue and represents the polar fraction referred to in accordance with the present invention. Polar solvents as used herein encompass solvents having a polarity index of 4.0 to 10.2, preferably 5.0 to 7.0 and more preferably 5.5 to 6.5 according to Kellner, Analytical Chemistry, Weinheim, 1998, p. 195. Polar solvents are accordingly water including water-containing solutions or polar protic or aprotic organic solvents, such as alkyl alcohols having an alkyl residue of 1 to 6 carbon atoms, such as methanol, ethanol, 1-propanol, 2-propanol, butanol, pentanol, hexanol, acetone, acetonitrile, acetic acid-ethylester, dimethyl-sulfoxide or N,N-dimethyl formamide. Further polar solvents have a polarity of at least 0.5 as referred to in Küster/Thiel, Rechentafeln für die chemische Analytik, Walter DeGruyter, Berlin/N.Y., 1993, p. 359 or mixtures thereof. Further solvents which are preferably to be used in accordance with the method of the present invention are disclosed in WO 03/041834. A polar solvent to be used in accordance with the present invention is, preferably, a mixture of water and an alcohol, preferably methanol, ethanol, propanol or isopropanol. Most preferably, the polar solvent is a mixture of methanol and water as described in the Examples below.

Similarly, a fraction comprising the non-polar compounds is preferably obtained by contacting the sample with a non-polar solvent for a time period sufficient to allow the non-polar compounds (i.e. the lipophilic compounds) to diffuse into the non-polar solvent (i.e. extraction of the non-polar compounds). A non-polar solvent according to the present invention refers to a solvent or solvent mixture having a polarity index according to Kellner, Analytical Chemistry, Weinheim, 1998, p. 195 of at least 0.3 less than the polarity index of the polar solvent of the polar fraction referred to above. More preferably, the polarity index is 0.5, more preferably 1.0 and most preferably 2.0 less than the polarity index of the polar solvent. Accordingly, the polarity index of the non-polar solvent is within a range of 5.5 to 1.0, more preferably 5.0 to 2.0 and most preferably 4.5 to 3.5. Non-polar solvents include halogenated solvents including chloroform, dichloromethane, carbon tetrachloride, or aliphatic solvents including hexane, cyclohexane, pentane or heptane, or aromatic solvents including toluene, benzene or ethers, such as tert.-butylmethyl-ether, diethylether or tetrahydrofurane. Preferably, fractioning as referred to in accordance with the present invention is carried out at room temperature. In order to achieve a reliable and accurate phase separation, fractioning is preferably assisted by a robot.

More preferably, said fractioning further comprises fractioning of each of said test samples into at least one third fraction comprising proteins, peptides or amino acids.

Fractions comprising proteins or peptides are, preferably, obtained by precipitating said proteins or peptides. The precipitated proteins can be separated from the remaining sample material by, e.g., centrifugation. Thereby, a solid pellet comprising the precipitated proteins or peptides will be formed and the remaining liquid sample can be processed as described above. The pellet may be dissolved in a solvent suitable for the further analysis. Fractions comprising amino acids may be obtained by hydrolysing a fraction comprising proteins. Alternatively the total amino acid content can be determined by hydrolysis of a portion of the sample without prior fractioning. Hydrolysis may be carried out by well known techniques including thermic hydrolysis, acidic hydrolysis or enzymatic hydrolysis.

In a further preferred embodiment of the method of the present invention said providing in step a) comprises extracting the at least one compound comprised by said at least one test sample.

Extraction as used herein refers to dissolving the compounds comprised by organic material, such as cells, tissues, organs, body fluids, leaves or seeds in a solvent. As described above, polar compounds may be extracted with a polar solvent while non-polar compounds may be extracted by using a non-polar solvent. Moreover, in order to improve efficacy of the extraction process, preferably, extraction will be carried out under elevated temperature and pressure as described in the following and in the Examples below. Extraction is carried out at temperatures within a range of 30° C. to 90° C., more preferably, at temperatures within the range of 60° C. to 80° C. and, most preferably, at 70° C. Pressure is preferably within the range of 100 bar to 180 bar, more preferably, within the range of 130 bar to 150 bar and, most preferably, 140 bar. Extraction as referred to in accordance with the present invention, preferably, encompasses liquid-liquid extraction. Moreover, more preferably, extraction further encompasses physical or chemical treatment of biological material (e.g., tissues or organs) in order to release the compounds. Physical treatments, preferably, include ball mill treatment, Ultra Turrax (IKA, USA) treatment or ultra sonification. Extraction is, preferably, assisted by an Accelerated Solvent Extractor (ASE).

In light with the foregoing, the at least one test sample is, preferably, derived from an organism, preferably, an organism of a plurality of organisms having an essentially identical metabolome. More preferably, said organisms are plants, animals, bacteria or fungi. The animals referred to in accordance with the present invention include non-human mammals and humans. Moreover, the organisms may have been genetically modified or otherwise treated as described in detail elsewhere in this specification.

In order to obtain high-quality results for a certain metabolome, it is envisaged because of statistical reasons to calculate statistical parameters (e.g. mean or median) characterizing a population comprised of different samples from different individuals of an organism. However, the individual organisms shall, in principle, have an essentially identical metabolome. In this context, an essentially identical metabolome means that all individuals of the population of organisms have synchronized metabolic activities resulting (i) in the presence of essentially the same metabolites in the metabolome of each individual of the population and (ii) in amounts of said metabolites which are essentially identical for each of the individuals of the population. It is to be understood that the metabolite amounts may vary between the individuals of the population within population statistical values. It is known to a person skilled in the art that statistical descriptors like percentiles can be used. An essential identical metabolome of the organism can be, preferably, determined by clustering together in a multivariate analysis, e.g. Principal Component Analysis (PCA), or hierarchical clustering.

As far as bacteria or fungi are concerned, such populations can be easily provided since these organisms can be propagated monoclonal and can be easily kept under identical housing conditions, e.g., within the same cell culture.

Animals which have an essentially identical metabolome can be provided by compiling an animal population being of essentially the same age and keeping said animal population for a time period sufficient for acclimatization under the following housing conditions: (i) constant temperature, (ii) constant humidity, (iii) physical separation of the animals of the animal population, (iv) feeding ad libitum, wherein the food to be fed is essentially free of chemical or microbial contaminants, (v) drinking liquid ad libitum, wherein the drinking liquid is essentially free of chemical or microbial contaminants, (vi) constant illumination period, and providing the animal population after said time period. Compiling, as referred to above, means to select the animals from any source to establish the animal population to be subjected to the method of the present invention. Accordingly, the animals may be progeny of the same mother animal or progeny of different mother animals. In case a single progeny of one mother animal is used as a source, either the entire progeny may be used for compiling the animal population or selected animals of the progeny may be used. Compiling as used herein is carried out with respect to the age of the animals, i.e. all individuals of the population shall have essentially the same age as described below in detail. However, further characteristics may be taken into account. In addition, such as weight, size, sex, overall appearance (e.g. only healthy animal by appearance may be selected). Being of essentially the same age means that the animals have a comparable status of development, e.g. the animals may be embryos, juveniles or adults. A preferred age of the animals to be used in the method of the present invention is an age of the adolescence stage, preferably young adolescence stage. The animals of the animal population, preferably, have an age with the range of $X \pm 1$ day, wherein X is the envisaged age of the animal population. In other words, a given animal of the population shall be at most one day older or younger than the average age of the animals of the animal population. Most preferably, all animals of the population are of age X. Such animals can be provided by compiling animals which are progeny of one litter, i.e. littermates, or which are compiled from different litters from the same day. In case embryos are to be used, it is to be understood that essentially the same age relates to their developmental stages. The developmental stages of embryos from various species can be determined by techniques well known in the art. They may be calculated, e.g., based on the time point of fertilization. Moreover, individual embryos can be developmentally staged due to known morphological features. Moreover, in case embryos are used, it is further to be understood that the pregnant mothers carrying said embryos shall be kept under the conditions referred to herein. If, e.g., rats or mice are used as animals in the method of the present invention, it is preferred that the animals are of age X±1 day, wherein X is 63, 64 or 65 days after birth. Most preferably, X is 64 days after birth. For dogs, a preferred age (X) shall be 6 month. Keeping as used in accordance with the method of the present invention, refers to particular housing, feeding, drinking and environmental conditions which are applied to the animals of the animal population. It is preferred that the animals are kept under conditions as set forth in the OECD Guideline for the Testing of Chemicals No: 407. Moreover, particular conditions are described as follows.

i) All animals of the animal population are kept under the same constant temperature. Care should be taken to choose a temperature for carrying out the method of the present invention which does not stress the animals. Preferably, temperature should be 20-24±3° C., more preferably 22±3° C., most preferably 22, 23 or 24° C.

ii) Moreover, all animals of the animal population are kept under the same constant humidity. The humidity should be at least 30%, but should not exceed 70%. However, in rare exceptional situations (such as during room or cage clearing) humidity may even exceed 70%. Preferably, humidity is 50-60%.

iii) Physical separation of the animals of the animal population has been found to be also important for the method of the present invention. Accordingly, each animal of the animal population must be kept in a separate space, e.g. a separate cage.

iv) The animals of the animal population are fed ad libitum. The food to be used must be essentially free of chemical or microbial contaminants. The standards to be applied are laid down in Fed. Reg. Vol. 44, No. 91, May 9, 1979, p. 27354. Most preferably, microbial contaminants such as bacteria are below $5 \times 10^5$ cells per g of food. Such food may be purchased from Provimi Kliba SA, Switzerland, as Ground Kliba mouse/rat maintenance diet "GLP" meal.

v) The animals of the animal population are supplied ad libitum with a drinking liquid. Preferably, said liquid is water. However, other liquids on water basis may be used as well. Such liquids may comprise, for instance, nutritions, vitamins or minerals which are required by the animals. If water is used as drinking liquid, the water shall be free of chemical and microbial contaminants as laid down in the European Drinking Water Directive 98/83/EG.

vi) Finally, each animal of the animal population must be subjected to the same constant illumination periods. Constant illumination is achieved, preferably, by artificial lightning (having the solar colour spectrum). The illumination period is 12 hours light followed by 12 hours darkness. Then the illumination period starts again. A preferred illumination period, thus, is 12 hours light, from 6:00 to 18:00, and 12 hours darkness, from 18:00 to 6:00.

The aforementioned housing conditions can be applied to the animals by using a common storage space for the cages comprising the physically separated animals. Said common storage space may be an animal room or house. By keeping all animals of the population in the same room, constant humidity, temperature and illumination period can be easily achieved by regulating these parameters for the entire room or house. Regulation of the parameters is preferably assisted by automation and the parameters are constantly monitored. Under a first time period sufficient for acclimatization it is to be understood that the animals of the animal population must be kept under the aforementioned particular housing conditions for a time period which allows synchronization of the metabolic activities of the animals so that the animals are acclimatized and have essentially the same metabolome. Specifically, the said first time period shall be of sufficient length as to allow all individuals of the population to adopt the same circadian rhythm, food digestion rhythm, or quiescence/movement periods. Moreover, the first time period shall allow each animal to adjust its biochemical and physiological parameters in response to the applied environmental conditions, such as humidity and temperature. Preferably, said first time period has a length of 5 to 10 days, more preferably 6 to 8, and most preferably 7 days.

A plant population having essentially the same metabolome can, for example, be obtained as follows: For *Arabidopsis* ecotype C24 (Nottingham *Arabidopsis* Stock Centre, UK; NASC Stock N906), stratification of the sown homogenous seeds, preferably, is carried out at 4° C. in the dark for 4 days. Humidity during said time period is kept between 85% and 95%, preferably at 90%. After stratification, test samples of, e.g., *Arabidopsis thaliana* are, preferably, grown for a period within the range of 22 to 23 days at the following conditions. Constant illumination period: 16 hours light period followed by 8 hours darkness period, whereby lightening reflects the solar colour spectrum, preferably, with a light intensity of 200-250 $\mu E/m^2/s$, most preferably, 200 $\mu E/m^2/s$; constant Temperature of 20° C.; constant humidity of 60%; constant $CO_2$ concentration of 400 ppm.

Preferably, said test sample is derived from cells, from a tissue or from an organ.

Cells, tissues or organs to be used as test samples in accordance with the present invention may be derived from an organism, preferably an animal, by techniques well known in the art, including surgery and biopsy. Moreover, test samples which are derived from cells, tissues or organs include any type of cell culture cells, cell lines or primary cell cultures derived from cells, and any type of tissue or organ cultures. Primary cells may be obtained from tissues or organs by dissection and dispersion. The isolated cells may be immortalized or transformed with an oncogene in order to obtain cell lines.

Also preferably, said test sample is derived from a body fluid. More preferably, the body fluid is blood, serum, plasma, lymph, saliva, cerebrospinal liquid, sudor, sperm, vaginal fluid, tears, feces or urine.

The aforementioned samples can be taken by techniques well known in the art. Suitable techniques include blood sampling, liquor sampling, or urine sampling. It is to be understood that depending on the nature of the sample, specific sample pre-treatments may be necessary, e.g., in the case of blood plasma it will be required to avoid coagulation by mixing the blood sample with coagulation inhibitors such as heparine.

Further preferred biological samples comprise volatiles of an organism.

In a preferred embodiment of the method of the present invention said method comprises the further step of providing an output result set containing the analyzed results of step c).

As described already above, analyzing as carried out in accordance with the method of the present invention may require that the data shall be available for evaluation steps encompassing a comparison of the validated results of two or more different samples. Moreover, it is envisaged that the analyzed results shall be available in a suitable format for storage or in a specific customized format for other evaluation steps. Accordingly, the term "providing an output result set" as used herein refers to converting the validated and normalized raw results and/or evaluated results in a suitable output format which can be used for storage or for comparison of different output result sets using the pattern recognition algorithm, statistical test algorithms or multivariate algorithm referred to above. Of course, the results may be converted in any other customized output format. Customized output formats as referred to before, may comprise formats such as Excel-files or ASCII files, or three-dimensional graphic representations of the validated and normalized raw results. Moreover, suitable customized output formats may be in form of total ion chromatograms (TICs).

The present invention also relates to a method for determining a trait specific for a first sample comprising:
a) comparing an output data set obtained by the method of the present invention for at least one first sample to an output data set obtained by the method of the present invention for at least one second sample; and
b) determining a trait specific for said at least one first sample based on the results of the comparison in step a), wherein a difference in the output data sets is indicative for a trait specific for said at least one first sample.

The term "specific trait" as used herein refers to a trait which allows distinguishing the first and second sample(s) from each other. The trait to be determined is the presence or absence of at least one specific compound, the abundance (i.e. the precise or relative amount) of at least one compound or a specific profile for a sample or a portion thereof.

The terms "first sample" and "second sample" refer to different sample entities. The samples may, thus, comprise different compounds or they may comprise different precise or relative amounts of the same compounds. For example, a first and a second biological sample may be obtained from the same organism, merely differing in that the samples have been obtained prior and after a certain treatment or are derived from different cells, tissues or organs of said organism. Of course, the first and second samples may be obtained from organisms of different species or organisms of the same species which have been subjected to different treatments as described already above. A first and second environmental sample for instance may be obtained from the same environmental location, e.g., before and after an environmental event. Moreover, a first and second environmental sample may be obtained from a corresponding first and second environment.

The term "difference in the output data sets" encompasses qualitative and quantitative differences. Accordingly, a difference obtained as a result of the comparison in step b) of the method of the present invention may be a difference in the presence or absence of a compound, in its abundance or a difference in a specific profile. Preferably, it is envisaged that a difference as referred to herein in the output data sets is a statistically significant difference. Whether a difference is statistically significant can be tested by statistical tests well known in the art. The aforementioned differences can, in principle, be determined by pattern recognition algorithms, statistical test algorithms and/or multivariate algorithms, e.g., Principal Component Analysis (PCA), Simple Component Analysis (SCA), Independent Component Analysis (ICA), Principal Component Regression (PCR), Partial Least Squares (PLS), PLS Discriminant Analysis (PLS-DA), Support Vector Machines (SVM), Neural Networks, Bayesian Networks, Bayesian Learning Networks, Mutual Information, Backpropagation Networks, symmetrical Feed-Forward Networks, Self-Organizing Maps (SOMs), Genetic Algorithms, Hierarchical or K-Mean Clustering, Anova, Student's t-Test, Kruskal-Wallis Test, Mann-Whitney Test, Tukey-Kramer Test or Hsu's Best Test. More preferably, one of the aforementioned specific algorithms is used for the comparison, most preferably, the "method of shrunken contrasts" or the "SICI Approach".

The term "indicative" as used herein means that it might be required to further confirm the trait determined by the method of the present invention for a first sample. For example, specificity of a trait for a sample may be further confirmed. However, indicative as used in accordance with the aforementioned method, preferably, means that the trait determined based on the said difference is a trait specific for said first sample.

The present invention, furthermore, relates to a method for determining a common trait for a first sample and a second sample comprising:
a) comparing an output data set obtained by the method of the present invention for at least one first sample to an output data set obtained by the method of the present invention for at least one second sample; and
b) determining a common trait for said at least one first sample and said at least one second sample based on the results of the comparison in step a), wherein a similarity in the output data sets is indicative for said common trait.

The term "common trait" as used herein refers to a trait which allows determining the similarity of at least two samples to each other. The trait to be determined is the presence or absence of at least one specific compound, the abundance (i.e. the precise or relative amount) of at least one compound or a specific profile for a sample or a portion thereof.

The term "similarity in the output data sets" encompasses qualitative and quantitative similarities. Accordingly, a similarity obtained as a result of the comparison in step b) of the method of the present invention may be a similarity in the presence or absence of a compound, in its abundance or a similarity in a specific profile. Preferably, it is envisaged that a similarity as referred to herein in the output data sets is a statistically significant similarity. Whether a similarity is statistically significant can be tested by statistical tests well known in the art. The aforementioned similarity can, in principle, be determined by pattern recognition algorithms, statistical test algorithms and/or multivariate algorithms, e.g., Principal Component Analysis (PCA), Simple Component Analysis (SCA), Independent Component Analysis (ICA), Principal Component Regression (PCR), Partial Least Squares (PLS), PLS Discriminant Analysis (PLS-DA), Support Vector Machines (SVM), Neural Networks, Bayesian Networks, Bayesian Learning Networks, Mutual Information, Backpropagation Networks, symmetrical Feed-Forward Networks, Self-Organizing Maps (SOMs), Genetic Algorithms, Hierarchical or K-Mean Clustering, Anova, Student's t-Test, Kruskal-Wallis Test, Mann-Whitney Test, Tukey-Kramer Test or Hsu's Best Test. More preferably, one of the aforementioned specific algorithms is used for the comparison, most preferably, the "method of shrunken contrasts" or the "SICI Approach".

The term "indicative" as used herein means that it might be required to further confirm the trait determined by the method of the present invention for a first sample. For example, similarity of a trait for a sample may be further confirmed. However, indicative as used in accordance with the aforementioned method, preferably, means that the trait determined based on the said similarity is a trait which the samples have in common.

Specifically, encompassed by the present invention is also a method for determining effects caused by a treatment applied to an organism comprising the steps of the method of the present invention and the further step of determining the effects based on a trait specific for a first sample of the said organism. More preferably, said treatment is genetic modification of the organism, administration of a compound, physical treatment, change of an environmental condition, radiation applied to the organism or a combination of said treatments.

As described before, the method of the present invention is specifically useful for determining effects which are caused by a certain treatment of an organism. Usually, effects caused by a treatment of an organism as meant herein are treatments which cause changes of the metabolome. As already mentioned before, metabolites closely reflect the actual cellular activities in response to various treatments, including exogenous factors, such as administration of compounds, change of environmental conditions or radiation or changes caused by genetic modifications of the genome of the organism. Therefore, it is preferred that the effects which are determined based on a trait specific for a first sample by the method of the present invention are effects on the metabolome of an organism to which the treatment has been applied.

As referred to above, the method of the present invention more specifically encompasses a method for determining the effects caused by genetic modifications of an organism. Genetic modifications may be introduced by random mutagenesis of the organism using DNA modifying agents, such as ethyl nitrose urea (ENU), ethyl methyl sulfate (EMS), by homologous or heterologous recombination or by insertional mutagenesis. Depending on the organism, insertional mutagenesis can be carried out by suitable insertion systems including T-DNA sequence insertions or transposons in plants, non-viral, retroviral or transposon vector systems for animals, knock-out and knock-in approaches in animals using a loxP system, or related systems well known to a person skilled in the art. Moreover, genetic modification as used herein encompasses introducing of an expression cassette comprising a gene of interest into an organism, wherein said expression cassette can be integrated stably into the genome of the organism or remain in the cytoplasm. The genetic modification referred to in accordance with the present invention preferably results in the absence or the reduction of the amount of a gene product in the organism or parts thereof or the presence of a new gene product or the increase in the amount of a gene product in said organism or a combination thereof. Moreover, it is envisaged that due to said genetic modification, the metabolome of the organism or parts thereof will change, i.e. metabolites will disappear, a change in their abundance will happen or new metabolites will appear. A genetic modification as referred to before, includes all techniques for modulating gene expression, i.e. modulation of the genome, transcription, RNA processing or stability or translation. Accordingly, genetic modification is preferably elicited by a technique selected from the group consisting of: overexpression of a gene of interest by, e.g., introducing a transgene, introducing RNA transcribed from said gene, homologous recombination (knock-in approaches), inhibition of transcription of a gene by homologous recombination (knock-out approaches), oligonucleotide interference-based approaches, RNAi-approaches, microRNA-based approaches, triple helix-based approaches, co-suppression or antisense RNA-based approaches. The gene of interest referred to above may be a gene which directly affects a metabolite (e.g. an enzyme) or a gene which modulates the expression of the aforementioned gene (e.g. a gene for a transcription factor specific for an enzyme gene or a gene encoding a protein which modulates stability, processing or transport for a RNA encoding an enzyme). In other cases the gene of interest may also be a unknown gene or a gene which only indirectly influences the metabolism, since the genetic modification of such genes and the subsequent determination of metabolic effects may be helpful for characterising and studying the gene function.

As mentioned before, administration of a compound usually also alters the metabolome of an organism. Nutritients or nutraceuticals, toxic compounds or drugs, for example, elicit typical changes in the metabolome of an organism. Said typical changes correspond to the effects to be determined based on the said trait specific for a sample of an organism. Administration of such compounds can be achieved by various techniques depending on the organism. Single-cellular organisms, such as bacteria or fungi, may be cultured in a medium comprising the compound to be administered. Plants may obtain the compound by water intake or by spraying, bombardment, infiltration, inoculation, or other techniques well known to a person skilled in the art. With respect to animals, administration of a compound encompassed all techniques by which the compound is provided systemically to the animal, i.e. treatment of the entire animal. Moreover, administration as used herein encompasses techniques for delivering the compound to the suspected site of action, such as a potential target tissue or organ, i.e. topical administration. The compound to be administered in accordance with the present invention may be comprised in a composition further comprising suitable carriers such as pharmaceutical carriers, excipients and/or diluents. Examples for well known diluents include phosphate-buffered saline solutions, water, emulsions, such as oil/water emulsions, various types of wetting agents, sterile solutions, etc. Administration of the compound or the aforementioned composition may be affected by different ways, e.g. by intravenous, intraperitoneal, subcutaneous, intramuscular, topical, intradermal, intranasal or intrabronchial administration. In case of an animal, more preferably administration is achieved by oral administration, most preferably the compound is admixed to the drinking liquid, the food or by using a composition for oral administration (i.e. gavage) comprising the compound to be administered and a pharmaceutical carrier for oral uptake such as plant oil.

The effects on the metabolome elicited by a compound are, preferably, useful as read out for screening assays. Compounds having a certain desired property may be identified, in principle, due to their capability to elicit a metabolome similar or identical to a metabolome elicited by a compound known to have the desired property. Preferred properties to be identified in such a screening assay are therapeutic properties of a compound (i.e. the screening assays aims to identify new drugs) or plant protection properties (i.e. the screening assay aims to identify new plant protection compounds). Further details for such an application of the method of the present invention are to be found elsewhere in this specification.

Physical treatments to be applied in accordance with the method of the present invention encompass exogenous and endogenous physical treatments. Exogenous physical treatments are those which are applied to the organism by its environment. For example, an organism may be subjected to a physical force which influences its structural integrity. Such treatments comprises, e.g., surgery. Endogenous treatments are those which are applied to the organism based on its own capacity. Preferred endogenous treatments referred to in accordance with the present invention include sports or lifestyle activities.

A change of an environmental condition as meant in accordance with the present invention may be achieved by altering the physical living environment of an organism subjected to the method of the present invention. Environmental conditions such as temperature, illumination period, humidity, oxygen pressure, can be easily altered by techniques well known in the art. Moreover, radiation, including UV radiation, γ-radiation, β-radiation or α-radiation, can also be applied to the organism by techniques well known in the art.

It is to be understood that the aforementioned treatments may be freely combined. Accordingly, treatment as meant herein also encompasses a treatment comprising modification of the genome of an organism (i.e. genetic modification), administration of a compound, e.g. a toxic compound, surgery, changing the environmental conditions by raising the temperature under which the organism is kept and/or finally applying, e.g., UV radiation to the organism or a combination of said treatments.

Also particularly encompassed by the present invention is a method for determining a biomarker specific for a first sample comprising the steps of the method of the present invention and the further step of determining the biomarker based on said trait specific for the said first sample.

As described above, the aforementioned method of the present invention may be also applied to determine a biomarker specific for a first sample. The term "biomarker" as used herein encompasses biological markers based on the said specific traits for the sample analyzed by the method of the present invention which specifically mark biological material with respect to various biologically-related aspects. A biomarker in accordance with the present invention may be a biomarker which specifically identifies an organism or a sample derived there from (e.g. a sample of a particular tissue or cell type, such as a cancer cell or cancerous tissue), indicates a biological source of an organism or a cell, a tissue or an organ thereof, a biomarker for a prevalence for a disease or a disorder or prevalence therefore, a biomarker for a certain efficacy of a drug in an organism, a biomarker for side-effects of various treatments including medical therapies (e.g. drug treatment), a biomarker for toxicity assessments or a biomarker for environmental influences on the physiology of an organism or a cell, a tissue or an organ thereof.

As discussed above, a biomarker as used herein may be, preferably, an indicator for a particular composition of said sample. It is to be understood that a sample which has been derived from a first type of cells, tissues or organs of an organism will differ in its composition in comparison to a second sample obtained from a second type of cells, tissues or organs, wherein said first and second type of cells, tissues or organs shall not be identical. Accordingly, if a biological sample from the heart will be compared to a biological sample from the brain, specific traits for the heart and/or brain may be determined by the method of the present invention, wherein said traits will serve as biomarkers for the respective organ. Moreover, the method of the present invention allows for establishing cell, tissue or organ specific metabolic profiles. A particular composition of said sample as mentioned above may also be the origin or the age of a natural or processed samples, for example the origin of water contaminating fuel samples or the origin or age of foodstuffs as discussed elsewhere in this specification in detail.

If biological samples from two different organisms are compared, a biomarker can be used to identify the organisms. In that case, based on the trait specific for one of said samples, a biomarker can be determined which allows identification of the organism. For example, when comparing two different species of organisms by the method of the present invention, a specific biomarker can be determined based on the trait specific for one of said samples (i.e. the first sample). For example, in environmental samples the determination of microorganisms, such as bacteria and fungi, may in some cases be a cumbersome and time-consuming process. The method of the present invention allows for a rapid identification of microorganisms based on the determination of a specific biomarker therefore. Such a biomarker can be determined by the method of the present invention by comparing a sample comprising unknown microorganisms with a sample or a plurality of samples comprising various different known microorganisms. New microorganisms can be identified based on their metabolome by a trait specific for the first sample while known microorganisms are to be identified on the basis of a common trait in both samples. However, the method of the present invention is not limited to determining of specific traits for samples of different biological material or different organisms. Rather, it further includes determining a trait specific for a first sample, wherein said first sample and the sample compared thereto (i.e. the second sample) are obtained from the same organism prior and after a certain treatment or from organisms of the same species, wherein one organism or group of organisms has been subjected to a certain treatment while the other organism or group thereof was kept untreated or subjected to a different treatment.

In a more preferred embodiment of the aforementioned method of the present invention said biomarker may be a biomarker which is useful for toxicity assessments. Accordingly, the method of the present invention may encompass a comparison of a sample of an organism which has been treated by a compound suspected to be toxic to a corresponding sample of a control organism. A control organism in said case may be an organism to which a compound known to be toxic has been administered. In said case, a common trait may be determined between the two samples which is indicative for a biomarker for toxicity. Alternatively, a sample of an organism may be compared to a control organism to which no compound has been administered. In said case, a biomarker will be determined based on a trait specific for the sample of the treated organism. Moreover, in the latter case, it will be required to observe the organism further for toxic complications. In case such toxic complications arise, the biomarker will specifically indicate toxicity of the compound. Thus, the present invention encompasses further a method for assessing toxicity of a compound comprising the steps of the aforementioned method.

In another preferred embodiment of the aforementioned method, said biomarker is a biomarker for the action of a drug. A drug as used herein encompasses drug candidates, pro-drugs and drugs as such. In principle, the method may be carried out as described for toxicity assessment. However, the biomarker will be indicative for drug action rather than toxicity. Drug action as used herein includes effectiveness as well as mode of action. Accordingly, by applying the aforementioned method, a biomarker may be identified which indicates that a compound is effective as a drug (i.e. a drug can be identified, e.g., in a drug screen, amongst other compounds). Moreover, it is also envisaged that the biomarker may be used to identify the mode of action of a drug or therapeutically effective dosages.

In another specific embodiment of the aforementioned method, a biomarker may be determined which indicates drug efficacy and/or side-effects of drugs. Such a method will be particularly useful for accelerating clinical trials. The method according to this preferred embodiment in principle contains the same steps as mentioned before, wherein the marker, however, is an indicator for drug efficacy and/or side-effects.

Moreover, in accordance with the method of the present invention, biomarkers may be identified and correlated to degrees of efficacy or side effects for a certain drug. These biomarkers may serve as standards based on which suitable therapies or suitable dosages for a drug in a therapy may be determined. Accordingly, a biomarker is also, preferably, used to predict an organism's response to a drug and, therefore, may be used to select a suitable therapy or to support clinical trials and preclinical studies. Accordingly, such a biomarker can be used to define groups of individuals which are expected to respond to the drug in a certain way.

In another preferred embodiment of the aforementioned method, the biomarker will be suitable for diagnostic purposes. Due to the determination of a biomarker as referred to in accordance with the present invention, a disease, disorder or prevalence therefore can be diagnosed. Preferably, a disease or disorder as referred to herein is accompanied by metabolic changes. Such diseases or disorders may be selected from the groups of cardiovascular diseases or disorders, cancer, disorders and diseases of the metabolism, and degenerative diseases or disorders including neurodegenerative diseases. Accordingly, the present invention encompasses further a method for diagnosing a disease, disorder or prevalence therefore comprising the steps of the aforementioned method. It is to be understood that the method may be also used for risk stratification in this context.

Moreover, in further preferred embodiments of the method of the present invention, the biomarker is used to evaluate transplantation efficacy. For example, a biomarker may identify a suitable donor and/or recipient. Alternatively, based on the biomarker, the risk for transplant rejection may be stratified and monitored.

In a further preferred embodiment of the method of the present invention, a biomarker which is determined as described above will be used for determining the metabolic effects of nutrients, nutraceuticals, feed and foodstuff. The biomarker may be used to assess the efficacy of said nutrients, nutraceuticals, feed and foodstuff or to determine possible harmful or toxic side effects (i.e. biocompatibility may be tested). The method of the present invention may be also applied for quality control during the manufacture of nutrients, nutraceuticals, feed and foodstuff (e.g., nutrient or nutraceutical composition, purity etc.) and to ensure or optimise particular properties of the nutrients, nutraceuticals, feed or foodstuff such as taste. Moreover, based on metabolic changes and the corresponding biomarkers, personalized diets may be developed for an organism. The success of said diets may also be monitored by the method of the present invention.

Similarly the method of the present invention may also be applied for quality control or advancement of semi-luxury products like alcohol or tobacco products and their like. Advancement in this context includes better taste and compatibility and the reduction of noxious effects of their consumption.

As described already before in connection with drugs, the biomarker determined according to the method of the present invention will be, preferably, applicable also for determining the effects caused by cosmetics or consumers care products (e.g., diapers or hygiene papers). Toxic or harmful side effects for cosmetics and consumer care products may be identified. Moreover, the efficacy of cosmetics may be determined. The method of the present invention may be also applied for quality control during the manufacture of cosmetics or consumers care products (e.g., product composition, purity etc.) or to ensure or optimise particular properties, such as the specific smell of a perfume.

A biomarker as determined by the aforementioned method of the present invention will in a further preferred embodiment of the method of the present invention be used for lead compound development for herbicides, insecticides or fungicides. Efficacy of lead compounds may be effectively tested at an early stage of product development by analysing the metabolome caused by treating a target organism, e.g. the plant, the insect or the fungus, with the lead and identifying a biomarker as described hereinabove. A suitable biomarker in this case may be based on a trait which has the metabolome affected by the potential lead compound in common with a metabolome of a compound known to be effective as herbicide, insecticide or fungicide.

In another preferred embodiment of the method of the present invention, the biomarker will be applied to identify the health status of a plant (plant diagnostics). Accordingly, the biomarker may be used as an indicator for water, nitrogen or nutrient requirements. Moreover, the biomarker determined by the method of the present invention may be used for monitoring water consumption, nitrogen consumption or nutritional consumption of a plant.

In another preferred embodiment of the method of the present invention, the biomarker may be used for determining the presence or absence or the abundance of an exogenous compound in a biological sample of an organism. Such exogenous compounds include compounds used for doping, such as erythropoietin, or degradation products thereof as well as prohibited drugs, such as heroine or cocaine or degradation products thereof, in a forensic use of the method.

Moreover, the biomarker to be determined by the method of the present invention may be used as an indicator for health risk assessment. For example, the adverse effects of smoking may be monitored and/or investigated. However, the biomarker may also serve to assess the risks or beneficial effects caused by certain sports or a healthy lifestyle. The biomarker may also serve identify disease predispositions.

The biomarker to be identified by the method of the present invention, preferably, is also useful for improving breeding. For example, crop plants having superior properties, such as a higher yield, are usually obtained by breeding. Parent organisms having a phenotype showing the superior properties are crossed with each other or propagated otherwise in order to obtain offspring also having a phenotype which shows the superior properties. The same applies for animals and, in particular, farm animals. Conventional breeding normally takes several generations until a population which homogenously shows the superior properties is obtained. This is a time consuming and cumbersome process. By determining biomarkers which are indicative for the superior properties of organisms of the parent generation, suitable organism from which offspring shall be obtained can be reliably and easily identified. Moreover, the same applies to the individuals of the offspring. Specifically, suitable candidates for further propagation may be identified even though the superior property has not yet been developed by the offspring organism. For example, a higher yield may be determined by conventional methods of breeding only for the mature plant. Based on the biomarker, however, the potential to develop a superior property such as the higher yield may be determined already for the seeds or the young plants prior to maturation.

The present invention also specifically relates to a method for determining a mode of action of a compound administered to an organism comprising the steps of the method of the present invention and the further step of determining the mode of action of said compound based on a trait specific for a first sample of the said organism.

The term "mode of action" as used in accordance with the present invention refers to the capability of a compound, e.g., a toxic compound, a plant protection compound (e.g., fungicidal, herbicidal or insecticidal compounds) or a drug, to influence specific metabolic and cellular enzymatic pathways. Accordingly, due to said influence the metabolome of an organism will change in a specific manner which is indicative for the pathway or pathways which have been influenced by a compound. Influencing a metabolic or cellular pathway as used herein means that the compound may modulate, inhibit or activate specific proteins or regulatory factors for the said pathways. Determining a mode of action as used herein encompasses determining the specific pathway on which a compound acts and identifying said pathway including the identification of the relevant proteins or other factors involved in pathway regulation. Moreover, determining a mode of action also includes determining whether a compound to be analyzed by the method of the present invention acts on the same pathway as a known compound because it elicits the same metabolic changes, i.e. the same metabolome or profile as the known compound. In the latter case, it may not be required to identify the specific pathway or the specific proteins or regulatory factors involved in its regulation. Rather, it might be sufficient to merely assess whether a compound to be analyzed, in principle, may act on the same pathway(s) as a known compound. Such a preferred method is particularly useful for the rapid identification of compounds with a certain mode of action, such as drugs, plant protection compounds or toxic compounds. It is envisaged that, in a preferred embodiment of the method, the metabolome analysis results for mode of actions of compounds, such as drugs, plant protection compounds or toxic compounds, are stored in a suitable database.

By determining a mode of action according to the method of the present invention, plant protection compounds such as drugs, toxic compounds, herbicides, fungicides and insecticides may be identified or improved. Specifically, the mode of action of a test compound suspect to have therapeutic, toxic, herbicidal, fungicidal or insecticidal properties may be compared on the metabolome level to the mode of action of at least one further compound known to exhibit the desired properties. In this context, mode of action analysis on the metabolome level is particular advantageous because compounds with weak activity on their specific pathway or the specific enzymes, proteins or regulatory factors involved in its regulation might not display visible symptoms on the test organism while already showing significant changes in the metabolome as being part of their mode of action. Accordingly, mode of action determination may be indicative for early therapeutic or toxic processes. Metabolome analyses would, therefore, be particular suitable for identification of the aforementioned compounds. Moreover, this approach could be standardized and performed at high throughput to screen for new plant protection compounds. Moreover, the activity of identified compounds could be optimized by chemical modification and retesting on the test organisms. Furthermore, compounds known to exhibit the desired properties (including those identified by other screening approaches) could be improved using the aforementioned method. Metabolomics, thus, would be suitable to guide compound optimization or improvement by displaying that the chemical modifications lead to activities that relate to the same the mode of action.

Therefore, in a preferred embodiment of the aforementioned method for determining a mode of action, said organism is a plant and the compound is an herbicidal compound. Specifically, the method may be used to determine the mode of action of a known herbicidal compound or to identify herbicidal properties of a compound (i.e. identifying a compound as herbicidal compound).

In another preferred embodiment of this method for determining a mode of action, the organism is an insect and the compound is an insecticidal compound. Preferably, the insect to be used in accordance with the method of the present invention is an insect which is harmful for plants, e.g., a grass hopper or a plant louse. The method may be used to determine the mode of action of a known insecticidal compound or to identify insecticidal properties of a compound (i.e. identifying a compound as insecticidal compound).

In a further preferred embodiment of the aforementioned method for determining a mode of action, the organism is a phytopathogenic fungus and the compound is a fungicidal compound. Again, the method may be used to determine the mode of action of a known fungicidal compound or to identify fungicidal properties of a compound (i.e. identifying a compound as fungicidal compound).

It is to be understood that the aforementioned methods are suitable for various purposes including, but not limited to those specifically referred to above.

In another preferred embodiment of the aforementioned methods of the present invention, substantial equivalence of plants is determined based on a common or specific trait. Plants are, e.g., genetically modified in order to improve properties, such as pathogen or herbicide resistance. However, it will be required to test a genetically modified plant for substantial equivalence to its wild type counterpart. Thereby, harmful side effects caused by the genetic modification can be identified. In this preferred embodiment, the above described methods are used to determine the degree of identity between at least two samples from at least two plants, one being genetically modified whereas the other remains will be not unmodified (i.e. wildtype plant). Preferably, two plants are substantially equivalent, if the metabolomes are essentially identical as determined by the method of the present invention (i.e at least one common trait is to be determined). However, it is to be understood that substantially equivalent plants will differ due to the effects of the envisaged genetic modification. For example, if a heterologous gene encoding a heterologous gene product is introduced by the genetic modification, it will be understood that substantially equivalent plants will differ in that the modified plant will further comprise the heterologous gene product (i.e. at least one specific trait may be determined for otherwise identical samples). Moreover, the plants may further differ in that the heterologous gene product may cause metabolic changes which are or have been expected in light of its biological activities.

In a further preferred embodiment of the aforementioned methods of the present invention, manufacturing processes are monitored or controlled based on a common or specific trait. The manufacture of various compounds or products (e.g., food products such as beer) includes fermentation processes. It is required to monitor the manufacturing process (i.e. the fermentation) carefully for quality control, in order to identify obstacles or to monitor progress. By using the methods of the present invention, changes in the composition of a fermentation broth may be efficiently determined. Based on said determination further measures may be started such as abortion of the fermentation process or changes of fermentation conditions. As described before, the methods of the present invention may be assisted by automation. Accordingly, the methods of the present invention may be easily implemented in an automatic manufacturing process.

In another preferred embodiment of the aforementioned methods of the present invention the composition of feed or foodstuffs is determined based on a common or specific trait.

The composition of feed or foodstuffs may be determined in order to ensure constant quality, taste or biocompatibility (e.g., no toxicity etc). The method can be applied to manufactured or naturally occurring feed or foodstuffs.

In a further embodiment of the aforementioned methods of the present invention environmental samples, such as geological samples, will be analyzed for indicators of natural resources based on a common or specific trait. Preferred natural resources to be indicated are oil or gas. Moreover, further processing of oil or gas may be monitored by the method of the present invention.

In a further embodiment of the aforementioned methods of the present invention, environmental samples monitored for environmental pollution based on a common or specific trait. Monitoring encompasses preventive or forensic monitoring. Preventive monitoring may be implemented in order to avoid environmental pollution, e.g., by improperly purified waste water. Forensic monitoring may be applied to identify an environmental pollution and, preferably, also its source.

Also preferably, based on the determination of a common or specific trait for a sample, the methods of the present invention allow monitoring samples, such as environmental samples, for compounds known to be comprised by biological or chemical weapons. The safety on flights, trains, undergrounds and other public transport systems will, therefore, greatly benefit from the present invention.

Finally, the present invention relates to a system, preferably adopted, for carrying out the method of the present invention comprising operatively linked to each other:
a) means for determining a compound;
b) means for monitoring process parameters,
c) means for analyzing raw results obtained from the means according to (a), wherein said means for analyzing raw results comprise:
  (i) a first database comprising raw results received from said means for determining a compound;
  (ii) a second database comprising monitored process parameters;
  (iii) a third database comprising rules for validating the raw results; and
  (iv) a fourth database comprising allocated results of identified compounds;
  (v) a validation tool being capable of confirming or invalidating raw results based on the rules comprised by the said third data base;

wherein at least the second, third and fourth database are operatively linked to the first database.

The term "system" as used herein refers to a plurality of means which are operatively linked to each other in a functional manner. Specifically, the means must be linked in a manner as to allow carrying out the method of the present invention as described in detail above. Therefore, operatively linked, as used herein, preferably, means functionally linked. Depending on the means to be used for the system of the present invention, said means may be functionally linked by connecting each mean with the other by means which allow data transport in between said means, e.g., glass fiber cables, and other cables for high throughput data transport. Nevertheless, wireless data transfer between the means is also envisaged by the present invention, e.g., via LAN (Wireless LAN, W-LAN).

The term "means for determining a compound" as used herein, encompasses means for separating a compound, such as chromatographic devices, and means for compound determination, such as mass spectrometry devices. Suitable devices have been described in detail above. Preferred means for separating a compound to be used in the system of the present invention include chromatographic devices, more preferably devices for liquid chromatography, HPLC, and/or gas chromatography. Preferred devices for determining a compound comprise mass spectrometry devices, more preferably, GC-MS, LC-MS, direct infusion mass spectrometry, FT-ICR-MS, CE-MS, HPLC-MS, quadrupole mass spectrometry, sequentially coupled mass spectrometry (including MS-MS or MS-MS-MS), ICP-MS, Py-MS or TOF.

The means for separating a compound and determining a compound are preferably coupled to each other. Most preferably, LC-MS and/or GC-MS is used in the system of the present invention as described in detail elsewhere in the specification.

The term "means for monitoring process parameters" relates to devices which are capable of measuring individual process parameters. The process parameters which are measured by said devices are preferably process parameters which indicate that the devices used in the process run within normal parameters, i.e. parameters which indicate whether technical obstacles occurred. Moreover, means for monitoring process parameters also include means which calculate recovery rates for certain standards to be used in chromatography. Thereby, it is possible to monitor whether obstacles during chromatography occurred. Moreover, determining encompasses further means for monitoring the efficacy of pretreatments used in the method of the present invention. For example, derivatisation efficacy could be measured by suitable means.

The term "means for analyzing raw results" refers to an analyzing tool and, preferably, a databases as specified above. The analyzing tool may be a computer program which runs on a computer for data processing, data validation and data evaluation. Suitable algorithms for the aforementioned functions are described above in accordance with the embodiments relating to the method of the present invention. A database in accordance with the present invention refers to a collection of information (e.g., results) which is stored on a suitable medium in a systematic way. Said collection of information may be stored on physically identical or separate storage media. If the information is stored on physically separate storage media, it is envisaged that the information stored on each of said media can be allocated to the collection forming the database. Suitable storage media for information include computers or isolated storage media such as hard disks, CDs, CD-ROMs and the like. It is envisaged that the databases referred to in accordance with the present invention have a structure which allows the aforementioned analyzing tool to consult the database, in order to answer queries which arise during processing, validation or evaluation of the results generated in accordance with the method of the present invention. Moreover, the database may further comprise a database management system. Data management systems may be on the basis of a network model, a hierarchical model, a relational model or an object-oriented database model. An alternative database management system may be based on the so-called fuzzy logic.

The term "allocated results of identified compounds" refers to evaluated results which are obtained by known compounds or previously identified compounds. A known compound as used herein is a compound whose chemical nature and composition is prima facie known. An identified compound as used herein may, however, also encompass a compound whose chemical nature and composition is unknown, but which has been observed already in previous analyses using the system of the invention (i.e. so-called known unknown compounds described elsewhere in the specification in detail).

Preferably, the system of the present invention, in principle, operates as follows: The means for determining a compound generate primary raw data. The primary raw data are transferred to the means for analyzing raw data and converted prior to or after said transfer into raw results. The raw results are maintained or stored in a first database as referred to above. The process of compound determination and analysis is furthermore monitored and the measured or determined process parameters are stored in a second database. The analyzing tool of the system of the present invention will now validate the raw results as described in accordance with the method of the present invention above. For example, raw results obtained from samples or sample fractions to which process parameters can be allocated indicating technical inconsistencies will be invalidated. In a subsequent step, the analyzing tool will apply rules, which are derived from a third database, for validating the raw results. Preferred rules to be included in said third database are described elsewhere in this specification in detail. Moreover, depending on the kind of evaluation, the analyzing tool may require another database (fourth database) comprising allocated results of identified compounds which can be compared by applying the rules comprised by the aforementioned rule database by the analyzing tool. The validated and evaluated results may then, optionally, be converted into an output result set which may be stored in a suitable further database or provided in a suitable format for further purposes as specified elsewhere in the specification.

It is to be understood that further databases may be included into the system of the present invention. Thereby, additional information may be allocated to the obtained evaluated results. Moreover, it is envisaged that at least the fourth database referred to in accordance with the system of the present invention is a dynamically operating database, i.e. if new results can be allocated to identified or newly identified compounds, this information will be added to the fourth database.

Accordingly, said first and said fourth database are, more preferably, operatively linked to each other as to allow raw results of the first database to be included as allocated results for identified compounds into the fourth database after evaluation.

In a preferred embodiment of the system of the present invention said means for analyzing raw results comprise:

(v) a fifth database comprising information relating to at least one specific sample identifier operatively linked to at least one other database.

More preferably, said specific sample identifier is selected from the group consisting of: sample number, sample origin, sample source, sample treatment, sample run, and sample aliquot.

Preferably, the fifth database is at least operatively linked to the first database. Said linkage shall allow actualizing correlations or relations between the information relating to the specific sample identifiers and the raw results, validated results or evaluated results obtained from the samples. This is, preferably, achieved by a replication tool using, e.g., PL/SQL procedures for data insertion, deletion and/or update.

In a preferred embodiment of the system of the present invention said means for analyzing raw results comprise:

(vi) a sixth database comprising biochemical information relating to the identifier operatively linked to at least one other database.

The term "biochemical information" as used herein refers to biochemical knowledge known to be associated with the sample identifier. For example, if a sample of a certain cell type, tissue type or organ is analyzed, the identifier may be the sample source and the biochemical information relating to the identifier may be information on a specific biochemical pathway known to be implemented into the cell type, tissue type or organ. Biochemical information includes information derived from the prior art as well as information which is obtained in accordance with the present invention by carrying out additional sample characterization techniques, such as enzymatic assays or other bioactivity studies.

In another preferred embodiment of the system of the present invention said means for determining a compound comprise mass spectrometry devices. Suitable mass spectrometry devices have been described above in detail. Most preferably, the mass spectrometry device to be used in the system of the present invention is a quadruple MS or MS-MS device or a TOF device.

More preferably, said means for determining further comprise liquid chromatography and/or gas chromatography devices. Suitable devices for liquid chromatography including HPLC as well as gas chromatography have been described in detail above.

In a further preferred embodiment of the system of the invention, said system is further comprising means for fractioning a sample.

As described before, the system of the present invention is, preferably, suitable for carrying out the method of the present invention assisted by automation. Accordingly, means for fractioning a sample, preferably, comprise a robot or robot system which is capable of carrying out pipetting and admixing steps.

In another preferred embodiment of the system of the invention, the system comprises further means for extraction.

The means for extraction to be used in the system of the present invention, preferably, comprise an Accelerated solvent extractor (ASE) device for extraction. Moreover, means for extraction may further include a robot or robot device as described above.

All references referred to above are herewith incorporated by reference with respect to their entire disclosure content as well as their specific disclosure content explicitly referred to in the above specification.

The figures show:

FIG. 1: (a) A schematic process of the present invention is shown. In a first step 110, the sample is provided. This step, preferably, includes pre-treatments. The pre-treatments are also carried out for the reference samples, wherein the reference samples and test samples are treated within a defined sequence. In a second step 112, the compounds comprised by the samples are determined. Preferably, the compounds are first separated by a time resolving technique and subsequently determined by a compound analysis technique. This also includes the processing of the primary raw data into suitable raw results for the further analysis. In the third step 114, the raw results obtained by the second step are analyzed. The analysis, preferably, comprises result validation and evaluation.

(b) A schematic view of the monitoring process for process parameters is depicted. The process of FIG. 1a is shown. Process parameters of the devices used for, e.g., extraction and/or fractioning in step 110 are monitored in step 116 during a sample run and stored in a suitable database 118. The monitored process parameters are available for analysis 120 in step 116.

Figure 2:
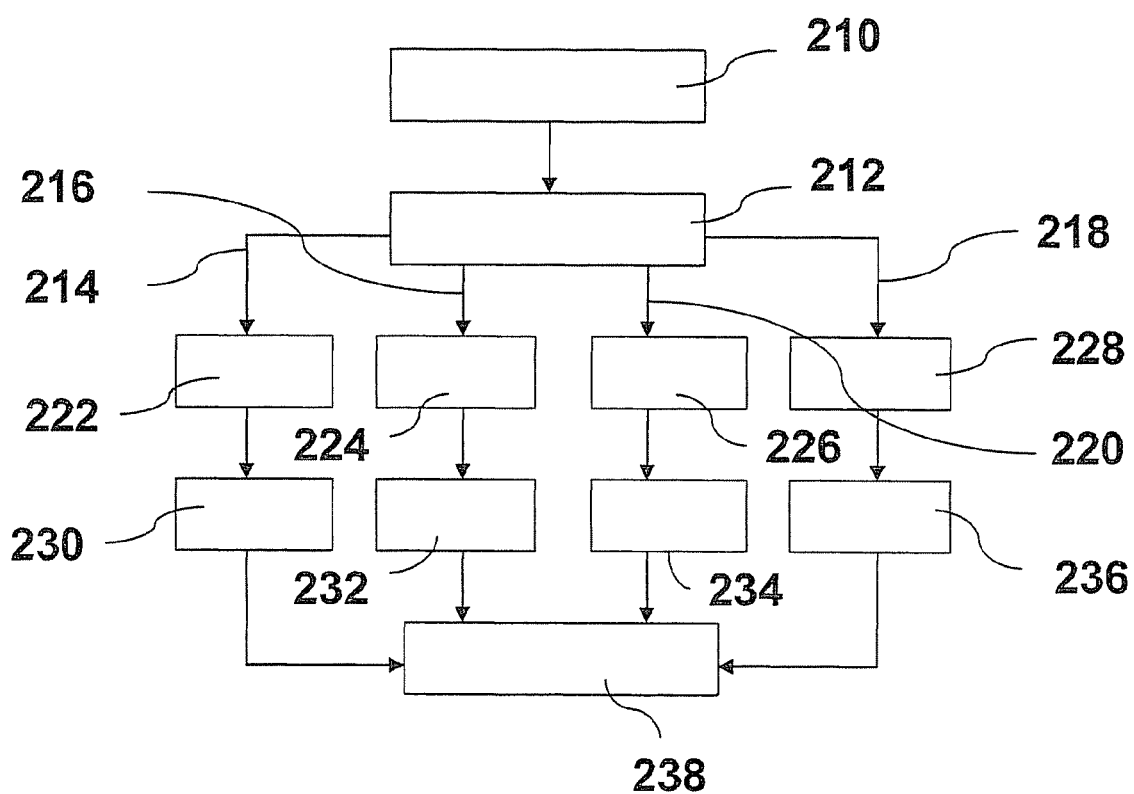

FIG. 2: A preferred method of the present invention is shown schematically. The reference and test samples will be extracted in step 210. Fractioning in step 212 will yield two polar fractions 214, 220 and a non-polar fraction 216, 218 each of which is applied separately to LC 222 and 224 and GC 226 and 228. Preferably, the GC fractions 218, 220 will be derivatised prior to GC as described in the specification and the Examples below. After chromatography, the LC and GC flow through is subjected to MS, 230, 232, 234, and 236. The raw results are further analysed in step 238. Preferably, said analyzing comprises validation of the raw results, normalization of the validated raw results and result evaluation.

Figure 3:
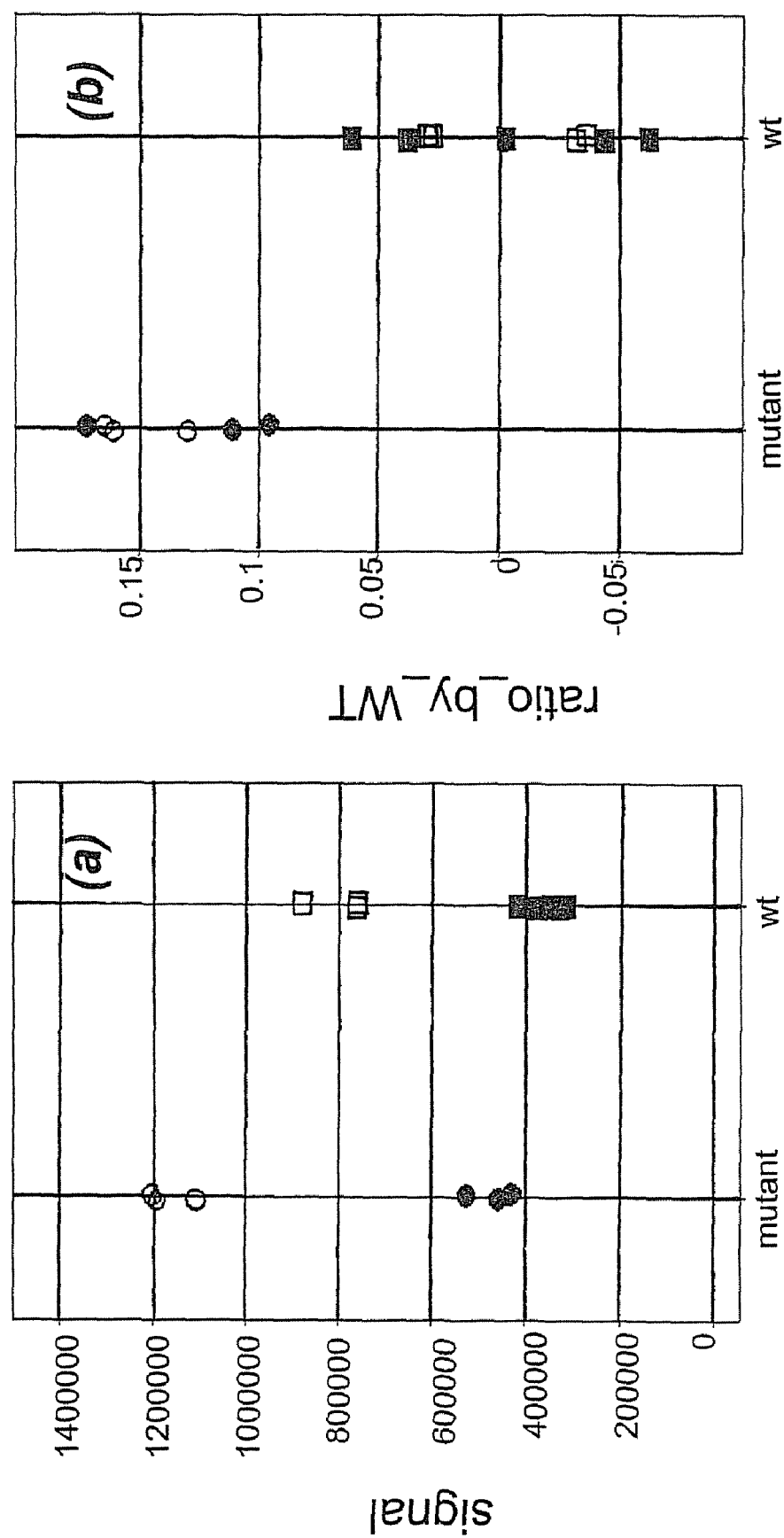
Figure 3:
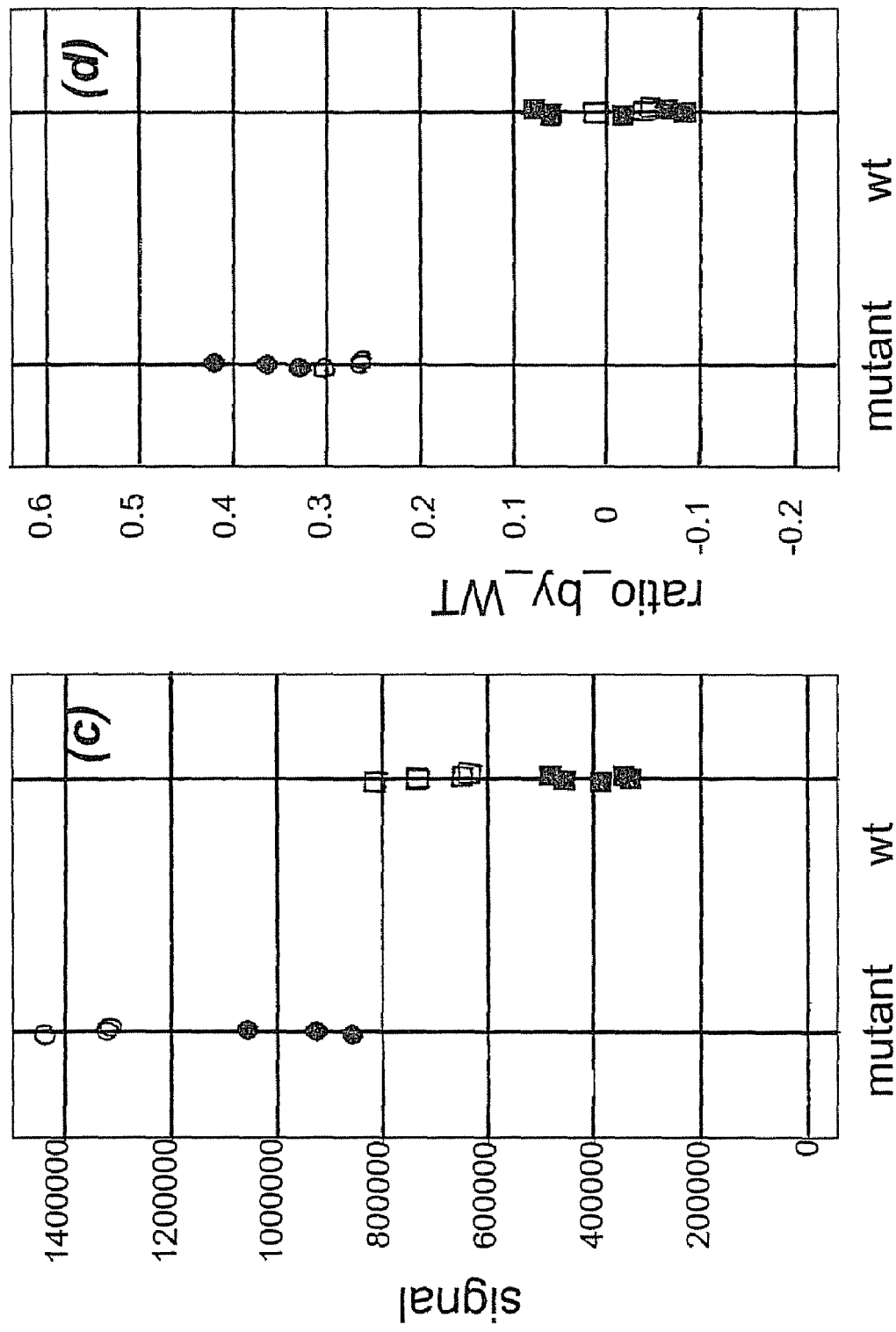

FIG. 3: Data of an analysis of a mutant and a control are shown for two analytes (a) raw results for analyte-1, (b) normalised data (ratio_by_WT) for analyte-1 after log-transformation, (c) raw results for analyte-2, (d) normalised data (ratio_by_WT) for analyte-2 after log-transformation. Open symbols correspond to sequence-1, filled symbols to sequence-2. Data have been jittered slightly to support visualisation of overlapping data FIG. 4: Results of a principal component analysis based on data for 3 analytes measured in 6 mutant and 10 wt samples. (a) pca on raw results, (b) pca on normalised data (ratio_by_WT) after log-transformation. Open symbols correspond to sequence-1, filled symbols to sequence-2. Circles: mutant, squares: wt.

Figure 5:
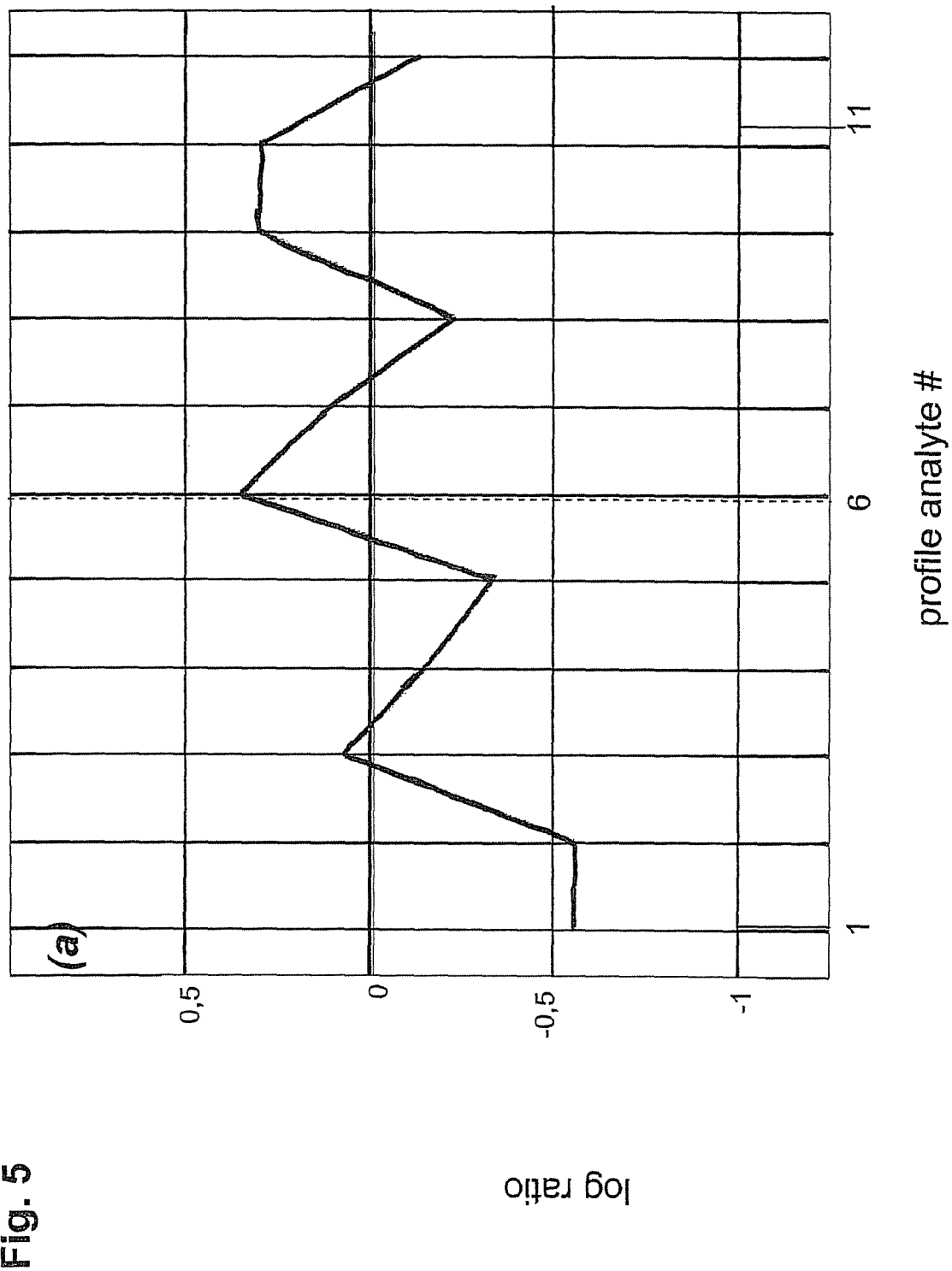
Figure 5:
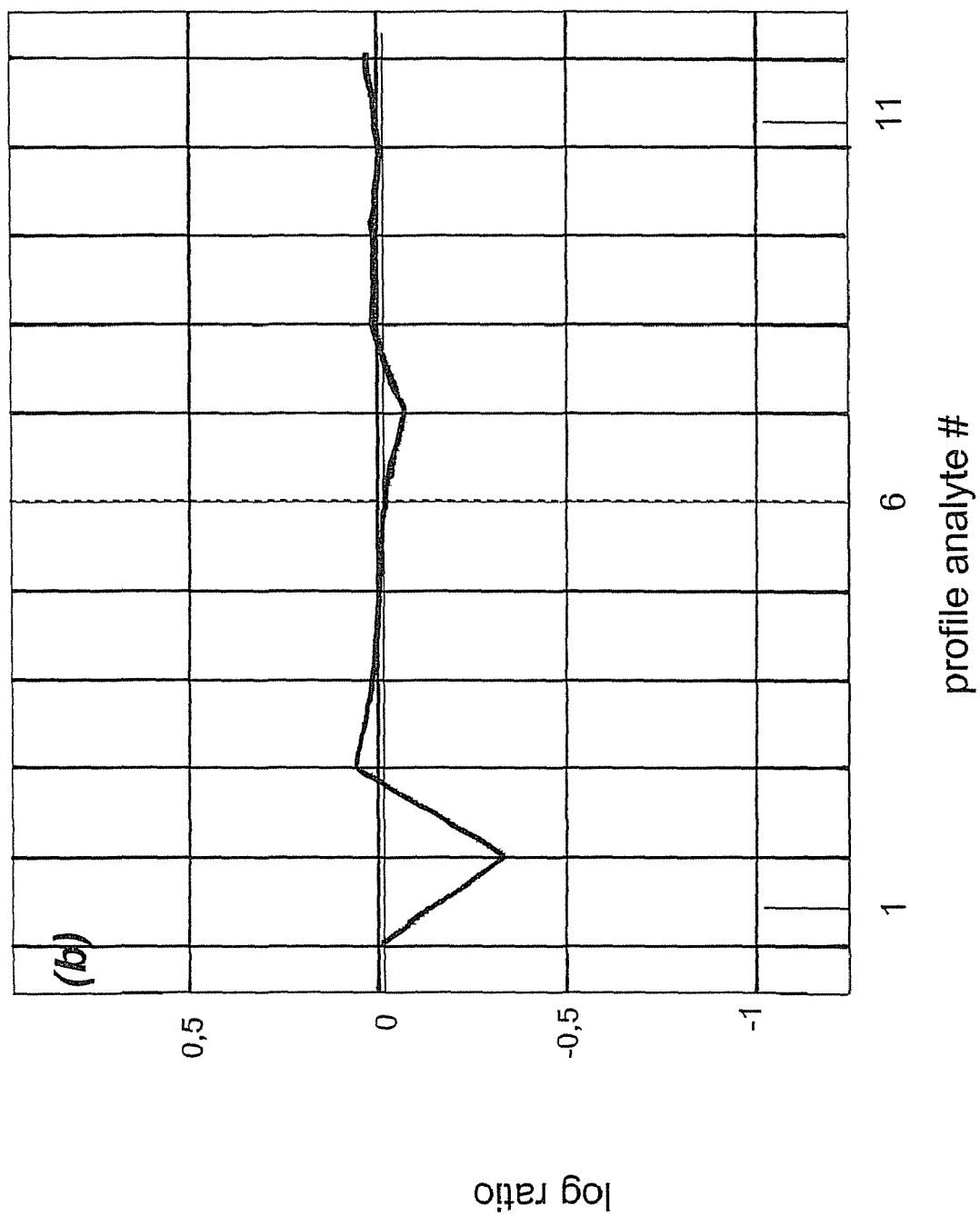

FIG. 5: Biological marker profiles and sample for classification. Characteristic profiles for 11 potential drought stress biomarker analytes are shown. (a) median profile of 8d drought stressed plants, (b) median profile of unstressed plants, (c) profile of a single sample to be classified (sample obtained from a plant that was subjected to 4d drought stress).

FIG. 6: PLS-DA model for sample classification. (a) Normalised and log-transformed data for II potential drought stress biomarker analytes for 20 unstressed and 10 drought stressed plants (8d drought) were used to are build a PLS-DA model. (b) the model obtained in (a) was used to classify a single sample obtained from a plant that was subjected to 4d drought stress. Spheres: 8d drought stressed samples, cubes: unstressed plants, tetrahedron: 4d drought stressed sample.

Figure 7:
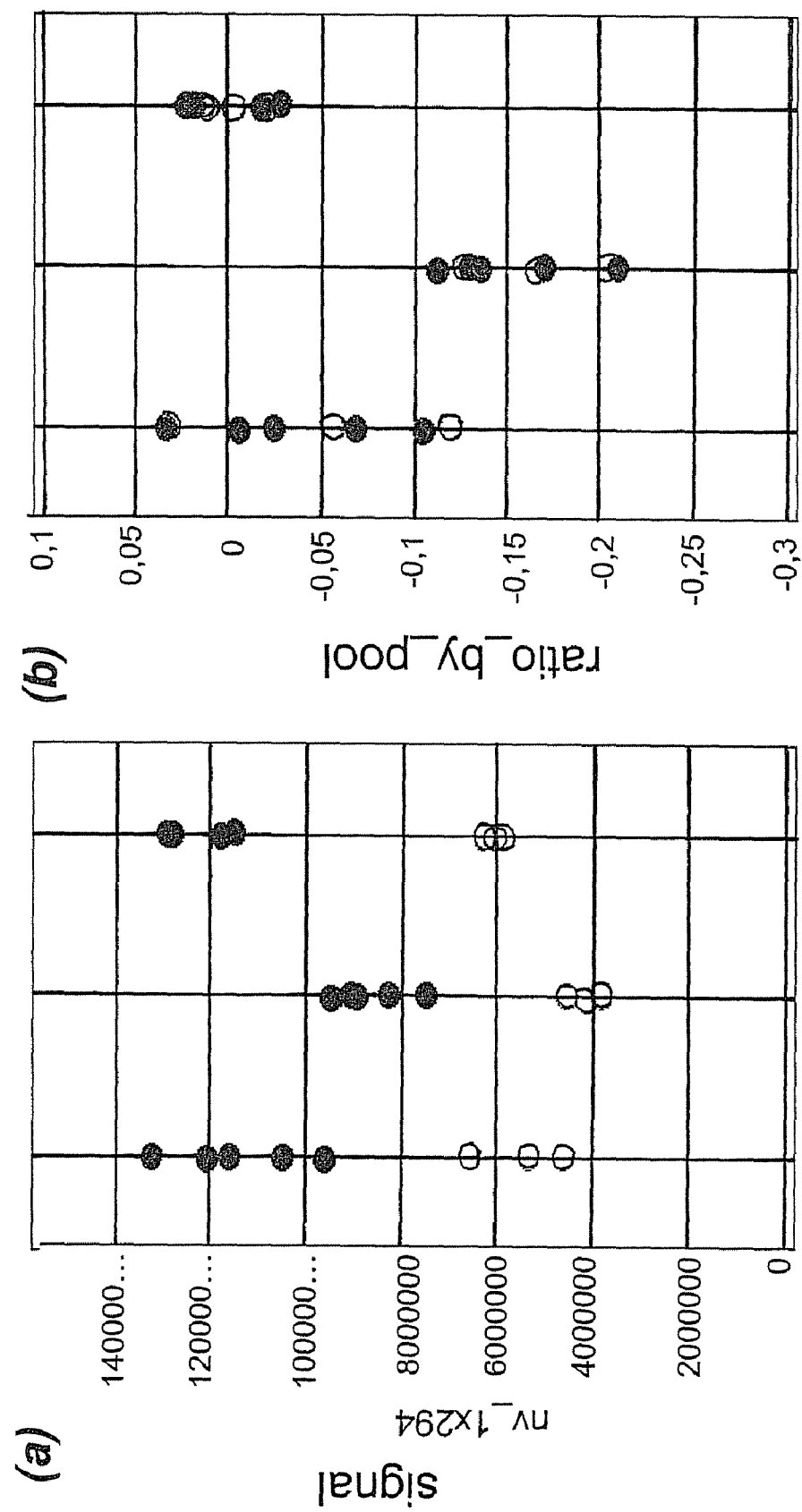
Figure 7:
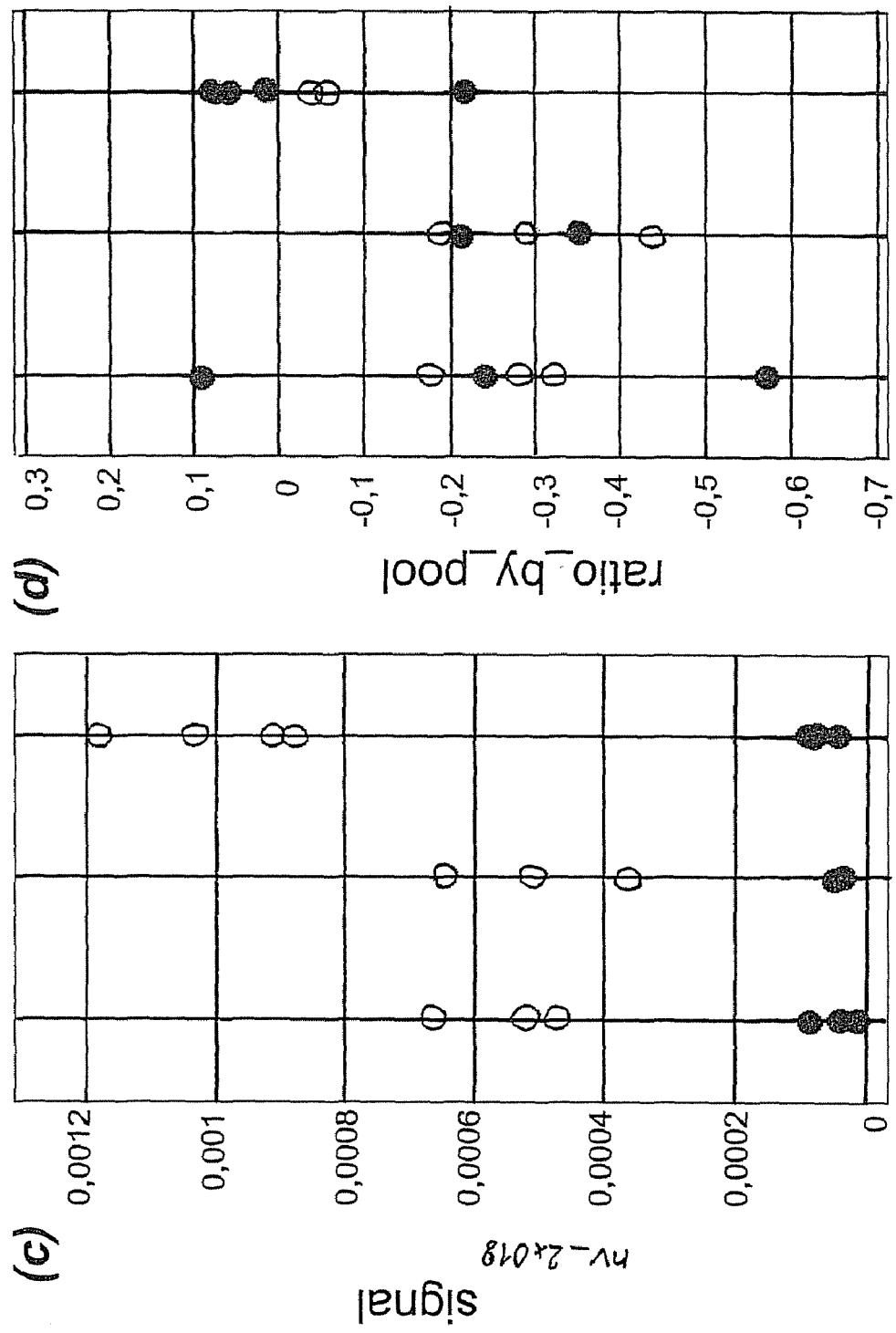

FIG. 7: Data from an analysis of 8 medicated (med), 8 untreated (con) rat blood plasma samples and the corresponding 8 pool references (ref) are shown for two analytes. (a) raw results for analyte-1, (b) normalised data (ratio_by_pool) for analyte-1 after log-transformation (c) raw results for analyte-2, (d) normalised data (ratio_by_pool) for analyte-2 after log-transformation. Open symbols correspond to sequence-1, filled symbols to sequence-2. Data have been jittered slightly to support visualisation of overlapping data points.

FIG. 8: Results of a principal component analysis based on data for 215 analytes measured in 8 medicated, 8 untreated control and 8 pool reference samples. (a) pca on raw results, (b) pca on normalised data (ratio_by_pool) after log-transformation. Open symbols correspond to sequence-1, filled symbols to sequence-2. Spheres: mutant, cubes: wt, tetrahedrons: pool reference.

Figure 9:
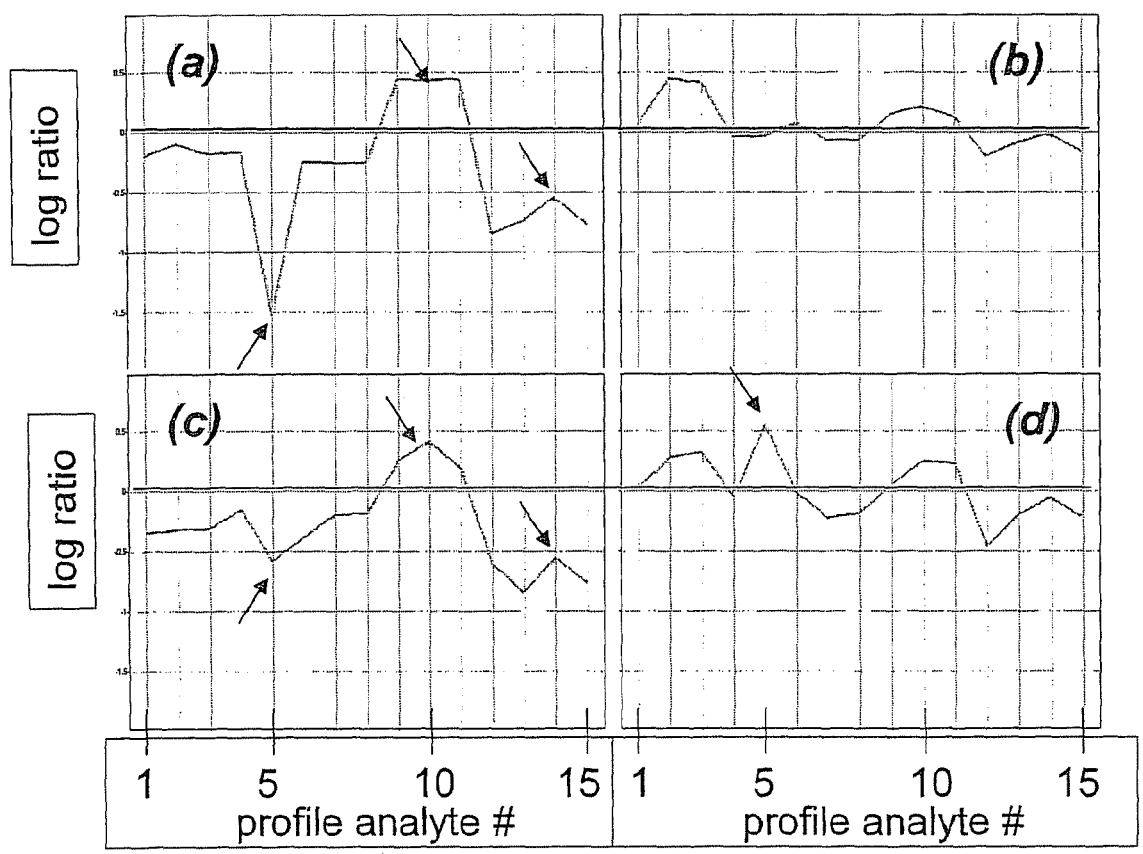

FIG. 9: Biological marker profiles and sample for classification. Characteristic profiles for 15 potential medication-1 biomarker analytes are shown. (a) median profile of medication-1 samples, (b) median profile of untreated control samples, (c) profile of a single sample from medication-2, (d) profile of a single sample from medication-3.

FIG. 10: PLS-DA model for sample classification. (a) Normalised and log-transformed data for 15 potential medication-1 biomarker analytes for 54 untreated control and 14 medication-1 samples were used to build a PLS-DA model. (b) the model obtained in (a) was used to classify a single sample from medication-2, and a single sample from medication-3. Closed spheres: medication-1 samples, closed cubes: untreated control samples, open spheres: medication-2 sample, open tetrahedron: medication-3 sample.

Figure 11:
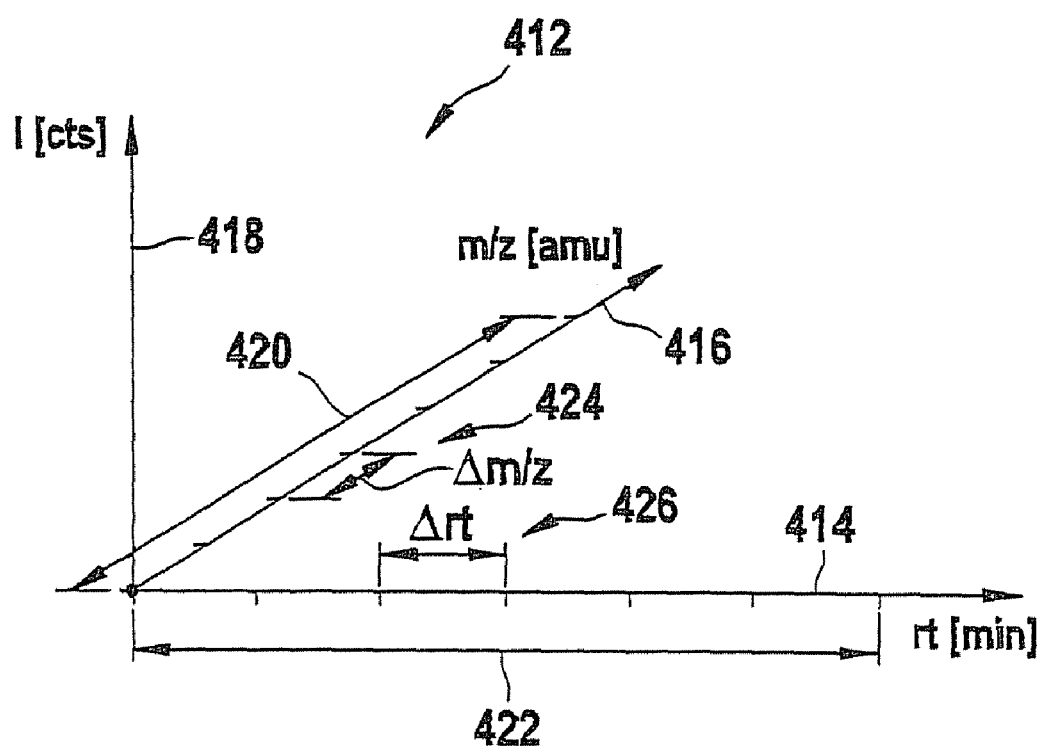

FIG. 11: A coordinate system of a three-dimensional first set of data characterizing a sample containing at least one compound is shown. The reference number will be explained in the Examples.

Figure 12:
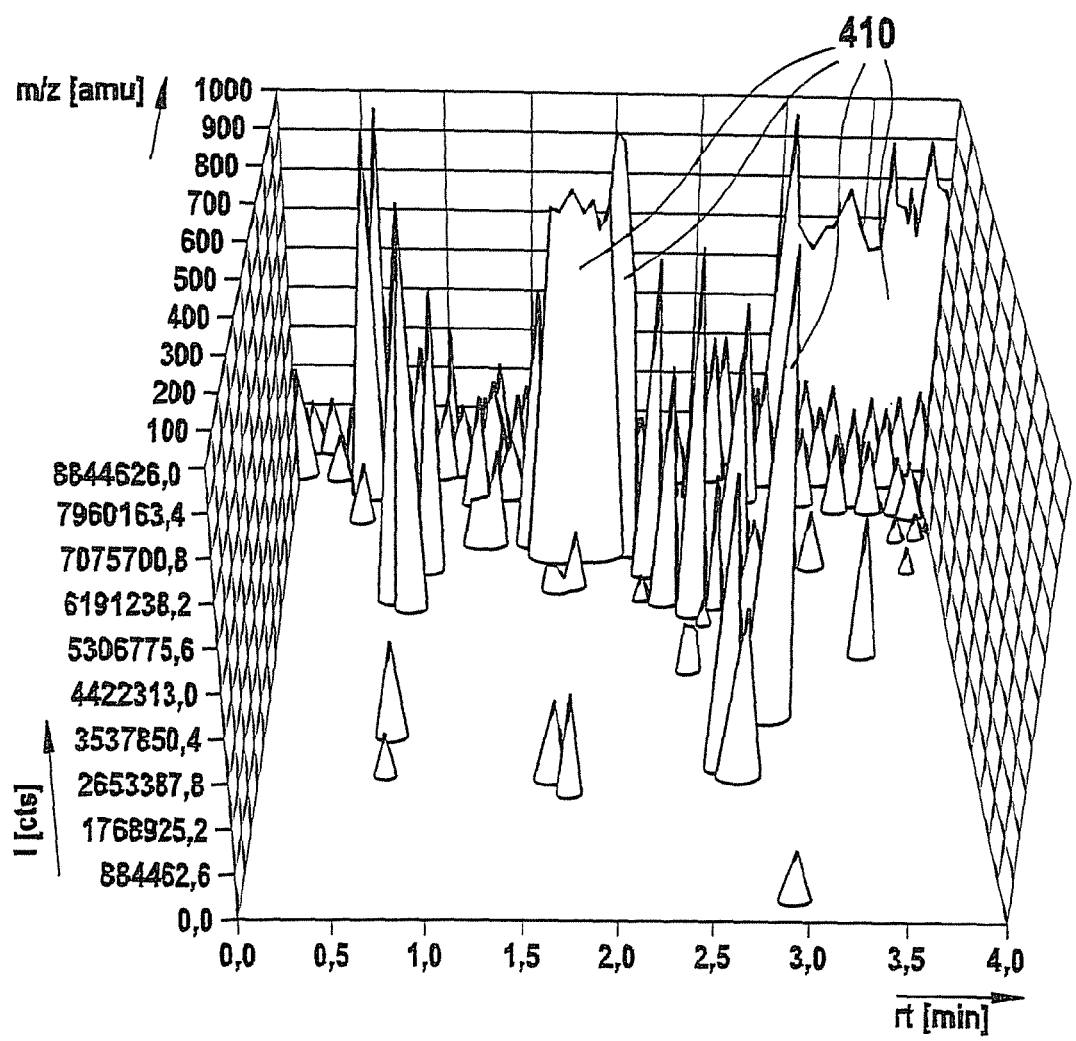

FIG. 12: An example of a three-dimensional first set of data is shown.

Figure 13:
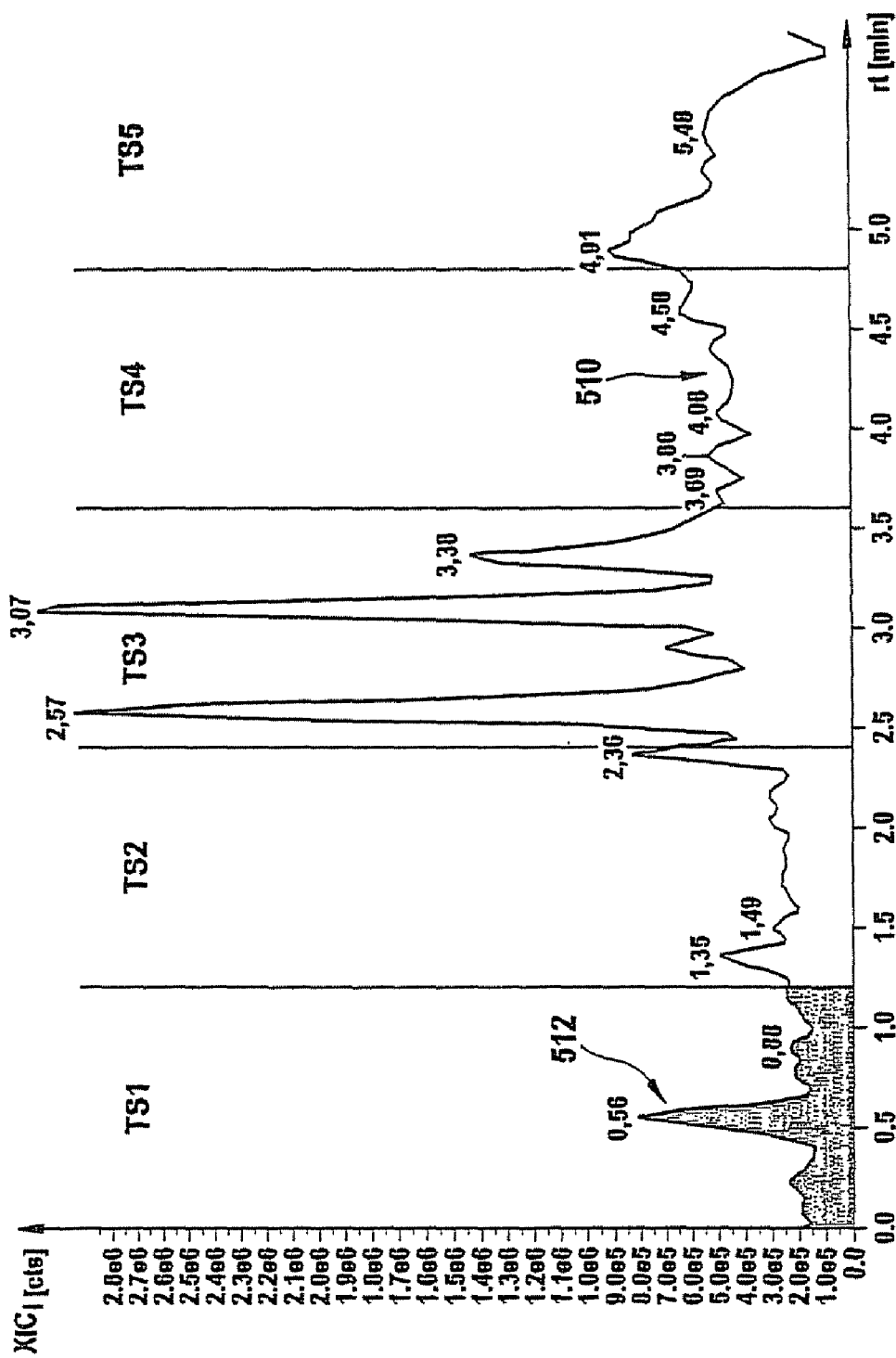

FIG. 13: The principle for creating a specific profile is illustrated. An example of an extracted signal for one specific mass variable interval and the subsequent generation of a characteristic value by intergration of the area under the curve in TS1 is depicted.

Figure 14:
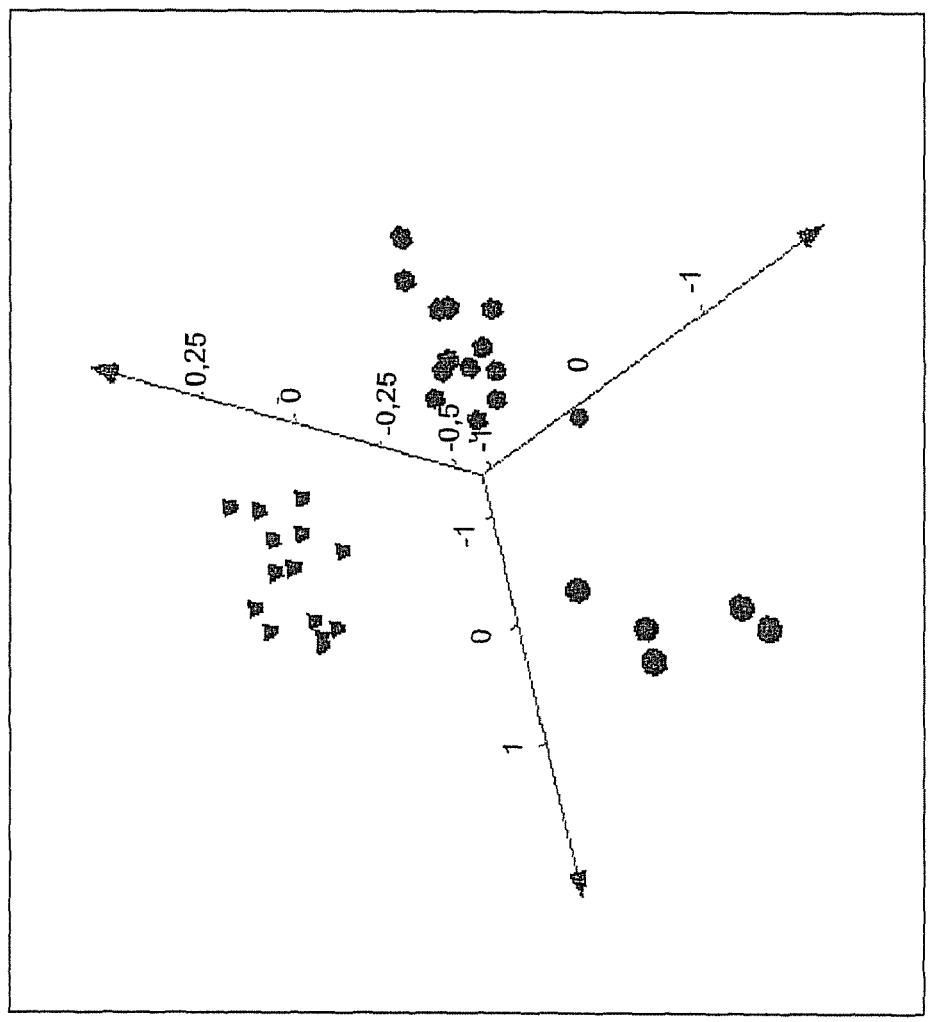

FIG. 14: A first example of the multivariate analysis as part of process step 238 is shown. In particular, the figure shows a 3-dimensional visualisation of the results of a principal component analysis (PCA) based on an anova pre-selection of variables (slices); analysis based on blood plasma from rats subjected to different medications: untreated control rat (tetrahedrons), treatment-1 (spheres), treatment-2 (cubes), the axis represent the first three scores/principal components (t-1, t-2 and t-3)

Figure 15:
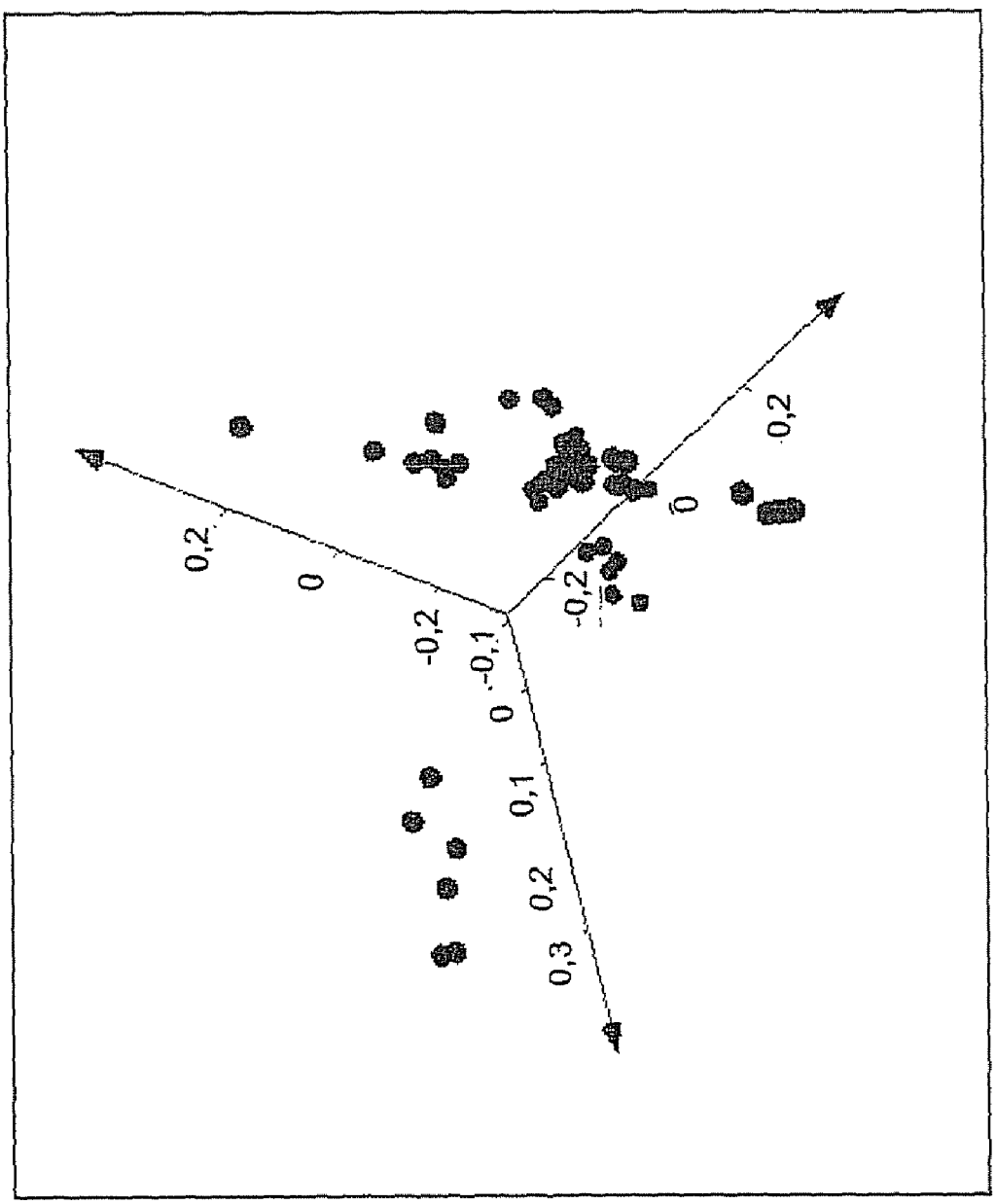

FIG. 15: A second example of the multivariate analysis as part of process step is shown. In particular, the figure shows a 3-dimensional visualisation of the loadings corresponding to the analysis shown in FIG. 14, the axis represent the first three loadings (p-1, p-2 and p-3)

The invention will now be illustrated by following Examples which are not thought to restrict or limit the scope of the invention.

EXAMPLE 1

Metabolic Analysis of Transformed Plants

Transformed (i.e. genetically modified) plants and wild-type plants of *Arabidopsis thaliana* were compared to each other by using the following procedure.

a) Sampling and Storage of the Samples

Sampling was performed directly in the controlled-environment chamber. The plants were cut using small laboratory scissors, rapidly weighed on laboratory scales, transferred into a pre-cooled extraction thimble and placed into an aluminum rack cooled by liquid nitrogen. If required, the extraction thimble can be stored in the freezer at −80° C. The time elapsing between cutting the plant to freezing it in liquid nitrogen amounted to not more than 10 to 20 seconds.

b) Lyophilization

During the experiment, care was taken that the plants either remained in the deep-frozen state (temperatures <40° C.) or were freed from water by lyophilization until the first contact with solvents.

The aluminum rack with the plant samples in the extraction thimbles was placed into the pre-cooled (~40° C.) lyophilization facility. The initial temperature during the main drying phase was −35° C. and the pressure was 0.120 mbar. During the drying phase, the parameters were altered following a pressure and temperature program. The final temperature after 12 hours was +30° C. and the final pressure was 0.001 to 0.004 mbar. After the vacuum pump and the refrigerating machine had been switched off, the system was flushed with air (dried via a drying tube) or argon.

c) Extraction

Immediately after the lyophilization apparatus had been flushed, the extraction thimbles with the lyophilized plant material were transferred into the 5 ml extraction cartridges of the ASE device (Accelerated Solvent Extractor ASE 200 with Solvent Controller and AutoASE software (DIONEX)); see also FIG. 2, 210.

The 24 sample positions of an ASE device (Accelerated Solvent Extractor ASE 200 with Solvent Controller and AutoASE software (DIONEX)) were filled with plant samples, including some samples for testing quality control.

The polar substances were extracted with approximately 10 ml of methanol/water (80/20, v/v) at T=70° C. and p=140 bar, 5 minutes heating-up phase, 1 minute static extraction. The more lipophilic substances were extracted with approximately 10 ml of methanol/dichloromethane (40/60, v/v) at T=70° C. and p=140 bar, 5 minute heating-up phase, 1 minute static extraction. The two solvent mixtures were extracted into the same glass tubes (centrifuge tubes, 50 ml, equipped with screw cap and pierceable septum for the ASE (DIONEX)).

The solution was treated with internal standards: ribitol, L-glycine-2,2-$d_2$, L-alanine-2,3,3,3-$d_4$, methionine-methyl-$d_3$, and α-methylglucopyranoside and methyl nonadecanoate, methyl undecanoate, methyl tridecanoate, methyl pentadecanoate, methyl nonacosanoate.

The total extract was treated with 8 ml of water. The solid residue of the plant sample and the extraction thimbles were discarded.

The extract was shaken and then centrifuged for 5 to 10 minutes at least 1 400 g in order to accelerate phase separation. 1 ml of the supernatant methanol/water phase ("polar phase", colorless) was removed for the further GC analysis, and 1 ml was removed for the LC analysis; see also FIG. 2, 212-220. The remainder of the methanol/water phase was discarded. 0.5 ml of the organic phase ("lipid phase", dark green) was removed for the further GC analysis and 0.5 ml was removed for the LC analysis. All the portions removed were evaporated to dryness using the IR Dancer infrared vacuum evaporator (Hettich). The maximum temperature during the evaporation process did not exceed 40° C. Pressure in the apparatus was not less than 10 mbar.

d) Processing the Lipid Phase for the LC-MS or LC-MS/MS Analysis

The lipid extract, which had been evaporated to dryness was taken up in mobile phase. The HPLC was run with gradient elution as described in example 3b and 3c; see FIG. 2, 214, 222.

The polar extract, which had been evaporated to dryness was taken up in mobile phase. The HPLC was run with gradient elution as described in example 3b and 3c; see FIG. 2, 216, 224.

e) Derivatization of the Lipid Phase for the GC-MS Analysis

For the transmethanolysis, a mixture of 140 µl of chloroform, 37 µl of hydrochloric acid (37% by weight HCl in water), 320 µl of methanol and 20 µl of toluene was added to the evaporated extract. The vessel was sealed tightly and heated for 2 hours at 100° C., with shaking. The solution was subsequently evaporated to dryness. The residue was dried completely.

The methoximation of the carbonyl groups was carried out by reaction with methoxyamine hydrochloride (5 mg/ml in pyridine, 100 µl for 1.5 hours at 60° C.) in a tightly sealed vessel. 20 µl of a solution of odd-numbered, straight-chain fatty acids (solution of each 0.3 mg/mL of fatty acids from 7 to 25 carbon atoms and each 0.6 mg/mL of fatty acids with 27, 29 and 31 carbon atoms in 3/7 (v/v) pyridine/toluene) were added as time standards. Finally, the derivatization with 100 µl of N-methyl-N-(trimethylsilyl)-2,2,2-trifluoroacetamide (MSTFA) was carried out for 30 minutes at 60° C., again in the tightly sealed vessel. The final volume before injection into the GC was 220 µl, see FIG. 2, 220, 226. GC-MS analysis was performed as described in example 2d.

f) Derivatization of the Polar Phase for the GC-MS Analysis

The methoximation of the carbonyl groups was carried out by reaction with methoxyamine hydrochloride (5 mg/ml in pyridine, 50 µl for 1.5 hours at 60° C.) in a tightly sealed vessel. 10 µl of a solution of odd-numbered, straight-chain fatty acids (solution of each 0.3 mg/mL of fatty acids from 7 to 25 carbon atoms and each 0.6 mg/mL of fatty acids with 27, 29 and 31 carbon atoms in 3/7 (v/v) pyridine/toluene) were added as time standards. Finally, the derivatization with 50 µl of N-methyl-N-(trimethylsilyl)-2,2,2-trifluoroacetamide (MSTFA) was carried out for 30 minutes at 60° C., again in the tightly sealed vessel. The final volume before injection into the GC was 110 µl; see FIG. 2, 218, 228. GC-MS analysis was performed as described in example 2d.

g) Analysis of the Various Plant Samples

The samples were measured in individual series of 20 plant samples each (also referred to as sequences), each sequence containing at least 3, preferably 5 wild-type plants as controls. Alternatively aliquots from material derived from a control population can be pooled, thoroughly mixed or homogenized and used as reference. Mass spectrometry was performed using a quadrupole mass spectrometry system; see FIG. 2, 230-238. The peak area of each analyte was divided by the peak area of the respective internal standard. The data were standardized for the fresh weight established for the plant; see FIG. 2, 238.

The values calculated thus were related to the wild-type control group by being divided by the mean of the corresponding data of the wild-type control group of the same sequence. The values obtained were referred to as ratio_by_WT, they are comparable between sequences and indicate how much the analyte concentration in the mutant differs in relation to the wild-type control; see FIG. 2, 238.

Figure 4:
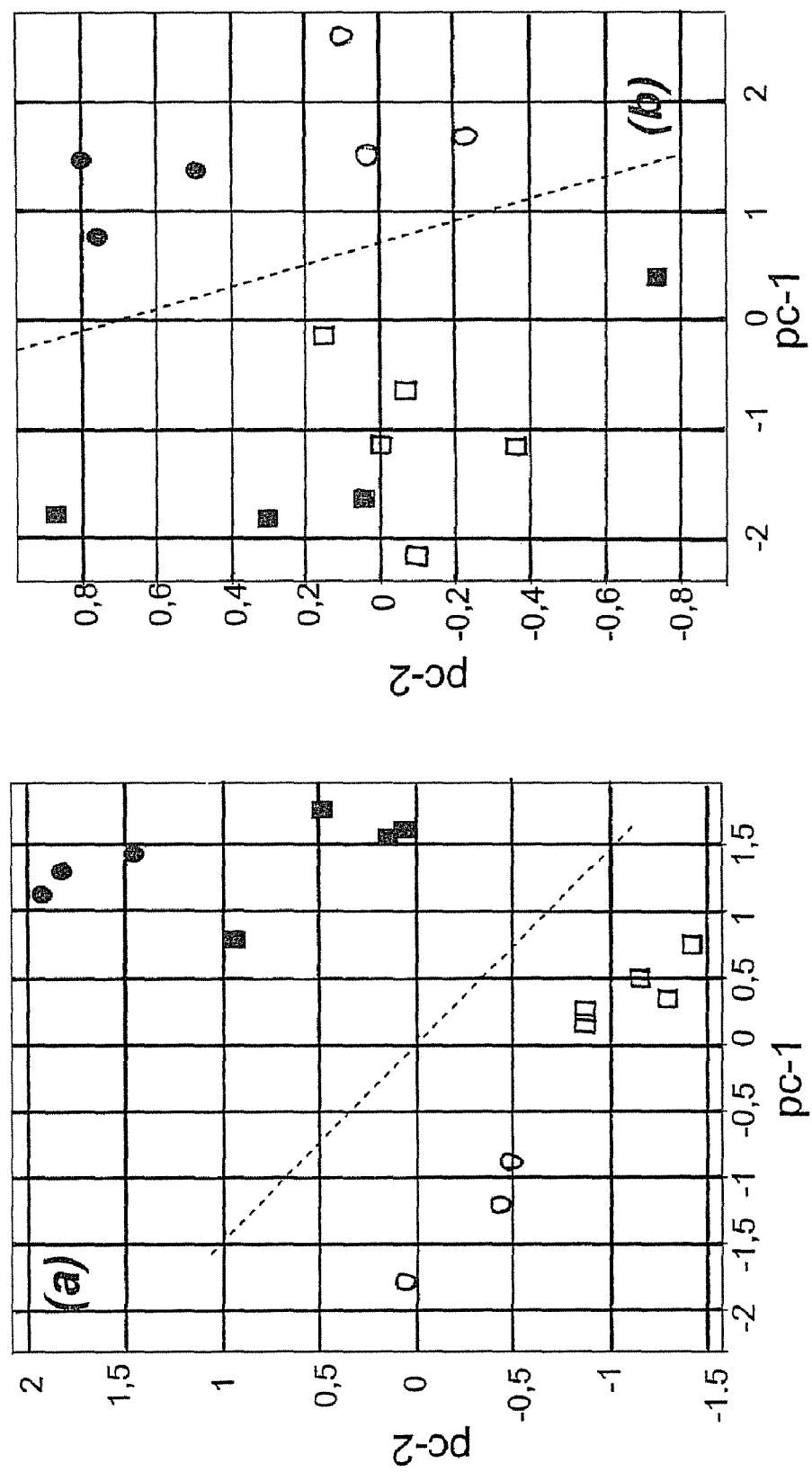

Six individual plants for a knock-out mutant were grown alongside with ten wt control plants under standard plant growth conditions. Analysis of the samples was carried out as described above, with the samples being measured in two independent sequences (three mutants and five wt in each sequence) The corresponding raw data (signals) are shown for two analytes in FIGS. 3a and 3c. Without the normalisation to the wild-type control group differences simply based on technical issues are obvious in the given example (note the within group differences between sequence-1 (open symbols) and sequence-2 (filled symbols)). After normalisation to the mean (as show here or alternatively to the median) of the wt control group the data are much more comparable between sequences (see FIGS. 3b and 3d, note that log-transformed data are shown). This is also reflected in a reduction of the relative standard deviation (rsd, Table 1) his can also be seen in a multivariate analysis FIG. 4). For the multivariate analysis raw results (FIG. 4a) or normalised and log-transformed data (FIG. 4b) for three analytes and six samples for a mutant and nine wt control samples were analysed by PCA. While the principal component analysis separates the samples by their sequence rather than their group assignment if the raw results are used (FIG. 4a), the use of the normalised and log-transformed data is adjusting for the technical effect. In consequence the difference between the groups is becoming the main criteria for separation (FIG. 4b)

TABLE 1

| genotype | analyte | rsd raw results | rsd normalized |
|---|---|---|---|
| mutant | 1 | 0.471 | 0.071 |
| wt | 1 | 0.454 | 0.100 |
| mutant | 2 | 0.215 | 0.132 |
| wt | 2 | 0.318 | 0.133 |

(h) Generating of a Specific Profile 20 plants grown under standard growth conditions and 10 plants grown for two weeks under standard conditions and then subjected to drought stress for 8d (no watering) were harvested, extracted and analysed as described above in a) to e). The obtained raw results were standardized for the fresh weight established for plant and normalised for the mean data of the wild-type control group of the same sequence as described above. The obtained ratio_by_WT data for 160 analytes were log-transformed and analysed by PLS-DA. The 11 analytes with the highest absolute loadings were selected for evaluation as biological marker profile (FIG. 5). FIG. 5a shows the median profile for the drought stressed plants, FIG. 5b the median profile of the unstressed plants and FIG. 5c the profile of a single sample to be classified (this sample was obtained from a plant subjected to 4d drought stress). Comparison of the different profiles indicates that the metabolic marker profile of the drought stressed plants differs significantly from the unstressed profile. The profile of the single sample to be classified shows clear similarity to the stressed profile which indicates that the 4d drought treatment for this sample was sufficient to induce metabolic changes very similar to those seen for severe drought stress.

Another way to use the biomarker profile data for sample classification is shown in FIG. 6. The 11 analytes from the biomarker profile (see above for details) were used to build a PLS-DA drought stress model based on 20 unstressed and 10 drought stressed plants (8d drought) (FIG. 6a). This model was used to visually classify a sample obtained from a plant subjected to 4d of ought stress (FIG. 6b). In the model it is obvious that the 4d drought sample clusters with the 8d drought stressed samples further supporting that 4d drought stress are sufficient to induce metabolic changes very similar to those seen for severe drought stress.

EXAMPLE 2

Generation of a Specific Profile for a Biological Sample

In the following, the steps for establishing a specific profile will be explained for a blood sample based on the results of GC-MS.

a) Sample Preparation

The sample is prepared in the following way: Proteins were separated by precipitation from blood plasma. After addition of water and a mixture of ethanol and dichlormethan the remaining sample was fractioned into an aqueous, polar phase and an organic, lipophilic phase.

b) Derivatization of the Lipid Phase for the GC-MS Analysis

For the transmethanolysis of the lipid extracts a mixture of 140 µl of chloroform, 37 µl of hydrochloric acid (37% by weight HCl in water), 320 µl of methanol and 20 µl of toluene was added to the evaporated extract. The vessel was sealed tightly and heated for 2 hours at 100° C., with shaking. The solution was subsequently evaporated to dryness. The residue was dried completely.

The methoximation of the carbonyl groups was carried out by reaction with methoxyamine hydrochloride (20 mg/ml in pyridine, 100 µl for 1.5 hours at 60° C.) in a tightly sealed vessel. 20 µl of a solution of odd-numbered, straight-chain fatty acids (solution of each 0.3 mg/mL of fatty acids from 7 to 25 carbon atoms and each 0.6 mg/mL of fatty acids with 27, 29 and 31 carbon atoms in 3/7 (v/v) pyridine/toluene) were added as time standards. Finally, the derivatization with 100 µl of N-methyl-N-(trimethylsilyl)-2,2,2-trifluoroacetamide (MSTFA) was carried out for 30 minutes at 60° C., again in the tightly sealed vessel. The final volume before injection into the GC was 220 µl.

c) Derivatization of the Lipid Phase for the GC-MS Analysis

For the polar phase the derivatization was performed in the following way: The methoximation of the carbonyl groups was carried out by reaction with methoxyamine hydrochloride (20 mg/ml in pyridine, 50 µl for 1.5 hours at 60° C.) in a tightly sealed vessel. 10 µl of a solution of odd-numbered, straight-chain fatty acids (solution of each 0.3 mg/mL of fatty acids from 7 to 25 carbon atoms and each 0.6 mg/mL of fatty acids with 27, 29 and 31 carbon atoms in 3/7 (v/v) pyridine/toluene) were added as time standards. Finally, the derivatization with 50 µl of N-methyl-N-(trimethylsilyl)-2,2,2-trifluoroacetamide (MSTFA) was carried out for 30 minutes at 60° C., again in the tightly sealed vessel. The final volume before injection into the GC was 110 µl.

d) GC-MS-Analysis and Generation of Primary Raw Data

The GC-MS systems consist of an Agilent 6890 GC coupled to an Agilent 5973 MSD. The autosamplers are CompiPal or GCPal from CTC.

For the analysis usual commercial capillary separation columns (30 m×0.25 mm×0.25 µm) with different polymethyl-siloxane stationary phases containing 0% up to 35% of aromatic moieties, depending on the analysed sample materials and fractions from the phase separation step, are used (for example: DB-1ms, HP-5ms, DB-XLB, DB-35ms, Agilent Technologies). Up to 1 µL of the final volume is injected splitless and the oven temperature program is started at 70° C. and ended at 340° C. with different heating rates depending on the sample material and fraction from the phase separation step in order to achieve a sufficient chromatographic separation and number of scans within each analyte peak. Furthermore RTL (Retention Time Locking, Agilent Technologies) is used for the analysis and usual GC-MS standard conditions, for example constant flow with nominal 1 to 1.7 ml/min. and helium as the mobile phase gas, ionisation is done by electron impact with 70 eV, scanning within a m/z range from 15 to 600 with scan rates from 2.5 to 3 scans/sec and standard tune conditions.

Blood plasma samples from individual rats subjected to treatment with medication-1 were taken alongside with untreated control rats. All rats were held under standard animal keeping conditions. For use as reference sample(s) blood plasma was pooled from all untreated control animals of the study with four replicates of this pool included in each sequence measured Analysis of the samples was carried out as described above in a) to d). The corresponding raw data (signals) are shown for two analytes in FIGS. 7a and 7e Without the normalisation to the pool reference group differences simply based on technical issues are obvious in the given example (note the within group differences between sequence-1 (open symbols) and sequence-2 (filled symbols)). After normalisation to the mean (as shown here or alternatively to the median) of the pool reference group the data are much more comparable between sequences (see FIGS. 7b and 7d, note that log-transformed data are shown). This is also reflected in a reduction of the relative standard deviation (rsd, Table 2). This can further be seen in a multivariate analysis (FIG. 8). For the multivariate analysis raw results (FIG. 8a) or normalised and log-transformed data (FIG. 8b) for 215 analytes and 8 medication-1 samples, 8 untreated control samples, and 8 pool reference samples were analysed by PCA. The principal component analysis not only separates the samples by their treatment, but rather also by their sequence assignment if the raw results are used (FIG. 8a). The use of the normalised and log-transformed data is adjusting for the technical effect. In consequence the difference between the groups is becoming the main criteria for separation (FIG. 8b).

TABLE 2

| genotype | analyte | rsd raw results | rsd normalized |
|---|---|---|---|
| reference | 1 | 0.363 | 0.045 |
| control | 1 | 0.356 | 0.132 |
| medicated | 1 | 0.344 | 0.083 |
| reference | 2 | 0.940 | 0.197 |
| control | 2 | 0.939 | 0.528 |
| medicated | 2 | 0.863 | 0.226 |

(h) Generating of a Specific Profile

Blood plasma samples from individual rats subjected to treatment with medication-1, medication-2 and medication-3 were taken alongside with untreated control rats. All rats were held under standard animal keeping conditions. At the end of the analysis blood plasma was taken from all animals and pooled for use as pool reference. All samples were taken, extracted and analysed as described above. The obtained raw results were standardized for the extraction volume used and normalised for the mean data of the pool reference of the same sequence (process described above). The obtained ratio_by_pool data for 215 analytes were log-transformed and analysed by ANOVA. The 15 analytes with the highest ANOVA p-values were selected for evaluation as biological marker profile (FIG. 9). FIG. 9a shows the median profile for the medication-1 samples, FIG. 9b the median profile of the untreated control samples, FIG. 9c the profile of a single sample from medication-2 and FIG. 9d the profile of a single sample from medication-3 with the single samples to be classified. Comparison of the different profiles indicates that the metabolic marker profile for medication-1 differs significantly from the untreated control profile. The profile of the single sample from medications shows a similarity to the medication-1 profile indicating that these two medication treatments trigger a similar metabolic response suggesting a similar mode of action. In contrast medication-3 is more similar to the control based on these 15 marker analytes. It should be noted that treatment-3 clearly deviates from the untreated control profile in at least one analyte.

Another way to use the biomarker profile data for sample classification is shown in FIG. 10. The 15 analytes from the biomarker profile (see above for details) were used to build a PLS-DA model for medications versus untreated control based on 54 untreated control samples and 14 medication-1 samples (FIG. 10a). This model was used to visually classify a sample obtained from medications or medication-3 (FIG. 10b) In the model it is obvious that the medication-2 sample clusters with the medication-1 samples further supporting that the two drugs used share a common mode of action. However, the medication-3 sample clusters with the untreated control samples (location at the border suggests some degree of difference).

EXAMPLE 3

Generation of a Specific Profile for a Biological Sample

In the following, the steps for establishing a specific profile will be explained for a blood sample based on the results of LC-MS.

a) Sample Preparation

The sample is prepared in the following way: Proteins were separated by precipitation from blood plasma. After addition of water and a mixture of ethanol and dichlormethane the remaining sample was fractioned into an aqueous, polar phase and an organic, lipophilic phase.

b) Liquid Chromatography

Afterwards, the sample is inserted into a liquid chromatography system, which is coupled to a quadrupole mass spectrometry system. Thus, the sample is first separated by using the time resolved separation technique of liquid chromatography (LC), followed by the mass resolved separation technique of a mass spectrometry. Both systems are controlled by a computer system, which controls the mass spectrometry system as well as the liquid chromatography system and reads out experimental data and system parameters.

The LC part was carried out on a commercially available LCMS system from Agilent Technologies, USA. For polar extracts 10 µl are injected into the system at a flow rate of 200 µl/min. The separation column was maintained at 15° C. during chromatography. For lipid extracts 5 µl are injected into the system at a flow rate of 200 µl/min. The separation column was maintained at 30° C.

c) Mass Spectrometry

The mass spectrometric analysis was performed on a Applied Biosystems API 4000 triple quadrupole instrument with turbo ion spray source. For polar extracts the instrument measures in negative ion mode with ion spray setting 4000 V, gas 1 35 psi, gas 2 30 psi, curtain gas 20 psi and temperature 600° C. The instrument is scanning in fullscan mode from 100-1000 amu in 1 second in fast profile mode with a mass dependent declustering potential starting from −30 V to −100 V. For lipid extracts the instrument measures in positive ion mode with ion spray setting 5500 V, gas 1 25 psi, gas 2 50 psi, curtain gas 25 psi and temperature 400° C. The instrument is scanning in fullscan mode from 100-1000 amu in 1 second in fast profile mode with a mass dependent declustering potential starting from 20V to 110V.

d) Generating a Specific Profile

Thus, by using the system, for each sample a three-dimensional first set of data is generated, which contains a signal (intensity, counts) as a function of a mass-to-charge ratio m/z and as a function of the retention time of the liquid chromatography system.

An exemplary three-dimensional first set of data of a biological sample is depicted in FIG. 12. It can be seen that the raw data contains a number of intensity peaks 410 rising from a horizontal plane. The axes of the data according to FIG. 12 are symbolically depicted in FIG. 11. Thus, the set of axes 412 comprises a retention time axis 414 (denoted by "rt"), wherein the units are minutes. Further, the set of axes 412 comprises a mass-to-charge axis 416, denoted by "m/z", wherein the units are atomic mass units (amu), which actually means "one atomic mass unit per elementary charge". The third axis of the orthogonal set of axes 412 is the signal axis 418, which is denoted by "I" in FIG. 12, wherein the units of the signal axis 418 are, in this example, counts.

Thus, the signal I is a function of the retention time rt and the mass-to-charge ratio m/z. The signal I, in this case, is a discrete function, comprising one signal data point per (MS mass spectrometry) measurement cycle. Nevertheless, as can be seen in FIG. 12, the experimental cycles are small enough with respect to the full range of measurement that the signal I is "smooth" rather than exhibiting discrete steps. Nevertheless, it has to be kept in mind that in reality the signal I is a discrete function, which means, that, when using "integration", in fact a summing of discrete data points is meant.

Further, in FIG. 11, a first range of measurement 420 is depicted, which denotes the range of measurement of the mass spectrometry. Further, a second range of measurement 422 is depicted, which denotes the range of measurement for the chromatography. Thus, mass spectrometry may be performed from, e.g., 100 atomic mass units per elementary charge to 1000 atomic mass units per elementary charge, e.g., in discrete steps of, e.g., 0.2 atomic mass units per elementary charge. Similarly, the second range of measurement 422 may be a range from 0.1 minutes to 6 minutes, in discrete steps of measurement (cycle time) of 1, 2 or 3 second, whereby 1 second is most preferred.

As it is further depicted in FIG. 11, the first range of measurement 420 and the second range of measurement 422 are divided into (in this example) equal intervals 424, 426. Typically, a mass variable interval 424 of a length $\Delta m/z$ of 1 atomic mass unit is preferred, and, for a second range of measurement of 6 minutes, a time variable interval 426 of approximately $\Delta rt=15$ to 80 seconds is preferred, which results in a preferred number of time variable intervals 426 of approx. 5 to 24. More preferably, $\Delta rt=15$ to 20 seconds Preferably, 1 to 20 time variable intervals 426 are used. As noted above, other embodiments of the division of the mass-to-charge axis 416 and of the retention time axis 414 are possible.

In a second process step, an extracted signal (often called extracted ion chromatogram, XIC) is selected for each of the mass variable intervals 424 of the raw data according to FIG. 12. In other words, this step comprises a compression of all raw data within one specific mass variable interval $\Delta m/z$ 424, in order to assign one specific intensity for the specific mass variable interval 424 and for one specific retention time rt. This may, e.g., be done by summing up all intensity signals of the signal I for each retention time for each of the mass variable intervals 424. Thus, e.g., if the mass variable interval 424 referenced to in FIG. 11, is the $i^{th}$ mass variable interval, the extracted signal $XIC_i$ for this $i^{th}$ mass variable interval 424 is:

$$XIC_i(rt)=\Sigma_{\Delta m/z, i} I(rt, m/z). \quad (1)$$

Therein, "$\Delta m/z$, i" denotes a summing over the $i^{th}$ mass variable interval. Thus, the original three-dimensional first set of data I(rt, m/z) is reduced to a plurality of two-dimensional extracted signals $XIC_i$, which are a function of the retention time only. The number of extracted signals $XIC_i$ corresponds to the number of mass variable intervals 424. E.g., if mass variable intervals $\Delta m/z$ of 1 atomic mass unit per elementary charge are used for a range of measurement from 100-1000 amu/z, there is one extracted signal XIC for amu/z=1, one extracted signal for amu/z=101-102, . . . and finally one extracted signal for m/z=999-1000 amu/z. As mentioned above, alternatively to integrating or summing, other methods may be used in order to obtain an extracted signal $XIC_i$ for each mass variable interval 424, such as, e.g., averaging, maximizing or minimizing.

In a next process step, the retention time axis is divided into time variable intervals 426, which are symbolically denoted by "TS 1", "TS 2", . . . , "TS 5" in FIG. 13. In this example, in which the full second range of measurement 422 for a retention time axis 414 is 6 minutes, five time variable intervals are separated, each of a length of 72 seconds. These time variable intervals 426 are often referred to as "time slices".

After dividing the second range of measurement 422 into time variable intervals 426, in a further sub-step, a characteristic value is selected for each time variable interval 426 of the extracted signal $XIC_i$. This process is depicted symbolically in FIG. 13. In this case, the characteristic values are chosen by a simple integration of the extracted signal $XIC_i$ over the $j^{th}$ time variable interval. Since the function $XIC_i$ is, as noted above, in fact a discrete function, this "integration" really is a summing:

$$c_{i,j}=\Sigma_{\Delta rt, j} XICi(rt). \quad (2)$$

Therein, $c_{i,j}$ denotes the characteristic value for the $i^{th}$ mass variable interval 424 and for the $j^{th}$ time variable interval 426. Thus, as a result of process step 414, a matrix of characteristic values $c_{i,j}$ is generated, which is a characteristic sample profile characterizing the sample comprising the at least one compound, and which is a "reduced data set" for the original raw data set (i.e. the signal I).

In a following, optional process step, additional parameters may be obtained from the extracted signal $XIC_i$ in FIG. 13. Alternatively or additionally, the characteristic parameters $c_{i,j}$, as generated according to the method described above, may be transformed, e.g., by normalizing or any other transformation. As an example, the characteristic parameter $c_{i,j}$ for the extracted signal $XIC_i$ depicted in FIG. 13 is symbolically denoted by the black area in FIG. 13, which is the area underneath the extracted signal XICi 510 in FIG. 13 in the first time variable interval TS 1. Since this area strongly depends on the settings of the experimental system, it may, e.g., be normalized to the overall signal height. Thus, the area obtained by using formula (2), generating the characteristic parameters $c_{i,j}$, may be, divided by the height of the highest peak 512 in time variable interval 426. Thus, the characteristic parameters $c_{i,j}$ may be replaced by new characteristic parameters $c_{i,j}'$, which are the characteristic parameters $c_{i,j}$, divided by the height of the peak 512. Thereby, the characteristic parameters are "normalized" and become nearly independent of the experimental settings of the experimental system.

In an optional process step, e.g., a median, a mean value, a standard deviation (SD), a relative standard deviation (RSD) or other statistical values for the samples may be generated and the data might be transformed e.g. by a logarithmic transformation. Thus, several samples may be compared and/or combined, in order to obtain statistical information of the samples.

In a further optional process step, the statistical data may be visualized, in order to visualize the distribution of certain characteristic values over a large number of samples. Thus, e.g., samples and/or characteristic values which deviate from a mean value by more than a predetermined "allowable" deviation may be eliminated from the data set. In a further optional process step, the statistical results of the previous process steps for the characteristic values of the sample or the plurality of samples are compared to reference values, e.g., reference values of a (real or virtual) reference sample. Thus, e.g., by generating the ratio between any certain characteristic value (which may, as indicated above, e.g., be a mean value of a plurality of samples) the likelihood for the presence, absence or amount of a certain chemical compound within the sample or the plurality of samples may be obtained. Thus, a quantitative and/or qualitative analysis of the sample or plurality of samples may be performed.

FIGS. 14 and 15 show examples of results from the previous step. Data from blood plasma samples from untreated and medicated rats (two different medications, subset of the treatments used in the analysis, result visualised for 33 samples) were subjected to a principal component analysis (PCA) that was based on a variable pre-selection (52 variables) derived from an ANOVA analysis. As can be seen in FIG. 14, all three different treatments can be separated and the key variables driving this separation can be identified (FIG. 15).

The results of the process steps described above, such as the characteristic values for each sample, may be stored within the computer system. This computer system may comprise several separate computers, and may comprise one or more databases. Thus, separate computers for controlling the experimental systems and for evaluation of the experimental data may be used. Thus, the experimental data obtained by the process steps described above may be evaluated on a separate computer system.

EXAMPLE 4

Animal Keeping a) Animal Compilation

Rats of the strain CrlGlxBrlHan:Wi were purchased from Charles River, Sulzfeld, Germany having an age of 63 to 65 days. Each animal has been labelled by an ear tattoo, consecutively. Animals were kept under the following housing conditions:

b) Housing Conditions

| | |
|---|---|
| Air conditions: | Temperature 20-24° C., humidity 30-70%. Any deviations have been documented. |
| Illumination period: | 12 hours light from 6.00 to 18.00 hours, 12 hours darkness from 18.00 to 6.00 hours |
| Type of cage: | Wire cages, type DK III, BECKER & Co., Castrop-Rauxel, Germany |
| No. of animals per cage: | 1 |
| Type of diet: | Ground Kliba mouse/rat maintenance diet "GLP", meal, supplied by Provimi Kliba SA, Switzerland, ad libitum |
| Watering: | Drinking water ad libitum |
| Acclimatization: | During the 7 day acclimatization period, the animals have been accustomed to the environmental conditions of the study and to the diet. |

EXAMPLE 5

Administration of Test Compounds and Sampling a) Administration of Test Compounds Male and female wistar rats have been randomized and allocated to the dose groups before the beginning of the administration period on the basis of their weights. The animals have been treated with five different test compounds at a high and low dose level according to the following schedule shown in Table 3.

TABLE 3

| Dose group | Test substance | Dose level (ppm in the diet) | No. of animals per sex | Animal no. males | Females |
|---|---|---|---|---|---|
| 00 | 0 | 0 | 10 | 1-10 | 61-70 |
| 01 | A | Low dose | 5 | 11-15 | 71-75 |
| 02 | A | High dose | 5 | 16-20 | 76-80 |
| 03 | B | Low dose | 5 | 21-25 | 81-85 |
| 04 | B | High dose | 5 | 26-30 | 86-90 |
| 05 | C | Low dose | 5 | 31-35 | 91-95 |
| 06 | C | High dose | 5 | 36-40 | 96-100 |
| 07 | D | Low dose | 5 | 41-45 | 101-105 |
| 08 | D | High dose | 5 | 46-50 | 106-110 |
| 09 | E | Low dose | 5 | 51-55 | 11-115 |
| 10 | E | High dose | 5 | 56-60 | 116-120 | b) Blood Sampling

Blood sampling was carried out as indicated in the following time schedule shown in Table 4.

TABLE 4

| Date | Phase of study/Examination | Date of study |
|---|---|---|
| | Experimental starting date: Arrival of the animals and start of acclimatization period | −6 |
| | Randomization of the animals | |
| | Start of administration period | 0 |
| | Blood sampling | 7 |
| | Blood sampling | 14 |
| | Blood sampling and necropsy | 28 |
| | Blood sample preparation | |
| | Evaluation of the clinical findings | |
| | Summary of the clinical results | |

During the experiment, a check for moribund and dead animals has been made twice, daily from Monday to Friday and once daily on Saturday, Sunday and public holidays. The animals will be checked daily for any clinical abnormal signs. Abnormalities and changes will be documented for each animal. The food consumption has been determined on study days 6, 13, 20 and 27. Drinking water consumption has been checked daily within the general observations. Body weight has been determined before the start of the administration period, in order to randomize the animals. During the administration period the body weight has been determined on study days 0, 6, 13, 20 and 27. The mean daily intake of the test substances have been calculated based upon individual values for body weight and food consumption. Means and standard deviations have been calculated using Dunnet's test.

Blood sampling was carried out as follows: Before necropsy or blood sampling, food was withdrawn for about 16 to 20 hours (fasting period). Blood sampling was done between 7:30 and 10:30 a.m. Blood was taken from the retroorbital venous plexus of isoflurane anaesthesized animals. 1 ml of blood was collected with EDTA as anticoagulant (10 ul of a 10% solution). Samples were centrifuged and plasma was separated. The precipitated cells were washed three times with 0.9% NaCl, and filled up ad 1 ml with sterile distilled water (Ampuwa, purchased from Fresenius, Bad Homburg, Germany). Hemoglobin was determined in hemolyzed blood samples using 40 ul hemolysate and 160 ul 1.5% NaCl. Samples preparation was done under cooling. Samples were stored at −80° C. under nitrogen atmosphere.

After completion of the experiment, clinical pathology for each animal was determined. To this end all animals which survived the study have been sacrificed by decaptation under isoflorane anaesthesia (if final blood sampling was envisaged) or by $CO_2$ anaesthesia.

EXAMPLE 6

Plant Culture for Bioanalytical Analyses

For the bioanalytical analyses of the transgenic plants, the latter were grown uniformly in a specific culture facility. To this end the GS-90 substrate as the compost mixture was introduced into the potting machine (Laible System GmbH, Singen, Germany) and filled into the pots. Thereafter, 35 pots were combined in one dish and treated with Previcur. For the treatment, 25 ml of Previcur were taken up in 10 l of tap water. This amount was sufficient for the treatment of approximately 200 pots. The pots were placed into the Previcur solution and additionally irrigated overhead with tap water without Previcur. They were used within four days.

For the sowing, the seeds, which had been stored in the refrigerator (at −20° C.), were removed from the Eppendorf tubes with the aid of a toothpick and transferred into the pots with the compost. In total, approximately 5 to 12 seeds were distributed in the middle of the pot.

After the seeds had been sown, the dishes with the pots were covered with a matching plastic hood and placed into the stratification chamber for 4 days in the dark at 4° C. The humidity was approximately 90%. After the stratification, the test plants were grown for 22 to 23 days at a 16-h-light, 8-h-dark rhythm at 20° C., an atmospheric humidity of 60% and a $CO_2$ concentration of approximately 400 ppm. The light sources used were Powerstar HQI-T 250 W/D Daylight lamps from Osram, which generate a light resembling the solar color spectrum with a light intensity of approximately 220 μE/m2/s-1.

EXAMPLE 7

Lemna and Arabidopsis Treatment for Bioanalytical Analyses

For the Lemna bioassay, stock cultures of *Lemna paucicostata* L. were propagated mixotrophically in an inorganic medium containing sucrose (10 g litre$^{-1}$), according to Grossmann 1992, Heterotrophic plant cell suspension cultures for monitoring biological activity in agrochemical research. Comparison with screens using algae, germinating seeds and whole plants. *Pestic Sci* 35: 283-289 and Retzlaff 1993, Growth rate determination of *Lemna* by video scan of the leaf surface area. In Target Assays for Modern Herbicides and Related Phytotoxic Compounds, P. Böger, G. Sandmann, eds., pp 251-256, Lewis Publishers. The bioassay was conducted under aseptic conditions in plastic Petri dishes (5 cm in diameter) in 3 replications. Each Petri dish contained 15 ml medium without sucrose and Lemna fronds, which covered ⅔ of the Petri dish area.

The test compounds were added to the medium in acetone solution (1% final concentration of acetone). Controls received corresponding amounts of acetone alone, with no adverse effect on the growth of the plants. Each compound was tested in three concentrations, for example the herbicide chlorsulfuron in final concentrations of 10-5, 10-6, 10-7 M. The culture dishes were then closed with plastic lids and incubated under continuous light (Philips TL white neon tubes, 40 μmol m$^{-2}$ s$^{-1}$ photon irradiance, 400 to 750 nm) in a growth chamber at 25° C. At 48 and 72 hours after treatment, Lemna plants of parallel dishes were harvested (ca. 250 mg fresh weight derived from 3 replications), carefully washed in water, immediately frozen in liquid nitrogen and stored at −80° C. until extraction and analysis of the plant material. Analysis was carried out as described in Example 1.

*Arabidopsis* plants of ecotype C24 were grown as described in example 6. Plants were treated approximately 21 days after germination with the appropriate active substances. The application rate depended on the active substances, for example the herbicide chlorsulfon was tested in amounts corresponding to 1000 g/ha, 250 g/ha and 62.5 g/ha. The treatment was performed with solutions of 1.25 mg/ml, 0.3125 mg/ml and 0.078 mg/ml substance solved in distilled water containing 0.1% Wettol LF-700 (BASF AG, Germany) and 1% DMSO. The solutions were each sprayed on 2 times 3 pots with a diameter of 6 cm containing 3 plants. 1-3 plants representing a total sample weight of approximately 300 mg were harvested 24 and 48 hours after the treatment. Control plants were treated in the same way with a mock solution, not containing the active substance. Metabolic analysis of treated and control samples were performed as described in Example 1.

The invention claimed is:

1. A method for analyzing a test sample, wherein the test sample comprises at least one compound, the method comprising:
    a) providing a test sample comprising at least one compound;
    b) determining the at least one compound in the test sample using chromatography coupled mass spectrometry, thereby generating primary raw data;
    c) generating raw results from the generated primary raw data by (i) deconvolution of the primary raw data and allocation of the deconvoluted primary raw data to compounds using a reference spectrum and a reference retention index and (ii) allocating intensities and retention times to compounds using predetermined ion masses and time windows; and d) analyzing the generated raw results by validation of the raw results using a validation tool adapted to confirm or invalidate the raw results based on a set of rules, thereby generating a set of validated results, wherein the analysis of the test sample is accompanied by an analysis of at least one reference sample, and wherein the test sample and the reference sample are analyzed in an identical sequence in each step of the method.

2. The method of claim 1, wherein the method is assisted by automation.

3. The method of claim 1, wherein the set of rules comprises: (a) determining for each raw result obtained by procedure (i) and (ii) in step c) whether the retention time (RT) provided for a raw result of a compound is within predetermined limits, if the retention time is outside the limits, the raw result is to be invalidated; (b) determining for each raw result obtained by procedure (i) and (ii) in step c) whether the mass spectral match quality of the raw result of a compound in comparison to a predetermined reference result is above a predetermined limit, if the match quality is below the limit, the raw result is to be invalidated; (c) determining for each raw result obtained by procedure (i) and (ii) in step c) whether the retention index (RI) provided for a raw result of a compound is within predetermined limits, if the retention index is outside the limits, the raw result is to be invalidated; and (d) determining for each raw result obtained by procedure (i) and (ii) in step c) whether a raw result for a compound is allocated to a validated raw result of a compound to be used for normalization, if the raw result for the compound to be used for normalization is invalid, the raw results allocated thereto are invalidated.

4. The method of claim 3, further comprising at least one rule selected from the group consisting of:
(a) determining whether the retention time provided for a raw result of a compound obtained by procedure (i) (RT1) and the retention time provided for the same raw result by procedure (ii) (RT2) are within predetermined limits, if one of the retention time is outside the limits, the raw result is to be invalidated;
(b) determining whether the retention index (RI1) provided for a raw result of a compound obtained by procedure (i) and the retention index (RI2) provided for the same raw result by procedure (ii) are within predetermined limits, if one of the retention index is outside the limits, the raw result is to be invalidated;
(c) using the raw result having the largest value for the area under a curve generated by the data points in case a compound has been allocated in step c) to more than one raw result after applying the other rules comprised by the rule database;
(d) determining for each raw result obtained by procedure (i) and (ii) in step c) whether a retention index of a raw result is within predetermined limits based on a retention index standard for linear modeling, if the extrapolated retention index is outside the limits, the raw result is to be invalidated;
(e) determining for each raw result obtained by procedure (i) and (ii) in step c) whether a raw result for a compound has a predetermined valid neighbor raw result within a predetermined retention time or retention index range and a predetermined elution order, if no such valid neighbor raw result exists, the raw result is to be invalidated; and
(f) determining for the each raw result obtained by procedure (ii) in step c) whether the area under a curve generated by the data points of the raw result does not have a negative value, whereby a raw result having a negative value is to be invalidated.

5. The method of claim 1, wherein analyzing the generated raw results further comprises generating a specific profile for the test sample based on the set of validated results.

6. The method of claim 1, wherein the at least one reference sample is selected from the group consisting of:
a. a reference sample comprising a portion of at least one test sample;
b. a reference sample comprising a plurality of defined reference standards;
c. a reference sample comprising a portion of the reference sample (a) and a portion of the reference sample (b).

7. The method of claim 1, wherein the test sample and the reference sample are analyzed in an identical sequence order.

8. The method of claim 7, wherein the sequence order is established prior to analysis of the samples by random positioning of the test sample and the at least one reference sample within the sequence order.

9. The method of claim 1, wherein analyzing the generated raw results further comprises normalization of the validated raw results of the test sample with respect to the validated raw results obtained for the reference sample.

10. The method of claim 1, wherein the method further comprises monitoring of process parameters for the method.

11. The method of claim 10, wherein the validation in step d) further comprises confirming or invalidating raw results based on the monitored process parameters.

12. The method of claim 1, wherein the chromatography is liquid chromatography.

13. The method of claim 1, wherein the chromatography is gas chromatography.

14. The method of claim 1, wherein the method comprises prior to step b) the further step of fractioning the test sample into at least one first fraction comprising polar compounds and at least one second fraction comprising non-polar compounds.

15. The method of claim 14, wherein the fractioning further comprises fractioning the test sample into at least one third fraction comprising proteins or amino acids.

16. The method of claim 1, wherein the providing in step a) comprises extracting the at least one compound comprised by the test sample.

17. The method claim 1, wherein the test sample is derived from an organism of a plurality of organisms having an essentially identical metabolome.

18. The method of claim 17, wherein the organisms are plants, animals, fungi or bacteria.

19. The method of claim 1, wherein the test sample is derived from cells, from a tissue, or from an organ.

20. The method of claim 1, wherein the test sample is derived from a body fluid.

21. The method of claim 20, wherein the body fluid is blood, serum, plasma, saliva, cerebrospinal liquid, sudor, sperm, vaginal fluid, saliva, tears, feces or urine.

22. The method of claim 1, wherein analyzing the generated raw data comprises a step of correlating and/or comparing at least two vectors, wherein at least one of the at least two vectors is subjected to a shrinkage process for the components of the vector, taking into account the reliability of the component.

23. The method of claim 1, wherein analyzing the generated raw data comprises a step of correlating and/or comparing at least two vectors, wherein a component-wise Match-Mismatch scoring is carried out, generating a Match score and a Mismatch score, wherein the Match score and the Mismatch score are considered separately, preferably by using a ranking of the scores.

24. The method of claim 1, wherein analyzing the generated raw data comprises the steps of selecting significant validated results and classifying the at least one test sample.

25. The method of claim 1, further comprising providing an output result set containing the analyzed results of step d).

26. A method for determining a trait specific for a first sample comprising:
 a) comparing an output result set obtained by the method of claim 25 for a first sample to an output result set obtained by the method of claim 25 for a second sample; and
 b) determining a trait specific for the first sample based on the comparison in step a), wherein a difference in the output result sets is indicative for a trait specific for the first sample.

27. The method of claim 26, wherein the comparing comprises a step of correlating and/or comparing at least two vectors, wherein at least one of the at least two vectors is subjected to a shrinkage process for the components of the vector, taking into account the reliability of the component.

28. The method of claim 26, wherein the comparing comprises a step of correlating and/or comparing at least two vectors, wherein a component-wise Match-Mismatch scoring is carried out, generating a Match score and a Mismatch score, wherein the Match score and the Mismatch score are considered separately, preferably by using a ranking of the scores.

29. The method of claim 26, wherein the comparing comprises the steps of selecting significant validated results and classifying the at least one test sample.

30. A method for determining effects caused by a treatment applied to an organism comprising the method of claim 26 and further comprising determining the effects based on the trait determined for a first sample of the organism.

31. A method for determining a biomarker specific for a first sample comprising the method of claim 26 and further comprising determining the biomarker based on the trait determined for the first sample.

32. A method for determining a mode of action of a compound administered to a organism comprising the method of claim 26 and further comprising determining the mode of action of the compound based on the trait determined for a first sample of the organism.

33. A method for determining a common trait for a first sample and a second sample comprising:
 a) comparing an output result set obtained by the method of claim 25 for a first sample to an output result set obtained by the method of claim 25 for a second sample; and
 b) determining a trait specific for the first sample based on the comparison in step a), wherein a difference in the output result sets is indicative for a trait specific for the first sample.

34. The method of claim 33, wherein the comparing comprises a step of correlating and/or comparing at least two vectors, wherein at least one of the at least two vectors is subjected to a shrinkage process for the components of the vector, taking into account the reliability of the component.

35. The method of claim 33, wherein the comparing comprises a step of correlating and/or comparing at least two vectors, wherein a component-wise Match-Mismatch scoring is carried out, generating a Match score and a Mismatch score, wherein the Match score and the Mismatch score are considered separately, preferably by using a ranking of the scores.

36. The method of claim 33, wherein the comparing comprises the steps of selecting significant validated results and classifying the at least one test sample.

37. A method for determining effects caused by a treatment applied to an organism comprising the method of claim 33 and further comprising determining the effects based on the trait determined for a first sample of the organism.

38. The method of claim 37, wherein the treatment is one or more of genetic modification of the organism, administration of a compound, physical treatments, change of an environmental condition, or radiation applied to the organisms.

39. The method of claim 37, wherein the treatment is one or more of genetic modification of the organism, administration of a compound, physical treatments, change of an environmental condition, or radiation applied to the organisms.

40. A method for determining a biomarker specific for a first sample comprising the method of claim 33 and further comprising determining the biomarker based on the trait determined for the first sample.

41. A method for determining a mode of action of a compound administered to a organism comprising the method of claim 33 and further comprising determining the mode of action of the compound based on the trait determined for a first sample of the organism.

42. The method of claim 41, wherein the organism is a plant and the compound is a herbicidal compound.

43. The method of claim 41, wherein the organism is an insect and the compound is a insecticidal compound.

44. The method of claim 41, wherein the organism is a plant and the compound is a herbicidal compound.

45. The method of claim 41, wherein the organism is an insect and the compound is a insecticidal compound.

46. The method of claim 41, wherein the organism is a phytopathogenic fungus and the compound is a fungicidal compound.

47. A system for carrying out the method of claim 1 comprising operatively linked to each other:
 a) means for determining a compound;
 b) means for monitoring process parameters,
 c) means for analyzing raw results obtained from the means according to (a), wherein the means for analyzing raw results comprise:
  (i) a first database comprising raw results received from the means according to a);
  (ii) a second database comprising monitored process parameters;
  (iii) a third database comprising rules for validating the raw results;
  (iv) a fourth database comprising allocated results of identified compounds; and
  (v) a validation tool adapted to confirm or invalidate raw results based on the rules of the third data base;
 wherein the second, third and fourth database are operatively linked to the first database.

48. The system of claim 47, wherein the first and the fourth database are operatively linked to each other as to allow raw results of the first database to be included as allocated results for identified compounds into the fourth database after evaluation.

49. The system of claim 47, wherein the means for analyzing raw results comprises:
 (v) a fifth database comprising information relating to at least one specific sample identifier operatively linked to at least one other database.

50. The system of claim 49, wherein the specific sample identifier is selected from the group consisting of: sample number, sample origin, sample source, sample treatment, sample run, and sample aliquot.

51. The system of claim 47, wherein the means for analyzing raw results comprises:
(vi) a sixth database comprising biochemical information relating to the identifier operatively linked to at least one other database.

52. The system of claim 47, wherein the means for determining a compound comprise mass spectrometry devices.

53. The system of claim 52, wherein the means for determining further comprise liquid chromatography and/or gas chromatography devices.

54. The system of claim 47, further comprising means for fractioning a sample.

55. The system of claim 47, further comprising means for extraction.

56. A method analyzing a test sample, wherein the test sample comprises at least one compound, the method comprising:
a) providing a test sample comprising at least one compound;
b) determining the at least one compound in the test sample using chromatography coupled mass spectrometry, thereby generating primary raw data;
c) generating raw results from the generated primary raw data by (i) deconvolution of the primary raw data and allocation of the deconvoluted primary raw data to compounds using a reference spectrum and a reference retention index and (ii) allocating intensities and retention times to compounds using predetermined ion masses and time windows; and
d) analyzing the generated raw results by generating a specific profile for the test sample based on the raw results,
wherein the analysis of the test sample is accompanied by an analysis of at least one reference sample;
wherein the test sample and the reference sample are analyzed in an identical sequence in each step of the method.

57. The method of claim 56, wherein the method is assisted by automation.

58. The method of claim 56, wherein the at least one reference sample is selected from the group consisting of:
d. a reference sample comprising a portion of at least one test sample;
e. a reference sample comprising a plurality of defined reference standards;
f. a reference sample comprising a portion of the reference sample (a) and a portion of the reference sample (b).

59. The method of claim 56, wherein the test sample and the reference sample are analyzed in an identical sequence order.

60. The method of claim 59, wherein the sequence order is established prior to analysis of the samples by random positioning of the test sample and the at least one reference sample within the sequence order.

61. The method of claim 56, wherein analyzing the generated raw results further comprises normalization of the validated raw results of the test sample with respect to the validated raw results obtained for the reference sample.

62. The method of claim 56, wherein the method further comprises monitoring of process parameters for the method.

63. The method of claim 62, wherein the validation in step d) further comprises confirming or invalidating raw results based on the monitored process parameters.

64. The method of claim 56, wherein the chromatography is liquid chromatography.

65. The method of claim 56, wherein the chromatography is gas chromatography.

66. The method of claim 56, wherein the method comprises prior to step b) the further step of fractioning the test sample into at least one first fraction comprising polar compounds and at least one second fraction comprising non-polar compounds.

67. The method of claim 66, wherein the fractioning further comprises fractioning the test sample into at least one third fraction comprising proteins or amino acids.

68. The method of claim 56, wherein the providing in step a) comprises extracting the at least one compound comprised by the test sample.

69. The method claim 56, wherein the test sample is derived from an organism of a plurality of organisms having an essentially identical metabolome.

70. The method of claim 69, wherein the organisms are plants, animals, fungi or bacteria.

71. The method of claim 56, wherein the test sample is derived from cells, from a tissue, or from an organ.

72. The method of claim 56, wherein the test sample is derived from a body fluid.

73. The method of claim 72, wherein the body fluid is blood, serum, plasma, saliva, cerebrospinal liquid, sudor, sperm, vaginal fluid, saliva, tears, feces or urine.

74. The method of claim 56, wherein analyzing the generated raw data comprises a step of correlating and/or comparing at least two vectors, wherein at least one of the at least two vectors is subjected to a shrinkage process for the components of the vector, taking into account the reliability of the component.

75. The method of claim 56, wherein analyzing the generated raw data comprises a step of correlating and/or comparing at least two vectors, wherein a component-wise Match-Mismatch scoring is carried out, generating a Match score and a Mismatch score, wherein the Match score and the Mismatch score are considered separately, preferably by using a ranking of the scores.

76. The method of claim 56, wherein analyzing the generated raw data comprises the steps of selecting significant validated results and classifying the at least one test sample.

77. The method of claim 56, further comprising providing an output result set containing the analyzed results of step d).

78. A method for determining a trait specific for a first sample comprising:
c) comparing an output result set obtained by the method of claim 77 for a first sample to an output result set obtained by the method of claim 77 for a second sample; and
d) determining a trait specific for the first sample based on the comparison in step a), wherein a difference in the output result sets is indicative for a trait specific for the first sample.

79. The method of claim 78, wherein the comparing comprises a step of correlating and/or comparing at least two vectors, wherein at least one of the at least two vectors is subjected to a shrinkage process for the components of the vector, taking into account the reliability of the component.

80. The method of claim 78, wherein the comparing comprises a step of correlating and/or comparing at least two vectors, wherein a component-wise Match-Mismatch scoring is carried out, generating a Match score and a Mismatch score, wherein the Match score and the Mismatch score are considered separately, preferably by using a ranking of the scores.

81. The method of claim 78, wherein the comparing comprises the steps of selecting significant validated results and classifying the at least one test sample.

82. A method for determining effects caused by a treatment applied to an organism comprising the method of claim 78 and further comprising determining the effects based on the trait determined for a first sample of the organism.

83. The method of claim 82, wherein the treatment is one or more of genetic modification of the organism, administration of a compound, physical treatments, change of an environmental condition, or radiation applied to the organisms.

84. A method for determining a biomarker specific for a first sample comprising the method of claim 78 and further comprising determining the biomarker based on the trait determined for the first sample.

85. A method for determining a mode of action of a compound administered to a organism comprising the method of claim 78 and further comprising determining the mode of action of the compound based on the trait determined for a first sample of the organism.

86. The method of claim 85, wherein the organism is a plant and the compound is a herbicidal compound.

87. The method of claim 85, wherein the organism is an insect and the compound is a insecticidal compound.

88. A method for determining a common trait for a first sample and a second sample comprising:
  c) comparing an output result set obtained by the method of claim 77 for a first sample to an output result set obtained by the method of claim 77 for a second sample; and
  d) determining a trait specific for the first sample based on the comparison in step a), wherein a difference in the output result sets is indicative for a trait specific for the first sample.

89. The method of claim 88, wherein the comparing comprises a step of correlating and/or comparing at least two vectors, wherein at least one of the at least two vectors is subjected to a shrinkage process for the components of the vector, taking into account the reliability of the component.

90. The method of claim 88, wherein the comparing comprises a step of correlating and/or comparing at least two vectors, wherein a component-wise Match-Mismatch scoring is carried out, generating a Match score and a Mismatch score, wherein the Match score and the Mismatch score are considered separately, preferably by using a ranking of the scores.

91. The method of claim 88, wherein the comparing comprises the steps of selecting significant validated results and classifying the at least one test sample.

92. A method for determining effects caused by a treatment applied to an organism comprising the method of claim 88 and further comprising determining the effects based on the trait determined for a first sample of the organism.

93. The method of claim 92, wherein the treatment is one or more of genetic modification of the organism, administration of a compound, physical treatments, change of an environmental condition, or radiation applied to the organisms.

94. A method for determining a biomarker specific for a first sample comprising the method of claim 88 and further comprising determining the biomarker based on the trait determined for the first sample.

95. A method for determining a mode of action of a compound administered to a organism comprising the method of claim 88 and further comprising determining the mode of action of the compound based on the trait determined for a first sample of the organism.

96. The method of claim 95, wherein the organism is a plant and the compound is a herbicidal compound.

97. The method of claim 95, wherein the organism is an insect and the compound is a insecticidal compound.

98. The method of claim 95, wherein the organism is a phytopathogenic fungus and the compound is a fungicidal compound.

99. A system for carrying out the method of claim 56 comprising operatively linked to each other:
  a) means for determining a compound;
  b) means for monitoring process parameters,
  c) means for analyzing raw results obtained from the means according to (a), wherein the means for analyzing raw results comprise:
    (i) a first database comprising raw results received from the means according to a);
    (ii) a second database comprising monitored process parameters;
    (iii) a third database comprising rules for validating the raw results;
    (iv) a fourth database comprising allocated results of identified compounds; and
    (v) a validation tool adapted to confirm or invalidate raw results based on the rules of the third data base;
  wherein the second, third and fourth database are operatively linked to the first database.

100. The system of claim 99, wherein the first and the fourth database are operatively linked to each other as to allow raw results of the first database to be included as allocated results for identified compounds into the fourth database after evaluation.

101. The system of claim 99, wherein the means for analyzing raw results comprises:
  (v) a fifth database comprising information relating to at least one specific sample identifier operatively linked to at least one other database.

102. The system of claim 101, wherein the specific sample identifier is selected from the group consisting of: sample number, sample origin, sample source, sample treatment, sample run, and sample aliquot.

103. The system of claim 99, wherein the means for analyzing raw results comprises:
  (vi) a sixth database comprising biochemical information relating to the identifier operatively linked to at least one other database.

104. The system of claim 99, wherein the means for determining a compound comprise mass spectrometry devices.

105. The system of claim 104, wherein the means for determining further comprise liquid chromatography and/or gas chromatography devices.

106. The system of claim 99, further comprising means for fractioning a sample.

107. The system of claim 99, further comprising means for extraction.

* * * * *